United States Patent
Bae et al.

(10) Patent No.: US 9,956,270 B2
(45) Date of Patent: May 1, 2018

(54) PHARMACEUTICAL COMPOSITION COMPRISING BEE VENOM-PHOSPHOLIPASE A2 (BV-PLA2) FOR TREATING OR PREVENTING DISEASES RELATED TO DEGRADATION OF ABNORMAL REGULATORY T CELL ACTIVITY

(71) Applicant: UNIVERSITY-INDUSTRY COOPERATION GROUP OF KYUNG HEE UNIVERSITY, Gyeonggi-do (KR)

(72) Inventors: Hyun Su Bae, Seoul (KR); Hyo Jung Lee, Incheon (KR); Gi Hyun Lee, Seoul (KR); Hyun Seong Kim, Busan (KR); Soo Jin Park, Daegu (KR); Eun Sook Chung, Gyeonggi-do (KR); Tae Won Choi, Seoul (KR)

(73) Assignee: INIST ST CO., LTD. (KR)

( * ) Notice: Subject to any disclaimer, the term of this patent is extended or adjusted under 35 U.S.C. 154(b) by 0 days. days.

(21) Appl. No.: 15/387,579

(22) Filed: Dec. 21, 2016

(65) Prior Publication Data
US 2017/0173120 A1    Jun. 22, 2017

Related U.S. Application Data

(62) Division of application No. 14/381,095, filed as application No. PCT/KR2012/004394 on Jun. 4, 2012, now Pat. No. 9,526,767.

(30) Foreign Application Priority Data

Feb. 27, 2012    (KR) .................. 10-2012-0019925

(51) Int. Cl.
| A61P 25/28 | (2006.01) |
| A61K 38/46 | (2006.01) |
| C12N 9/20 | (2006.01) |
| A61K 35/64 | (2015.01) |
| A61K 9/00 | (2006.01) |

(52) U.S. Cl.
CPC .......... *A61K 38/465* (2013.01); *A61K 9/0019* (2013.01); *A61K 35/64* (2013.01); *C12N 9/20* (2013.01); *C12Y 301/01004* (2013.01)

(58) Field of Classification Search
None
See application file for complete search history.

(56) References Cited

FOREIGN PATENT DOCUMENTS

| KR | 10-2011-0067407 A | 6/2011 |
| KR | 10-2011-0078868 A | 7/2011 |
| KR | 10-2011-0080383 A | 7/2011 |
| WO | 2010/134676 A1 | 11/2010 |

OTHER PUBLICATIONS

Son et al., "Therapeutic application of anti-arthritis, pain-releasing, and anti-cancer effects of bee venom and its constituent compounds", Pharmacol. Therap. 115:246-270, 2007.*
Ewan, P., "ABC of allergies, Venom allergy", BMJ 316:1365-1368, 1998.*
Belkaid, Yasmine et al., "Natural regulatory T cells in infectious disease", Nature Immunology, vol. 6, No. 4, Apr. 2005, pp. 353-360.
Bluestone, Jeffrey A. et al., "Therapeutic Vaccination Using CD4+ CD25+ Antigen-Specific Regulatory T Cells", Proceedings of the National Academy of Sciences of the United States of America, vol. 101, Oct. 5, 2004, pp. 14622-14626.
Farooqui et al., "Inhibitors of Brain Phospholipase A2 Activity: Their Neuropharmacological Effects and Therapeutic Importance for the Treatment of Neurologic Disorders", Pharmacological Rev., 58:591-620, 2006.
Gregory et al., "Neurodegeneration associated with genetic defects in phospholipase A2", Neurology, 71;1402-1409, 2008.
Kuchler, Karl et al., "Analysis of the cDNA for phospholipase A2 from honeybee venom glands", Eur. J. Biochem., 184, 249-254 (1989).
Larche, Mark et al., "Peptide-based therapeutic vaccines for allergic and autoimmune diseases", Nature Medicine Supplement, vol. 11, No. 4, Apr. 2005, pp. S69-S76.
Lee, Gihyun, "Bee Venom Attenuates Experimental Autoimmune Encephalomyelitis by Expansion of CD4+CD25 +Foxp3+ Regulatory T Cells", Thesis for the Degree of Oriental Medicine, 2011.
Lee et al, "Effects of bee venom-PLA2 on Regulatory T cells in asthma mice model", J. Immunol., vol. 188, No. 1, Supp., Meeting Abstracts, Abstract No. 173.37, May 1, 2012.
Miyara, Makoto et al., "Global Natural Regulatory T Cell Depletion in Active Systemic Lupus Erythematosus", J. Immunol., 2005, 175:8392-8400.
Moon, Kihwan, International Preliminary Report on Patentability and Written Opinion, PCT/KR2012/004394, dated Sep. 2, 2014.
Ownby et al., "Melittin and Phospholipase A2 from Bee (*Apis mellifera*) Venom Cause Necrosis of Murine Skeletal Muscle In Vivo", Taxicom, vol. 35, No. 1, 67-80, 1997.
Sakaguchi, Shimon, "Naturally Arising CD4+ Regulatory T Cells for Immunologic Self-Tolerance and Negative Control of Immune Responses", Ann. Rev. Immunol., 2004, 22:531-62.

(Continued)

*Primary Examiner* — David Steadman
(74) *Attorney, Agent, or Firm* — Gavrilovich, Dodd & Lindsey LLP

(57) ABSTRACT

The present invention relates to a pharmaceutical composition for treating or preventing a disease related to abnormal suppression of regulatory T cell activity comprising a polypeptide comprising a bee venom-PLA2 amino acid sequence exclusive of a leader sequence as an active ingredient. The secretory bee venom-phospholipase A2 of the present invention activates a regulatory T cell and suppress a differentiation of Th1/Th7. Therefore, the present polypeptide can be used as a pharmaceutical composition for treating or preventing a disease related to abnormal suppression of regulatory T cell activity, i.e. autoimmune diseases, allergic diseases, or neurodegenerative diseases.

1 Claim, 41 Drawing Sheets

(56) References Cited

OTHER PUBLICATIONS

Sakaguchi, Shimon, "Naturally Arising Foxp3-expressing CD25+ CD4+ regulatory T cells in immunological tolerance to self and non-self", Natural Immunology, vol. 6, No. 4, Apr. 2005, pp. 345-352.
Shen et al., "Expression of a bee venom phospholipase A2 from Apis cerana cerana in the baculovirus-insect cell", J. Zhejiang Univ-Sci B (Biomed & Biotechnol), 2010, 11(5):342-349.
Shipolini et al., "The Primary Sequence of Phospholipase-A from Bee Venom", FEBS Letter, 17:39049, 1971.
Suvas, Susmit et al., "CD+CD25+ T Cells Regulate Virus-specific Primary and Memory CD8+ T Cell Responses", J. Exp. Med. vol. 198, No. 6, Sep. 15, 2003, pp. 889-901.
Wildin, Robert S. et al., "The immune dysregulation polyendocrinopathy, enteropathy, X-linked syndrome (IPEX) is caused by mutations of FOXP3", Nature Genetics, vol. 27, Jan. 2001, pp. 20-21.
International Search Report, PCT/KR2012/004394, dated Oct. 31, 2012.
Constantinescu et al., "Experimental autoimmune encephalomyelitis (EAE) as a model for multiple sclerosis," Br. J. of Pahrmacol., 164:1079-1106, 2011.
Mattozzi et al., "Importance of Regulatory T Cells in the Pahtogenesis of Psoriasis: Review of the Literature," Dermatology, Basel, 227(2):134-45, Nov. 2013.

\* cited by examiner

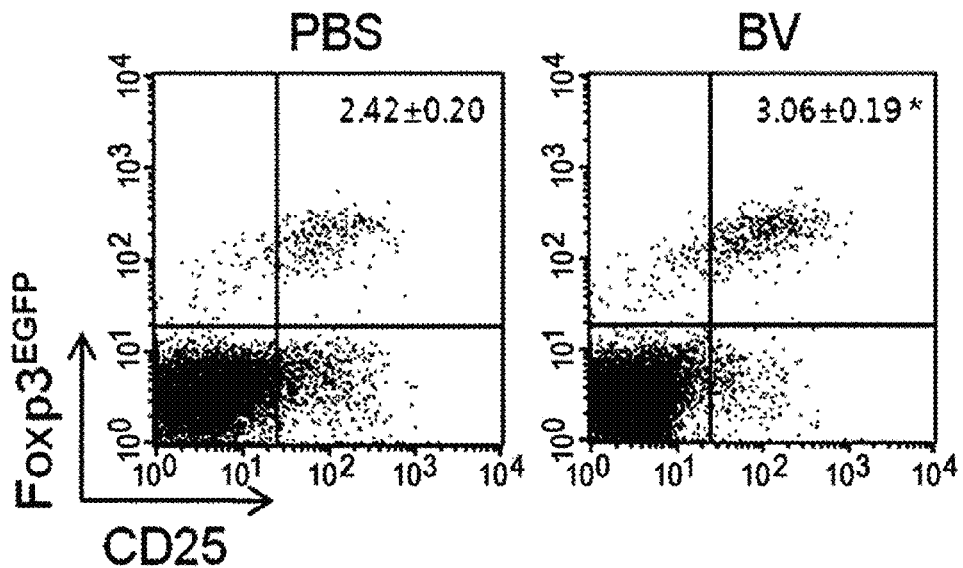
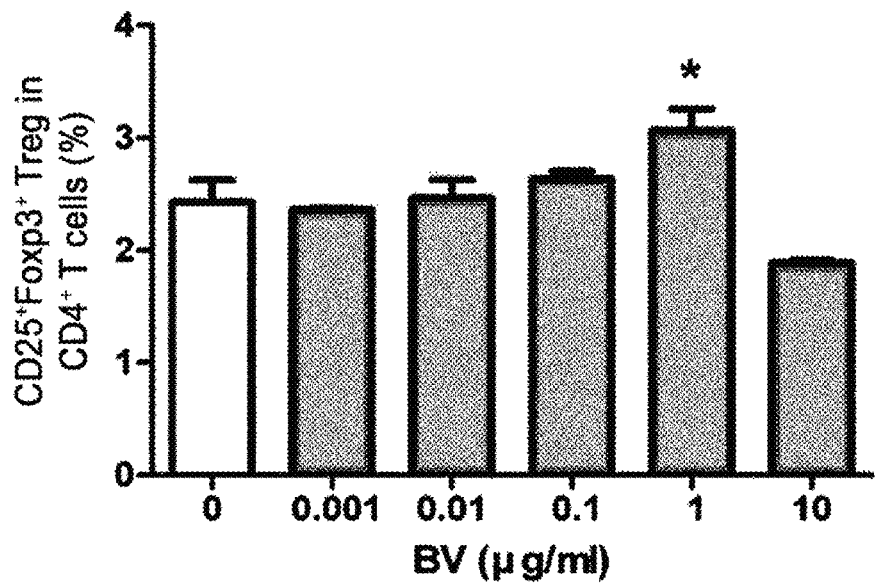
FIG. 2A

CON

OVA

OVA+PLA2

OVA-T+PLA2

OVA-T

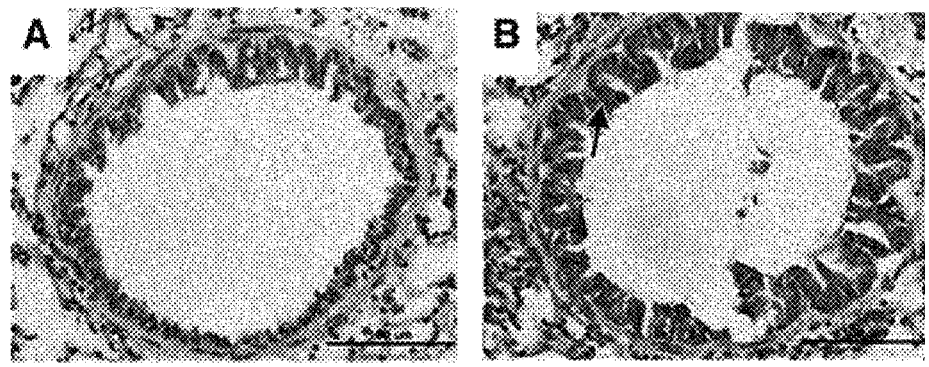
FIG. 17A CON
FIG. 17B OVA
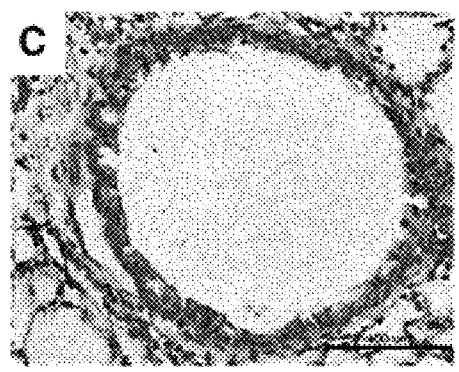
FIG. 17C OVA+PLA2
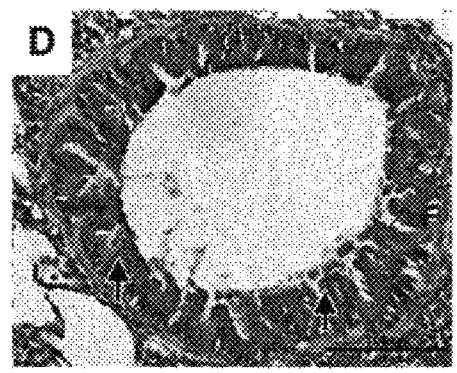
FIG. 17D OVA-T+PLA2
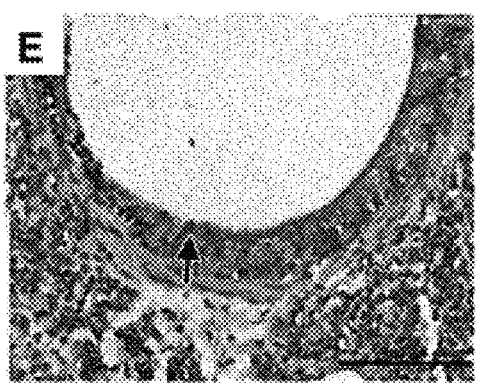
FIG. 17E OVA-T

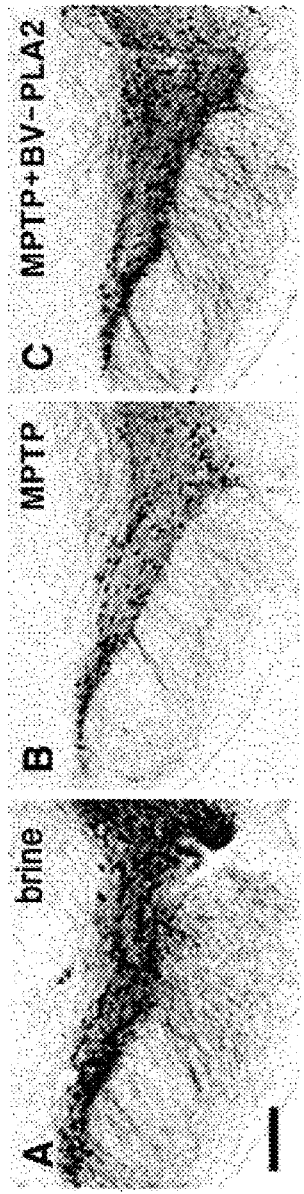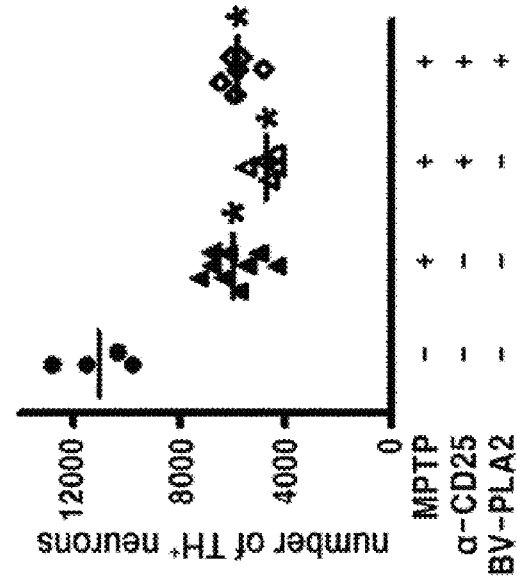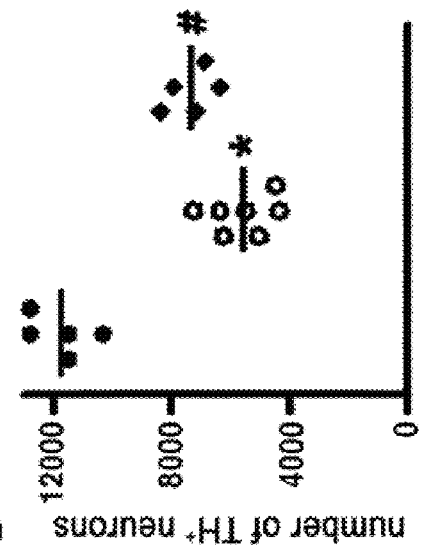
FIG. 19A FIG. 19B FIG. 19C FIG. 19D FIG. 19E

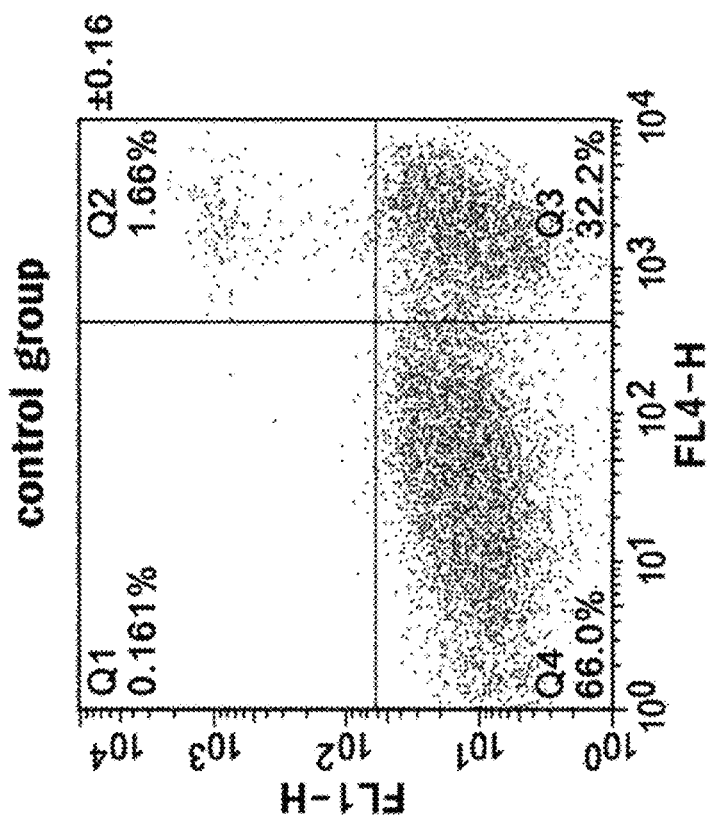
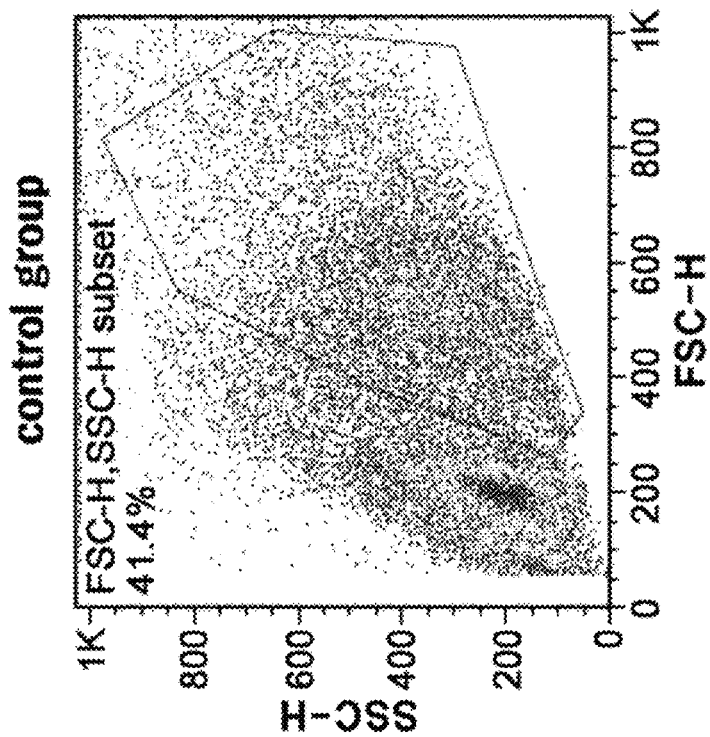
FIG. 22A

SEQUENCE LISTING

<160> NUMBER OF SEQ ID NOS: 24

<210> SEQ ID NO 1
<211> LENGTH: 167
<212> TYPE: PRT
<213> ORGANISM: Apis mellifera
<220> FEATURE:
<221> NAME/KEY: misc_feature
<223> OTHER INFORMATION: PLA2 1-167

<400> SEQUENCE: 1

Met Gln Val Val Leu Gly Ser Leu Phe Leu Leu Leu Ser Thr Ser
1               5                   10                  15

His Gly Trp Gln Ile Arg Asp Arg Ile Gly Asp Asn Glu Leu Glu Glu
            20                  25                  30

Arg Ile Ile Tyr Pro Gly Thr Leu Trp Cys Gly His Gly Asn Lys Ser
            35                  40                  45

Ser Gly Pro Asn Glu Leu Gly Arg Phe Lys His Thr Asp Ala Cys Cys
        50                  55                  60

Arg Thr His Asp Met Cys Pro Asp Val Met Ser Ala Gly Glu Ser Lys
65                  70                  75                  80

His Gly Leu Thr Asn Thr Ala Ser His Thr Arg Leu Ser Cys Asp Cys
                85                  90                  95

Asp Asp Lys Phe Tyr Asp Cys Leu Lys Asn Ser Ala Asp Thr Ile Ser
            100                 105                 110

Ser Tyr Phe Val Gly Lys Met Tyr Phe Asn Leu Ile Asp Thr Lys Cys
            115                 120                 125

Tyr Lys Leu Glu His Pro Val Thr Gly Cys Gly Glu Arg Thr Glu Gly
        130                 135                 140

Arg Cys Leu His Tyr Thr Val Asp Lys Ser Lys Pro Lys Val Tyr Gln
145                 150                 155                 160

Trp Phe Asp Leu Arg Lys Tyr
                165

<210> SEQ ID NO 2
<211> LENGTH: 134
<212> TYPE: PRT
<213> ORGANISM: Apis mellifera
<220> FEATURE:
<221> NAME/KEY: misc_feature
<223> OTHER INFORMATION: PLA2 34-167

<400> SEQUENCE: 2

Ile Ile Tyr Pro Gly Thr Leu Trp Cys Gly His Gly Asn Lys Ser Ser
1               5                   10                  15

Gly Pro Asn Glu Leu Gly Arg Phe Lys His Thr Asp Ala Cys Cys Arg
            20                  25                  30

Thr His Asp Met Cys Pro Asp Val Met Ser Ala Gly Glu Ser Lys His
            35                  40                  45

Gly Leu Thr Asn Thr Ala Ser His Thr Arg Leu Ser Cys Asp Cys Asp
        50                  55                  60

Asp Lys Phe Tyr Asp Cys Leu Lys Asn Ser Ala Asp Thr Ile Ser Ser
65                  70                  75                  80

Tyr Phe Val Gly Lys Met Tyr Phe Asn Leu Ile Asp Thr Lys Cys Tyr
                85                  90                  95

Lys Leu Glu His Pro Val Thr Gly Cys Gly Glu Arg Thr Glu Gly Arg
            100                 105                 110

Cys Leu His Tyr Thr Val Asp Lys Ser Lys Pro Lys Val Tyr Gln Trp

```
                115                 120                 125
Phe Asp Leu Arg Lys Tyr
    130

<210> SEQ ID NO 3
<211> LENGTH: 33
<212> TYPE: PRT
<213> ORGANISM: Apis mellifera
<220> FEATURE:
<221> NAME/KEY: misc_feature
<223> OTHER INFORMATION: PLA2 1-33

<400> SEQUENCE: 3

Met Gln Val Val Leu Gly Ser Leu Phe Leu Leu Leu Leu Ser Thr Ser
1               5                   10                  15

His Gly Trp Gln Ile Arg Asp Arg Ile Gly Asp Asn Glu Leu Glu Glu
            20                  25                  30

Arg

<210> SEQ ID NO 4
<211> LENGTH: 25
<212> TYPE: PRT
<213> ORGANISM: Artificial Sequence
<220> FEATURE:
<223> OTHER INFORMATION: Additive to N-terminal region

<400> SEQUENCE: 4

Gly His Asn His Asn His Asn His Asn His Asn His Asn Ala Ala Gly
1               5                   10                  15

Asp Asp Asp Asp Lys Ala Ser Val Asp
            20                  25

<210> SEQ ID NO 5
<211> LENGTH: 9
<212> TYPE: PRT
<213> ORGANISM: Artificial Sequence
<220> FEATURE:
<223> OTHER INFORMATION: Additive to C-terminal region

<400> SEQUENCE: 5

Ala Asn Ser Gly Gly Arg Leu Ile Asn
1               5

<210> SEQ ID NO 6
<211> LENGTH: 168
<212> TYPE: PRT
<213> ORGANISM: Artificial Sequence
<220> FEATURE:
<223> OTHER INFORMATION: C-type recombinant BV-PLA2

<400> SEQUENCE: 6

Gly His Asn His Asn His Asn His Asn His Asn His Asn Ala Ala Gly
1               5                   10                  15

Asp Asp Asp Asp Lys Ala Ser Val Asp Ile Ile Tyr Pro Gly Thr Leu
            20                  25                  30

Trp Cys Gly His Gly Asn Lys Ser Ser Gly Pro Asn Glu Leu Gly Arg
        35                  40                  45

Phe Lys His Thr Asp Ala Cys Cys Arg Thr His Asp Met Cys Pro Asp
    50                  55                  60

Val Met Ser Ala Gly Glu Ser Lys His Gly Leu Thr Asn Thr Ala Ser
65                  70                  75                  80

His Thr Arg Leu Ser Cys Asp Cys Asp Asp Lys Phe Tyr Asp Cys Leu
```

```
                    85                  90                  95
Lys Asn Ser Ala Asp Thr Ile Ser Ser Tyr Phe Val Gly Lys Met Tyr
                100                 105                 110

Phe Asn Leu Ile Asp Thr Lys Cys Tyr Lys Leu Glu His Pro Val Thr
            115                 120                 125

Gly Cys Gly Glu Arg Thr Glu Gly Arg Cys Leu His Tyr Thr Val Asp
        130                 135                 140

Lys Ser Lys Pro Lys Val Tyr Gln Trp Phe Asp Leu Arg Lys Tyr Ala
145                 150                 155                 160

Asn Ser Gly Gly Arg Leu Ile Asn
                165

<210> SEQ ID NO 7
<211> LENGTH: 201
<212> TYPE: PRT
<213> ORGANISM: Artificial Sequence
<220> FEATURE:
<223> OTHER INFORMATION: F-type recombinant BV-PLA2

<400> SEQUENCE: 7

Met Gly His Asn His Asn His Asn His Asn His Asn Ala Ala
1               5                   10                  15

Gly Asp Asp Asp Lys Ala Ser Val Asp Gln Val Val Leu Gly Ser
            20                  25                  30

Leu Phe Leu Leu Leu Leu Ser Thr Ser His Gly Trp Gln Ile Arg Asp
        35                  40                  45

Arg Ile Gly Asp Asn Glu Leu Glu Arg Ile Ile Tyr Pro Gly Thr
    50                  55                  60

Leu Trp Cys Gly His Gly Asn Lys Ser Ser Gly Pro Asn Glu Leu Gly
65                  70                  75                  80

Arg Phe Lys His Thr Asp Ala Cys Cys Arg Thr His Asp Met Cys Pro
                85                  90                  95

Asp Val Met Ser Ala Gly Glu Ser Lys His Gly Leu Thr Asn Thr Ala
                100                 105                 110

Ser His Thr Arg Leu Ser Cys Asp Cys Asp Asp Lys Phe Tyr Asp Cys
            115                 120                 125

Leu Lys Asn Ser Ala Asp Thr Ile Ser Ser Tyr Phe Val Gly Lys Met
        130                 135                 140

Tyr Phe Asn Leu Ile Asp Thr Lys Cys Tyr Lys Leu Glu His Pro Val
145                 150                 155                 160

Thr Gly Cys Gly Glu Arg Thr Glu Gly Arg Cys Leu His Tyr Thr Val
                165                 170                 175

Asp Lys Ser Lys Pro Lys Val Tyr Gln Trp Phe Asp Leu Arg Lys Tyr
            180                 185                 190

Ala Asn Ser Gly Gly Arg Leu Ile Asn
        195                 200

<210> SEQ ID NO 8
<211> LENGTH: 166
<212> TYPE: PRT
<213> ORGANISM: Artificial Sequence
<220> FEATURE:
<223> OTHER INFORMATION: B-type recombinant BV-PLA2

```
Asp Asp Asp Asp Lys Ala Ser Val Asp Met Gln Val Leu Gly Ser
            20                  25                  30

Leu Phe Leu Leu Leu Ser Thr Ser His Gly Trp Gln Ile Arg Asp
        35                  40                  45

Arg Ile Gly Asp Asn Glu Leu Glu Arg Ile Ile Tyr Pro Gly Thr
    50                  55                  60

Leu Trp Cys Gly His Gly Asn Lys Ser Ser Gly Pro Asn Glu Leu Gly
65                  70                  75                  80

Arg Phe Lys His Thr Asp Ala Cys Cys Arg Thr His Asp Met Cys Pro
                85                  90                  95

Asp Val Met Ser Ala Gly Glu Ser Lys His Gly Leu Thr Asn Thr Ala
            100                 105                 110

Ser His Thr Arg Leu Ser Cys Asp Cys Asp Lys Phe Tyr Asp Cys
        115                 120                 125

Leu Lys Asn Ser Ala Asp Thr Ile Ser Ser Tyr Phe Val Gly Lys Met
    130                 135                 140

Tyr Phe Asn Leu Ile Asp Thr Lys Cys Tyr Lys Leu Glu Ala Asn Ser
145                 150                 155                 160

Gly Gly Arg Leu Ile Asn
                165
```

<210> SEQ ID NO 9
<211> LENGTH: 99
<212> TYPE: PRT
<213> ORGANISM: Artificial Sequence
<220> FEATURE:
<223> OTHER INFORMATION: A-type BV-PLA2 fragment

<400> SEQUENCE: 9

```
Ile Ile Tyr Pro Gly Thr Leu Trp Cys Gly His Gly Asn Lys Ser Ser
1               5                   10                  15

Gly Pro Asn Glu Leu Gly Arg Phe Lys His Thr Asp Ala Cys Cys Arg
            20                  25                  30

Thr His Asp Met Cys Pro Asp Val Met Ser Ala Gly Glu Ser Lys His
        35                  40                  45

Gly Leu Thr Asn Thr Ala Ser His Thr Arg Leu Ser Cys Asp Cys Asp
    50                  55                  60

Asp Lys Phe Tyr Asp Cys Leu Lys Asn Ser Ala Asp Thr Ile Ser Ser
65                  70                  75                  80

Tyr Phe Val Gly Lys Met Tyr Phe Asn Leu Ile Asp Thr Lys Cys Tyr
                85                  90                  95

Lys Leu Glu
```

<210> SEQ ID NO 10
<211> LENGTH: 133
<212> TYPE: PRT
<213> ORGANISM: Artificial Sequence
<220> FEATURE:
<223> OTHER INFORMATION: A-type recombinant BV-PLA2

<400> SEQUENCE: 10

```
Gly His Asn His Asn His Asn His Asn His Asn Ala Ala Gly
1               5                   10                  15

Asp Asp Asp Asp Lys Ala Ser Val Asp Ile Ile Tyr Pro Gly Thr Leu
            20                  25                  30

Trp Cys Gly His Gly Asn Lys Ser Ser Gly Pro Asn Glu Leu Gly Arg
        35                  40                  45
```

```
Phe Lys His Thr Asp Ala Cys Cys Arg Thr His Asp Met Cys Pro Asp
 50                  55                  60

Val Met Ser Ala Gly Glu Ser Lys His Gly Leu Thr Asn Thr Ala Ser
 65                  70                  75                  80

His Thr Arg Leu Ser Cys Asp Cys Asp Lys Phe Tyr Asp Cys Leu
                 85                  90                  95

Lys Asn Ser Ala Asp Thr Ile Ser Ser Tyr Phe Val Gly Lys Met Tyr
                100                 105                 110

Phe Asn Leu Ile Asp Thr Lys Cys Tyr Lys Leu Glu Ala Asn Ser Gly
                115                 120                 125

Gly Arg Leu Ile Asn
                130
```

<210> SEQ ID NO 11
<211> LENGTH: 168
<212> TYPE: PRT
<213> ORGANISM: Artificial Sequence
<220> FEATURE:
<223> OTHER INFORMATION: C-type mutein(H34Q) recombinant BV-PLA2

<400> SEQUENCE: 11

Gly His Asn His Asn His Asn His Asn His Asn His Asn Ala Ala Gly
1               5                   10                  15

Asp Asp Asp Asp Lys Ala Ser Val Asp Ile Ile Tyr Pro Gly Thr Leu
            20                  25                  30

Trp Cys Gly His Gly Asn Lys Ser Ser Gly Pro Asn Glu Leu Gly Arg
        35                  40                  45

Phe Lys His Thr Asp Ala Cys Cys Arg Thr Gln Asp Met Cys Pro Asp
    50                  55                  60

Val Met Ser Ala Gly Glu Ser Lys His Gly Leu Thr Asn Thr Ala Ser
65                  70                  75                  80

His Thr Arg Leu Ser Cys Asp Cys Asp Asp Lys Phe Tyr Asp Cys Leu
                85                  90                  95

Lys Asn Ser Ala Asp Thr Ile Ser Ser Tyr Phe Val Gly Lys Met Tyr
            100                 105                 110

Phe Asn Leu Ile Asp Thr Lys Cys Tyr Lys Leu Glu His Pro Val Thr
        115                 120                 125

Gly Cys Gly Glu Arg Thr Glu Gly Arg Cys Leu His Tyr Thr Val Asp
    130                 135                 140

Lys Ser Lys Pro Lys Val Tyr Gln Trp Phe Asp Leu Arg Lys Tyr Ala
145                 150                 155                 160

Asn Ser Gly Gly Arg Leu Ile Asn
                165

<210> SEQ ID NO 12
<211> LENGTH: 25
<212> TYPE: DNA
<213> ORGANISM: Artificial Sequence
<220> FEATURE:
<223> OTHER INFORMATION: F-type BV-PLA2 primer (Forward)

<400> SEQUENCE: 12
aatgtcgacc aagtcgttct cggat 25

<210> SEQ ID NO 13
<211> LENGTH: 24
<212> TYPE: DNA
<213> ORGANISM: Artificial Sequence
<220> FEATURE:

```
<223> OTHER INFORMATION: F-type BV-PLA2 primer (Reverse)

<400> SEQUENCE: 13
aaggaattct tatcaatact tgcg                                          24

<210> SEQ ID NO 14
<211> LENGTH: 24
<212> TYPE: PRT
<213> ORGANISM: Artificial Sequence
<220> FEATURE:
<223> OTHER INFORMATION: A-type BV-PLA2 primer (Forward)

<400> SEQUENCE: 14

Ala Ala Thr Gly Thr Cys Gly Ala Cys Ala Thr Ala Thr Ala Thr
1               5                   10                  15

Ala Thr Cys Cys Ala Gly Gly Ala
            20

<210> SEQ ID NO 15
<211> LENGTH: 27
<212> TYPE: DNA
<213> ORGANISM: Artificial Sequence
<220> FEATURE:
<223> OTHER INFORMATION: A-type BV-PLA2 primer (Reverse)

<400> SEQUENCE: 15
aaggaattct cacagtttgt aacactt                                       27

<210> SEQ ID NO 16
<211> LENGTH: 25
<212> TYPE: DNA
<213> ORGANISM: Artificial Sequence
<220> FEATURE:
<223> OTHER INFORMATION: B-type BV-PLA2 primer (Forward)

<400> SEQUENCE: 16
aatgtcgacc aagtcgttct cggat                                         25

<210> SEQ ID NO 17
<211> LENGTH: 27
<212> TYPE: DNA
<213> ORGANISM: Artificial Sequence
<220> FEATURE:
<223> OTHER INFORMATION: B-type BV-PLA2 primer (Reverse)

<400> SEQUENCE: 17
aaggaattct cacagtttgt aacactt                                       27

<210> SEQ ID NO 18
<211> LENGTH: 24
<212> TYPE: DNA
<213> ORGANISM: Artificial Sequence
<220> FEATURE:
<223> OTHER INFORMATION: C-type BV-PLA2 primer (Forward)

<400> SEQUENCE: 18
aatgtcgaca taatatatcc agga                                          24

<210> SEQ ID NO 19
<211> LENGTH: 24
<212> TYPE: DNA
<213> ORGANISM: Artificial Sequence
<220> FEATURE:
<223> OTHER INFORMATION: C-type BV-PLA2 primer (Reverse)

<400> SEQUENCE: 19
```

```
aaggaattct tatcaatact tgcg                                           24

<210> SEQ ID NO 20
<211> LENGTH: 34
<212> TYPE: DNA
<213> ORGANISM: Artificial Sequence
<220> FEATURE:
<223> OTHER INFORMATION: C-type mutein (H34Q) BV-PLA2 primer (Forward)

<400> SEQUENCE: 20
gcatgctgtc gaacccaaga catgtgcccg gacg                                34

<210> SEQ ID NO 21
<211> LENGTH: 34
<212> TYPE: DNA
<213> ORGANISM: Artificial Sequence
<220> FEATURE:
<223> OTHER INFORMATION: C-type mutein (H34Q) BV-PLA2 primer (Reverse)

<400> SEQUENCE: 21
cgtccgggca catgtcttgg gttcgacagc atgc                                34

<210> SEQ ID NO 22
<211> LENGTH: 144
<212> TYPE: DNA
<213> ORGANISM: Artificial Sequence
<220> FEATURE:
<223> OTHER INFORMATION: recombinant BV-PLA2

<400> SEQUENCE: 22
agaaggagat ataccatggg tcataatcat aatcataatc ataatcataa tcacaacgct     60
gcaggtgatg acgatgataa ggcctctgtc gaccagatct ctaagcttgc gaattctggc    120
ggccgcttaa ttaattaatc taga                                          144

<210> SEQ ID NO 23
<211> LENGTH: 40
<212> TYPE: PRT
<213> ORGANISM: Artificial Sequence
<220> FEATURE:
<223> OTHER INFORMATION: recombinant BV-PLA2

<400> SEQUENCE: 23

Met Gly His Asn His Asn His Asn His Asn His Asn His Asn Ala Ala
1               5                   10                  15

Gly Asp Asp Asp Asp Lys Ala Ser Val Asp Gln Ile Ser Lys Leu Ala
            20                  25                  30

Asn Ser Gly Gly Arg Leu Ile Asn
        35                  40

<210> SEQ ID NO 24
<211> LENGTH: 21
<212> TYPE: PRT
<213> ORGANISM: Artificial Sequence
<220> FEATURE:
<223> OTHER INFORMATION: Murine MOG 35-55

<400> SEQUENCE: 24

Met Glu Val Gly Trp Tyr Arg Ser Pro Phe Ser Arg Val Val His Leu
1               5                   10                  15

Tyr Arg Asn Gly Lys
            20
```

PHARMACEUTICAL COMPOSITION COMPRISING BEE VENOM-PHOSPHOLIPASE A2 (BV-PLA2) FOR TREATING OR PREVENTING DISEASES RELATED TO DEGRADATION OF ABNORMAL REGULATORY T CELL ACTIVITY

CROSS REFERENCE TO RELATED APPLICATIONS

This application is a divisional of U.S. application Ser. No. 14/381,095, filed Dec. 8, 2014, which is a U.S. National Stage Application filed under 35 U.S.C. 371 and claims priority to International Application No. PCT/KR2012/004394, filed Jun. 4, 2012, which application claims priority to Korean Application No. 10-2012-0019925, filed Feb. 27, 2012, the disclosures of which are incorporated herein by reference in their entirety.

TECHNICAL FIELD

The present invention relates to a pharmaceutical composition for treating or preventing diseases related to abnormal suppression of regulatory T cell activity containing bee venom-phospholipase A2 (BV-PLA2) as an active ingredient.

BACKGROUND ART

One of the most important features in all normal subjects is that they do not harmfully react against antigenic materials forming a self while they are capable of recognizing, reacting to, and removing numerous non-self antigens. The above biological phenomenon of not being responsive to self antigens is called immunologic unresponsiveness or tolerance. Self-tolerance occurs when the lymphocytes which may have specific receptors for self antigens are removed or when the reactive function that responds to self antigens after being contacted is inactivated. When there is a problem in inducing or maintaining self-tolerance an immune response occurs against self antigens, and the diseases caused thereby is called an autoimmune disease.

Multiple sclerosis (MS) is a chronic inflammatory autoimmune disease in the central nervous system affecting more than a million people worldwide. MS causes substantial disorders due to deficiency in sensation and locomotion, autonomy and neurocognitive functions. The mechanism of developing the disease generally appears to be an autoimmune pathology in which $CD4^+$ T helper 1 cells (Th1: IFN-$\gamma$ producing $CD4^+$ T cells), T helper 17 cells (Th17: IL-17A producing $CD4^+$ T cells) and regulatory T cells (Treg) play important roles. Many clinical and pathological characteristics of the experimental autoimmune encephalomyelitis (EAE), which is an animal model of human MS, show proximal similarity to that of MS. Accordingly, EAE has been generally used as an experimental model system for studying the mechanism of MS development and for testing the efficacy of potential therapeutic agents for MS. Therapeutic agents for controlling diseases such as IFN-$\beta$ and glatiramer acetate have been widely used for MS treatment, showing advantageous effects. However, due to limitations on therapeutic methods many MS patients have been looking for selective alternative therapies. Allegedly, about 50% to 75% of MS patients are using at least one complementary and alternative medicinal therapy.

An allergic disease refers to a disease caused by a disorder in immune system in which a substance non-harmful to normal people causes hypersensitivities with various symptoms to particular people. A substance that causes an allergic disease is called an allergen or antigen, and pollens, antibiotics, drugs, dusts, foods, cold air, sunlight, etc., may causes the allergies. The symptoms of the allergic diseases include hives, sneezing, pruritus, rhinorrhea, coughs, hay fever, ocular hyperemia, eczema, rashes, etc. Representative allergic diseases are allergic asthma, which accompany symptoms such as airway constriction, increase in the secretion of mucus liquid in the lungs, dyspnea, and coughs, and additionally may include atopic dermatitis, conjunctivitis, rhinitis, and ulcerative colitis.

Neurodegenerative diseases are associated with symptoms such as degeneration, loss of functions, and often apoptosis of neurons. Since these symptoms are progressive they are often highly destructive unlike the neurodegenerative diseases. Patients with neurodegenerative diseases may experience extreme deterioration in their cognitive or motor performance. Accordingly, the quality of their lives and expectation thereto may be considerably deteriorated.

Parkinson's disease (PD) is a representative progressive neurodegenerative disease characterized by loss of dopaminergic (DA) neurons in substantia nigra (SN), and shaking, rigidity, slowness of movement, and bradykinesia due to decrease in dopamine in striatum (STR). PD is a sporadic disease whose pathogenesis has not been identified. According to the evidence accumulated so far, neuroinflammation appears to play an important role in the pathogenesis of PD. The primary trigger of neuroinflammation is activated microglia, which are innate immune cells of the central nervous system (CNS) discovered in degenerative DA neurons and therearound. Microglia are dramatically activated by responding to neuronal damage, and ROS and/or produce various potential neurotoxins including proinflammatory cytokines. Until recently, the role of the adoptive immune system has been increasingly emphasized in PD pathogenesis. Examples of therapeutic drugs for treating PD include L-dopa preparation, dopamine agonists, anticholinergics, Eldepryl (depreyl), etc. Most of these drugs are involved in regulating the symptoms of PD rather than treating its cause, and thus they should be administered continuously without cessation. However, long-term administration of these drugs may lead to drug intoxication. For example, anticholinergics may cause disorders in autonomic nervous system or abnormalities in mental functions and thus its long-term administration to people of senile age are limited. Additionally, the efficacies of L-dopa preparations may progressively deteriorate as the duration of its administration becomes long, and may also incur adverse effects such as twisting of the body and involuntary movements of hands or legs. Accordingly, in order to prevent the adverse effects, active efforts have been made to develop a therapeutic agent derived from natural substances for PD treatment. For example, pharmaceutical compositions containing a Scutellariae Radix extract (KR Patent Application Publication No. 2001-0081188), a *Beauveria Bassiana* 101A extract (KR Patent Application Publication No. 2004-0012396), a peach leaf extract (KR Patent Application Publication No. 2010-0060949), etc., as active ingredients have been disclosed. Although the components derived from natural substances have no adverse effects they are disadvantageous due to low therapeutic effects for PD treatment.

Since the introduction of the regulatory T cell concept on early 1970s by Gershon based on the possibility of the presence of T cells capable of controlling and inhibiting the effector functions of palliative T cells (conventional T cells), and its first disclosure (R. K Gershon and K Kondo, Immunology, 1970, 18: 723-37), studies have been focused on the elucidation of biological characteristics and functions of regulatory T cells in many fields of immunology.

In particular, since Sakaguchi suggested in 1995 that CD25 can act as an important phenotypic marker for naturally-occurring CD4+ regulatory T cells (S. Sakaguchi et al., J. Immunol., 1995, 155: 1151-1164), the studies have focused on the roles and importance of regulatory T cells in inducing peripheral tolerance regarding self antigens.

Bee venom is an alternative medicine widely used for the treatment of a few immune diseases, in particular rheumatoid arthritis. The existing studies have disclosed that bee venom treatment can alleviate rheumatoid arthritis and has an anti-inflammatory effect in humans and experimental animals. Additionally, although there are evidence-based descriptive reports on the alleged improvement of neuropathy symptoms by MS patients who have received multiple repeated bee venom acupunctures a conclusive decision on the bee venom efficacy has not been made due to lack of detailed studies, and currently there is almost no evidence supporting the use of bee venom in MS treatment.

Meanwhile, although bee venom is widely used as an alternative medicine, considering the risk of hypersensitivity, shock response, etc., in using bee venom, it is necessary to identify specific active ingredients and the working mechanism of bee venom, and to use it as a more purified drug.

DETAILED DESCRIPTION OF THE INVENTION

Technical Problem

Accordingly, the present inventors have endeavored to study the active ingredients of bee venom having therapeutic effects on diseases and their working mechanisms, and found that phospholipase A2 (PLA2) among the various bee venom ingredients, in particular a polypeptide containing a secretory bee venom-PLA2 amino acid sequence exclusive of a leader sequence, can activate regulatory T cells thereby exhibiting effects of preventing and treating autoimmune diseases, allergic diseases, or neurodegenerative diseases.

Technical Solution

An objective of the present invention is to provide a pharmaceutical composition for treating or preventing diseases related to abnormal suppression of regulatory T cell activity containing a polypeptide which includes a bee venom-PLA2 (BV-PLA2) amino acid sequence exclusive of a leader sequence.

Advantageous Effects

According to the present invention, a polypeptide including a bee venom-PLA2 amino acid sequence exclusive of a leader sequence can inhibit Th1/Th17 differentiation while activating regulatory T cells. Accordingly, the polypeptide of the present invention can be useful as a pharmaceutical composition for preventing or treating diseases related to abnormal suppression of regulatory T cell activity, i.e., autoimmune diseases, allergic diseases, and neurodegenerative diseases, without the risks of using unpurified and unisolated bee venom.

BRIEF DESCRIPTION OF THE DRAWINGS

FIG. 2A-E shows graphs illustrating the effect of bee venom (BV) on the expression of Foxp3 of CD4+CD25+ Foxp3+ Treg and CD4+CD25+ Treg. (A) and (B) show the cytometry analysis results of the splenocytes of Foxp3$^{EGFP}$ C57BL/6 mice after treating them with various concentrations of bee venom (0, 0.001, 0.01, 0.1, 1, and 10 μg/ml) for 24 hours followed by staining with CD4 and anti-CD25 antibodies. (A) shows the analysis results of CD25 and Foxp3 positive cells after gating on CD4+ T cells, and (A) shows the analysis results of expression rate of Foxp3$^{EGFP}$ after gating on CD4+CD25+ T cells. (C) through (E) show the results of flow cytometry analysis of murine cells isolated from a Foxp3$^{EGFP}$ C57BL/6 mouse after treating them with bee venom (1 μg/ml) for 24 hours followed by staining with anti-CD4 and anti-CD25 antibodies. (C) shows the result of flow cytometry analysis of CD4+ T cells, (D) shows that of the CD4+CD25− T cells, and (E) shows that of the CD4+CD25+ Treg cells. The numbers within the dot plots of (A), (C), and (D) respectively represent the percentage of cells belonging to the corresponding quadrant. The percentages of (B) and (E) represent a proportion of the gated Foxp3$^{high}$ cells in the CD4+CD25+ Treg. Experiments were repeated 3 times and one representative graph is shown, wherein data is shown via mean±standard error of the mean (SEM) (*p<0.05, ***p<0.001 vs. a PBS-treated cell group).

FIG. 17A-E shows pictures illustrating the effect of BV-PLA2 (secretory type) on the histopathological changes in the lung tissues of OVA-induced allergic asthma mice. The lung tissues were stained with periodic acid-Schiff (PAS) (400× magnification). The results shown represent: (A) a group of PBS-test infected mice treated with PBS (CON); (B) a group of OVA-test infected mice treated with PBS (OVA); (C) OVA-test infected mice treated with BV-PLA2 (0.2 mg/kg) (OVA+PLA2); (D) a group of OVA and anti-CD25 antibodies-test infected mice treated with BV-PLA2 (0.2 mg/kg) (OVA-T+PLA2); and (E) a group of OVA and anti-CD25 antibodies-test infected mice (OVA-T).

FIG. 19A-E shows a graph illustrating the preventive effect of BV-PLA2 (secretory type) on dopaminergic (DA) neuronal cell death in substantia nigra (SN) of 1-methyl-4-phenyl-1,2,3,6-tetrahydropyridine (MPTP)-addicted mice. The MPTP-addicted mice were treated with BVPLA2 (0.5 mg/kg) or brine for 6 days starting 12 hours after the final MPTP injection. Some of the mice were administered with the anti-CD25 antibodies (1 mg/kg) one day prior to the MPTP injection. Seven days after the MPTP-addiction, the brain slices were immunostained with α-TH antibodies for the DA neurons. (A) shows the result where the brine-injected mice were treated with brine, (B) shows the result where the MPTP-addicted mice were treated with brine, and (C) shows the result where the MPTP-addicted mice were treated with BV-PLA2. (D) and (E) show the number of TH positive neurons counted. For each experimental group, 8 to 9 experimental animals were used. In (A) through (C), the scale bar represents a length of 200 μm ($*p<0.001$ vs. brine-treated control group, $\#p<0.01$ vs. MPTP-addicted mice).

FIG. 22A through 22E show the results of flow cytometry analysis of the naturally occurring and recombinant BV-PLA2s stained with anti-CD4 and anti-CD25 antibodies for confirmation of their effects on the CD4$^+$CD25$^+$Foxp3$^+$ regulatory T cells.

BEST MODE

Figure 1:
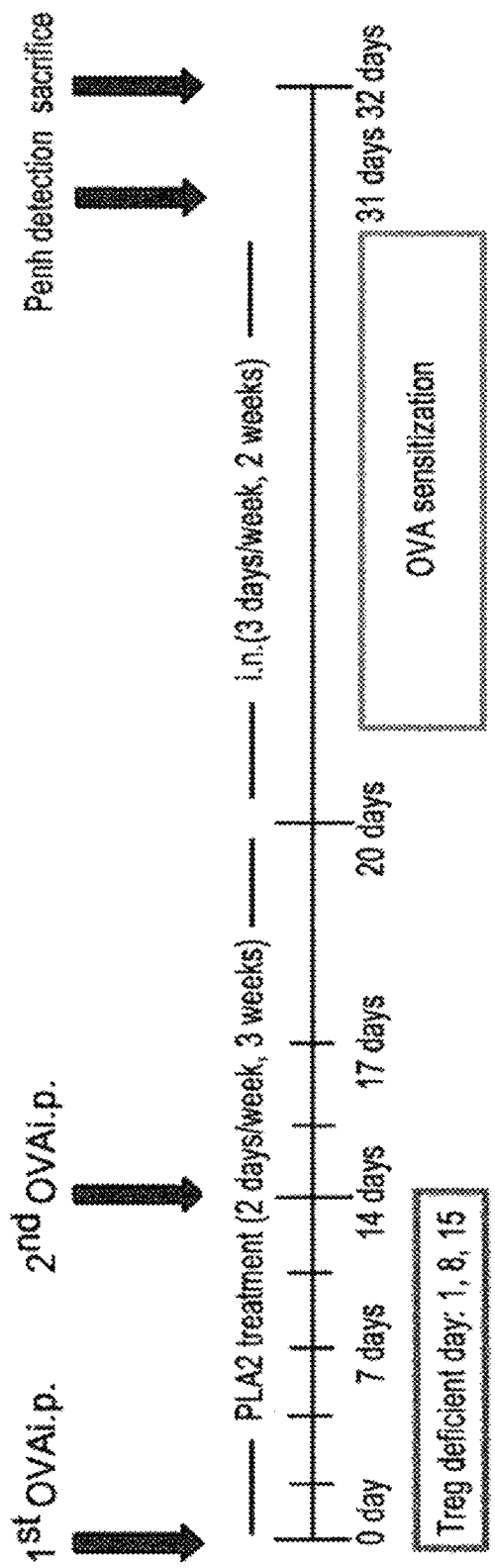
FIG. 1 is a schematic diagram briefly illustrating an experiment protocol for an allergic asthma animal model including the onset time when the experimental mice were sensitized with OVA and the time when they were treated with BV-PLA2 (secretory type).

In an aspect to accomplish the above objectives, the present invention provides a pharmaceutical composition, for treating or preventing diseases related to abnormal suppression of regulatory T cell (Treg) activity, containing a polypeptide including a BV-PLA2 amino acid sequence exclusive of a leader sequence as an active ingredient.

As used herein, the term "bee venom (BV)" refers to a mixture of acidic and basic secretions generated in the abdomen of a honey bee (*Apis mellifera*) in the form of a colorless liquid, which includes as main components peptides such as melittin, apamin, and mast cell degranulating (MCD) peptide and phospholipase A2 (PLA2), etc., and a trace amount of various components. As used herein, the term "bee venom-phospholipase A2 (BV-PLA2)" refers to phospholipase A2 among the various complex mixtures of bee venom. As used herein, the term "phospholipase A2 (PLA2) refers to an enzyme which serves the function of fatty acids via hydrolysis of glycerol at the $2^{nd}$ carbon position. It specifically recognizes an sn-2 acyl bond of phospholipids and catalyzes hydrolytic activity thereby releasing arachidonic acid and lysophospholipids. Generally, PLA is not only found in bacteria, insects or serpent venoms but also in the tissues of mammals. The BV-PLA2 of the present invention may be derived from a honey bee (*Apis mellifera*) but is not limited thereto.

BV-PLA2 may not be particularly limited as long as it has the PLA2 function derived from bee venom, and in particular, may be composed of a sequence represented by SEQ ID NO: 1. The SEQ ID NO: 1 is the total amino acid sequence that can be expressed from a gene regarding the publicly known BV-PLA2 (GenBank ID: ABQ28728.1), and is in the form of actual secretion. That is, it is the secretory type of BV-PLA2 in the form exclusive of a leader sequence at the N-terminus, and specifically, it may have an amino acid sequence represented by SEQ ID NO: 2 (consisting of 34th to 167 amino acids of SEQ ID NO: 1). As used herein, the term "leader sequence" refers to a sequence which is removed during the maturation process of from BV-PLA2 to a secretory bee venom-PLA2, and it may be a sequence corresponding to from the $1^{st}$ to $33^{rd}$ amino acids, and specifically, a sequence represented by SEQ ID NO: 3. In the present invention, the BV-PLA2 exclusive of the leader sequence is used as the same as the secretory BV-PLA2. The BV-PLA2 exclusive of the leader sequence is also called a matured type.

In the present invention, the polypeptide including a BV-PLA2 amino acid sequence exclusive of a leader sequence may be one having an additional amino acid sequence on C-terminal region and/or N-terminal region of the BV-PLA2 amino acid sequence exclusive of a leader sequence. Specifically, the polypeptide may be one having an additional amino acid sequence represented by SEQ ID NO: 4 on the N-terminal region, or one having an additional amino acid sequence represented by SEQ ID NO: 5 on the C-terminal region. More specifically, the polypeptide may be one having an amino acid sequence represented by SEQ ID NO: 6. The above additional amino acid sequences may include a tag for purifying recombinant proteins.

The polypeptide of the present invention including the bee venom-PLA2 amino acid sequence exclusive of a leader sequence, may be prepared by separating from bee venom by a known method, a recombinant expression, or may be used after purchasing those available in the market, or prepared by synthesis, but is not limited thereto.

Figure 20A:
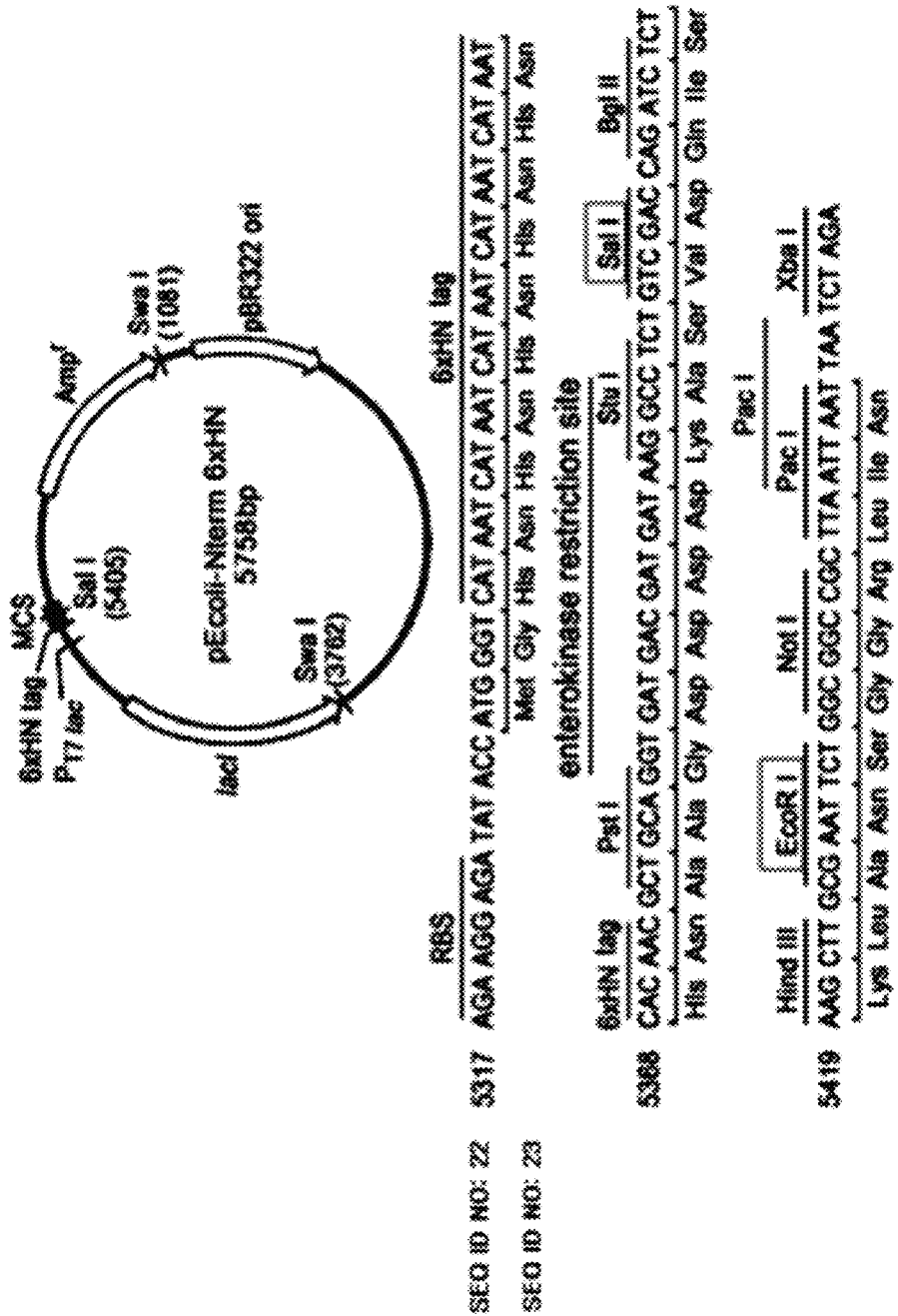
FIG. 20A-B: (A) shows a vector structure for the expression of a recombinant BV-PLA2, and (B) shows the amino acid constitutions of four types of recombinant BV-PLA2.
Figure 20B:
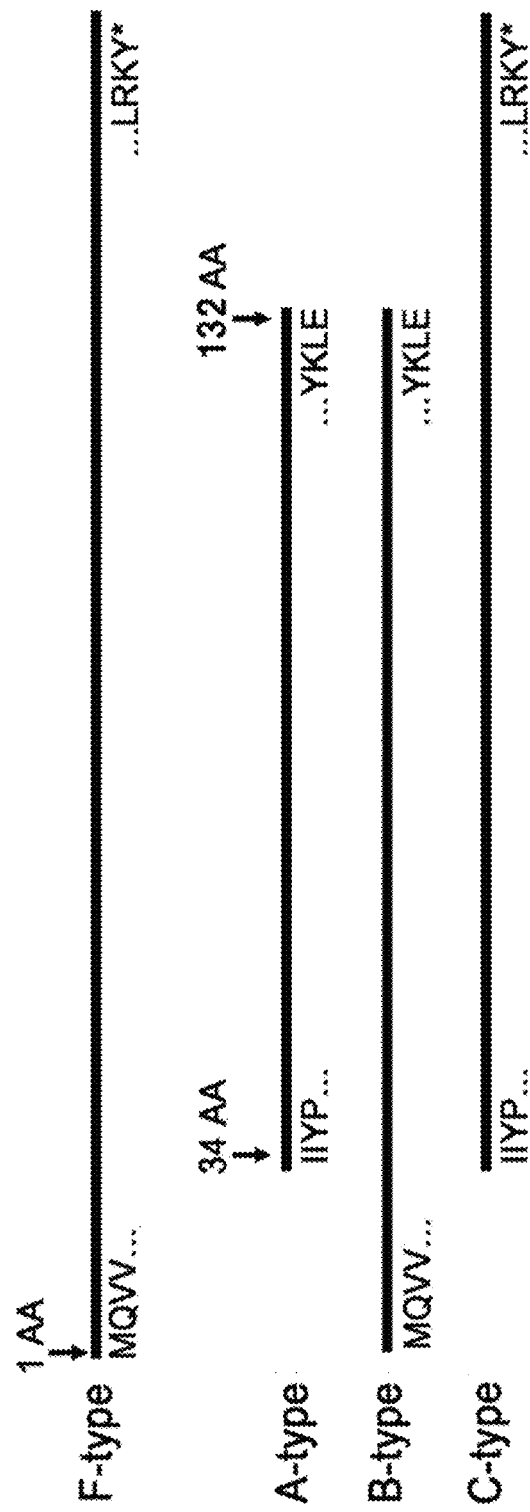
Figure 21A:
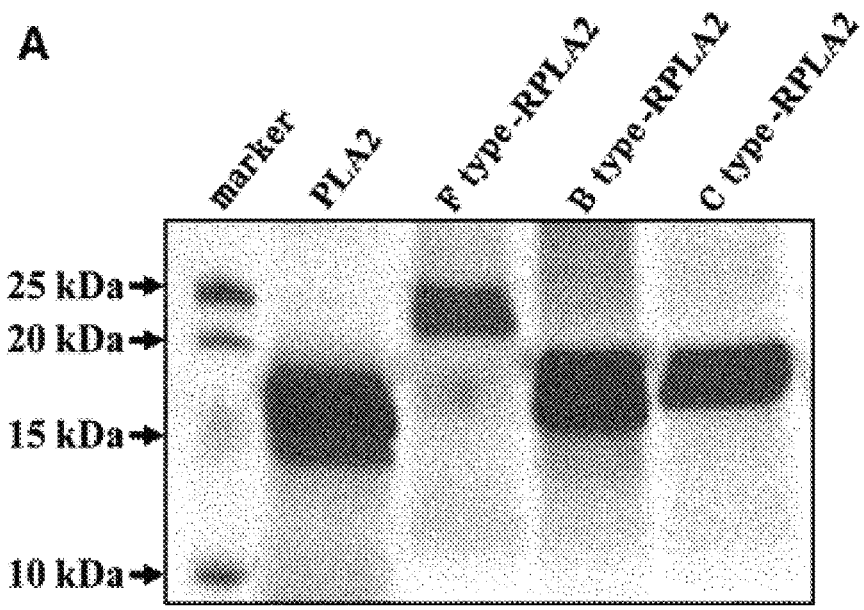
FIG. 21A-B: (A) shows an SDS-PAGE for confirmation of the recombinant proteins produced, and (B) shows the result of activity analysis for each enzyme.
Figure 21B:
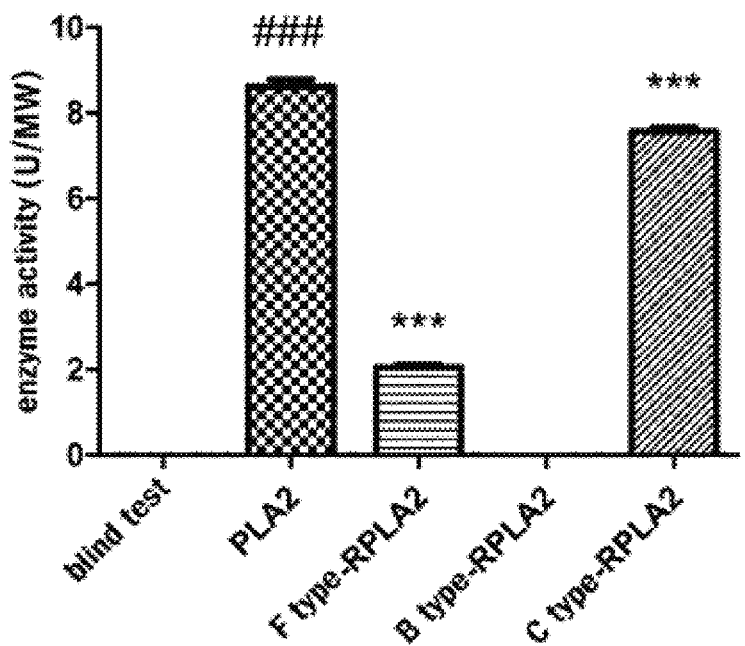
Figure 22B:
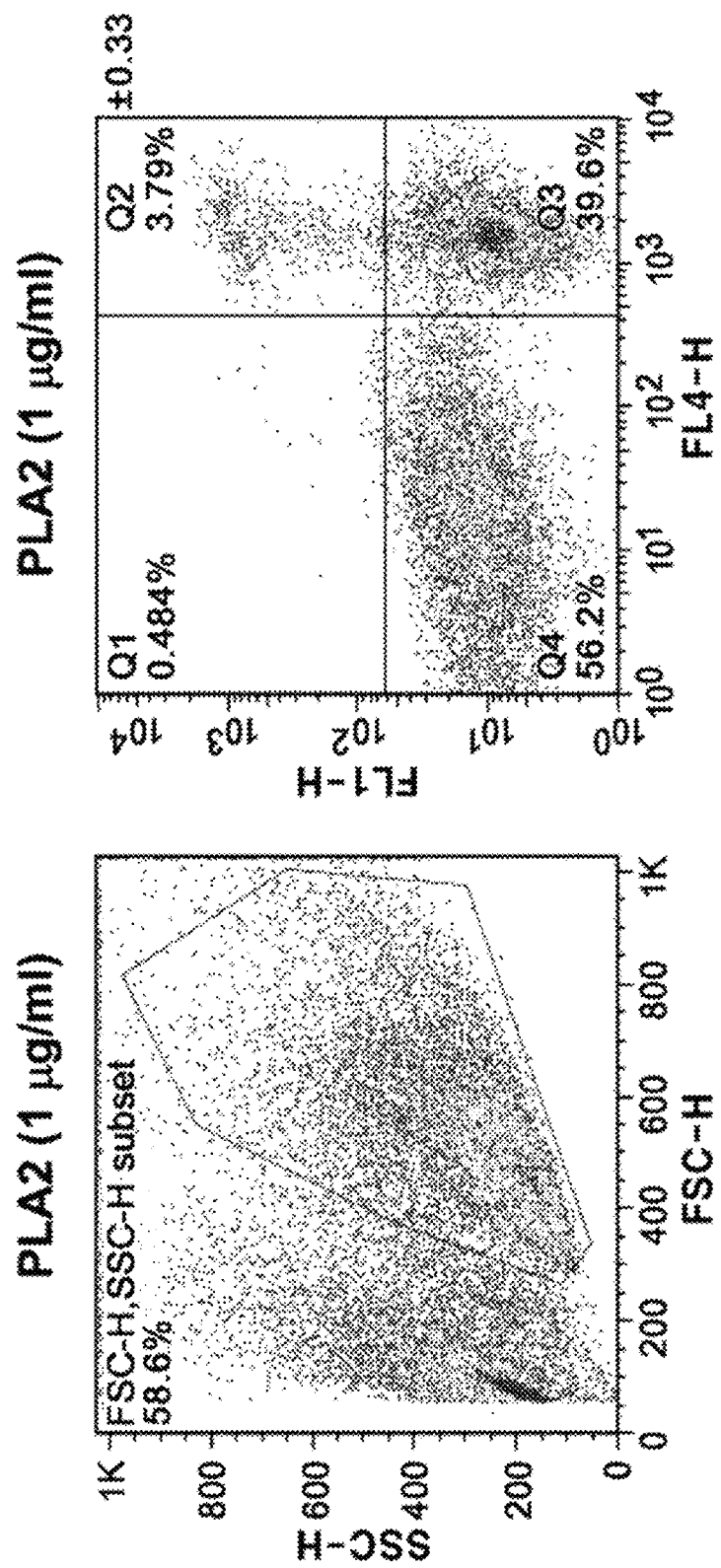
Figure 22C:
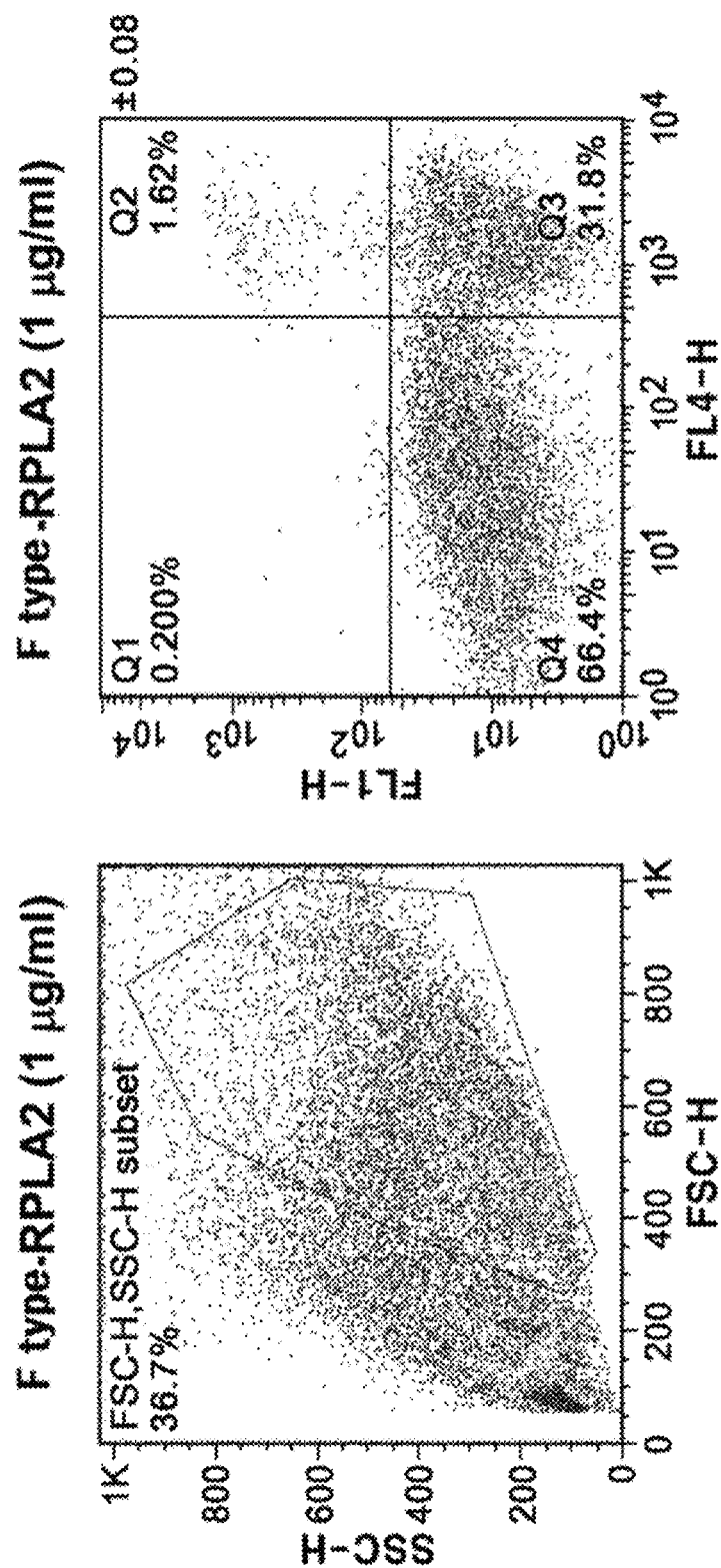
Figure 22D:
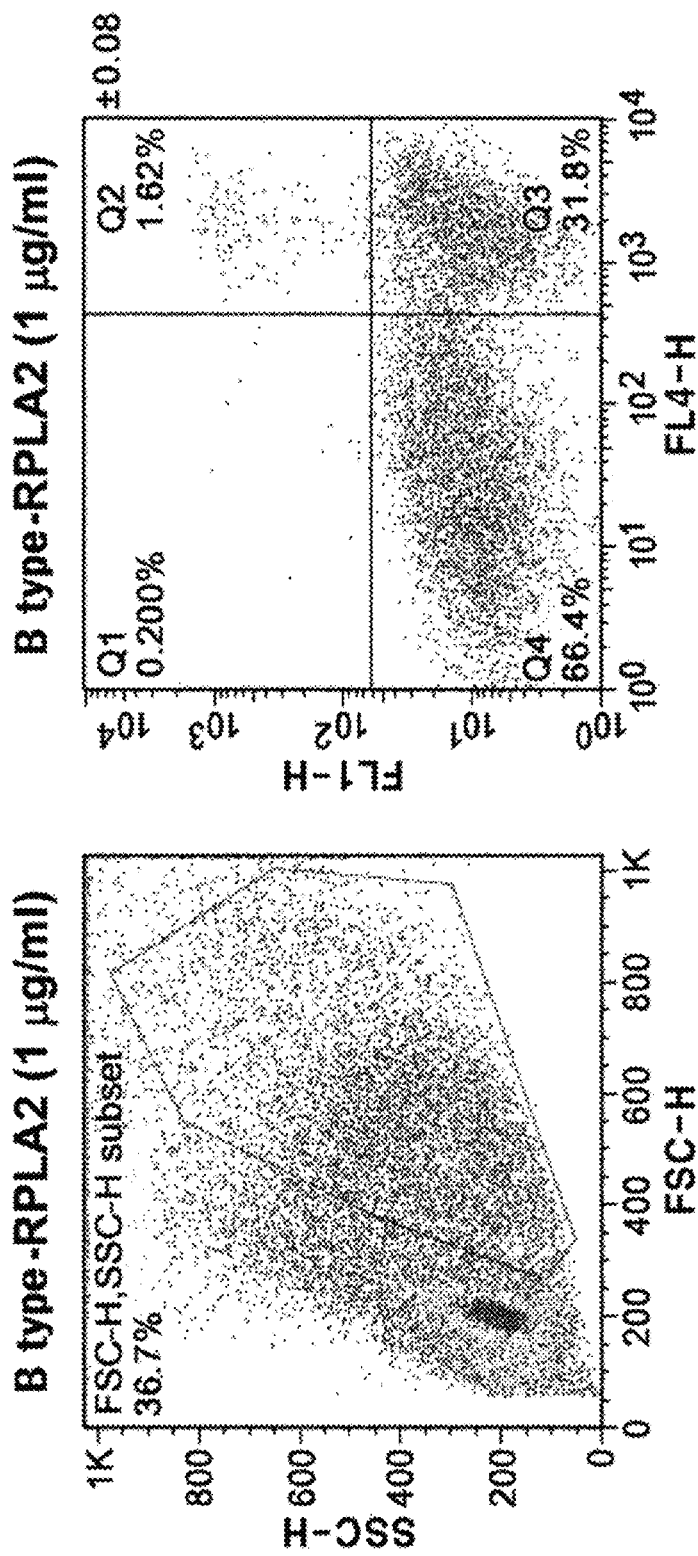
Figure 22E:
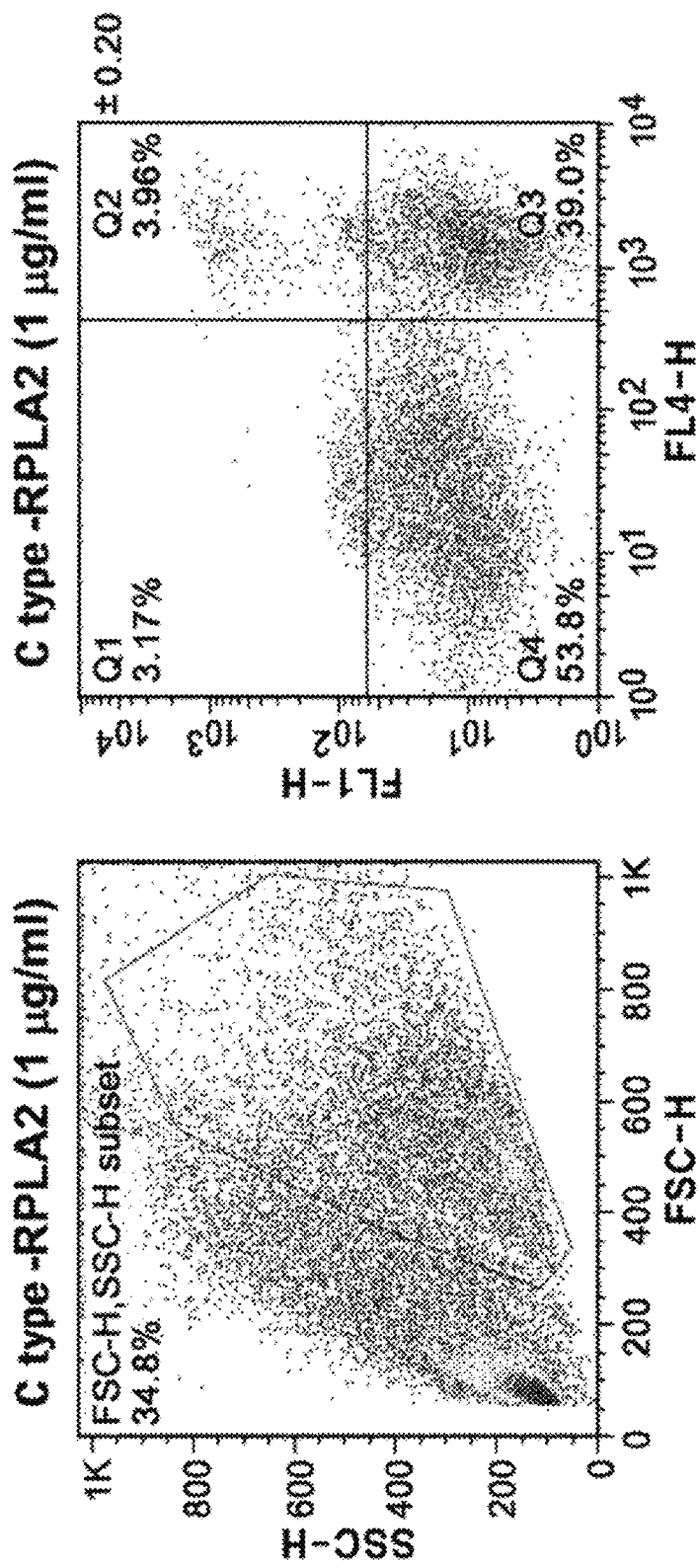
Figure 23:
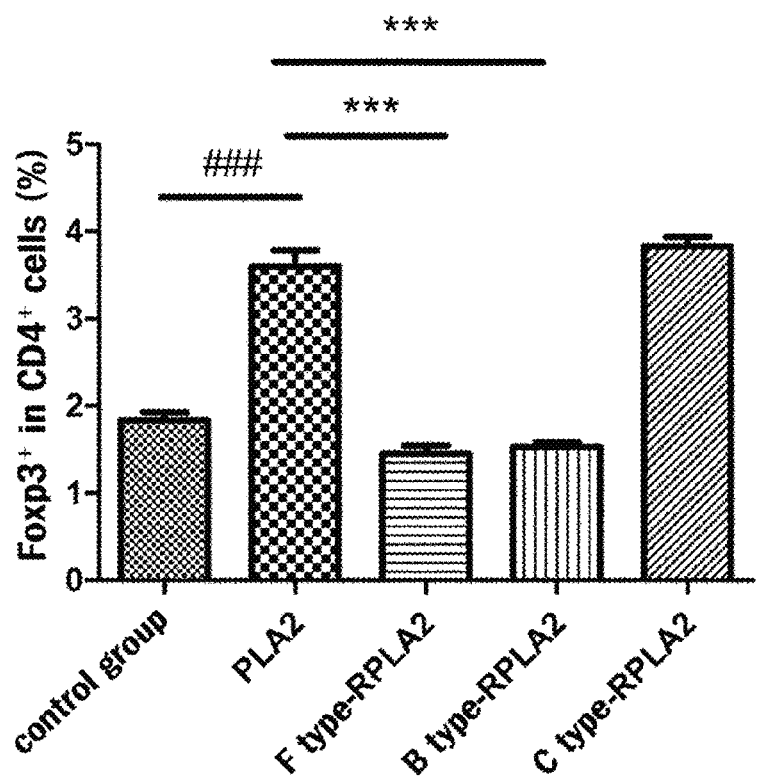
FIG. 23 is a graph showing the effects of the naturally occurring and recombinant BV-PLA2s on Foxp3+ population among the CD4$^+$ cells.

In an exemplary embodiment of the present invention, it was confirmed that a C-type recombinant BV-PLA2 (SEQ ID NO: 6; FIG. 20B), which was prepared by connecting additional amino acid residues for purification to both termini of the secretory type naturally-occurring BV-PLA2 amino acid sequence, exhibited an activity equivalent to or improved than that of the naturally-occurring BV-PLA2 (FIGS. 21B and 23). In contrast, an F-type recombinant BV-PLA2, which was prepared by including additional leader sequence to the N-terminus of the secretory type naturally-occurring BV-PLA2 amino acid sequence, or a B-type recombinant BV-PLA2, which was prepared by including additional leader sequence to the N-terminus and cutting off a part of the C-terminus (SEQ ID NOS: 7 and 8; FIG. 20B) failed to exhibit any significant enzyme activities (FIGS. 21B and 23).

The BV-PLA2 of the present invention is a protein with a molecular weight of about from 10 kDa to 18 kDa, whose constitution is different from other PLA2s derived from other biological organisms or tissues, in particular, has only 9% of sequence homology to that of human PLA2 (based on the amino acid sequence of SEQ ID NO: 2).

The BV PLA2 amino acid sequence not only includes a naturally-occurring amino acid sequence but also includes its sequence derivative (mutein) or its fragment exhibiting the BV-PLA2 activity. As used herein, the term "amino acid sequence derivative" refers to an amino acid sequence which differs from the naturally-occurring amino acid sequence by deletion, insertion, non-conservative substitution, or conservative substitution or a combination thereof by at least one amino acid residue in the naturally-occurring amino acid sequence.

In an exemplary embodiment of the present invention, it was observed that the C-type mutant (H34Q) recombinant BV-PLA2, which was prepared by substituting histidine, the $34^{th}$ amino acid from the N-terminus of the secretory naturally-occurring BV-PLA2, into glutamine, showed a drastic decrease in its activity (FIGS. 24 and 25). Accordingly, it is preferred that at least histidine, the $34^{th}$ amino acid, be included as an essential component for enzyme activity.

In the present invention, its fragment exhibiting the BV-PLA2 activity may have an amino acid sequence of SEQ ID NO: 9. A polypeptide including an amino acid sequence of a BV-PLA2 fragment exclusive of a leader sequence may be a polypeptide which further includes an additional amino acid sequence to the C-terminus or N-terminus of the amino acid sequence of BV-PLA2 fragment exclusive of a leader sequence. Specifically, it may be a polypeptide additionally including an amino acid sequence of SEQ ID NO: 4 to an N-terminus region, and a polypeptide additionally including an amino acid sequence of SEQ ID NO: 5 to a C-terminus region. More specifically, it may be a polypeptide including an amino acid sequence of SEQ ID NO: 10. The above additional amino acid sequence may include a tag for the purification of recombinant proteins.

The substitution of amino acids in proteins or peptides without modifying the entire molecular activity is already known in the art (H. Neurath and R L. Hill, The Proteins, Academic Press, New York, 1979). The most conventional substitution is the substitution between amino acid residues of Ala/Ser, Val/Ile, Asp/Glu, Thr/Ser, Ala/Gly, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly. Depending on the situations, the substitution may be modified via phosphorylation, sulfation, acrylation, glycosylation, methylation, farnesylation, acetylation, amidation, etc.

The above described sequence derivatives may be those which exhibit the same biological activity to BV-PLA2 of the present invention or have an improved structural stability regarding heat, pH, etc.

As used herein, the term "regulatory T cell (Treg)" refers to a kind of helper T cells (Th) also called suppressor T cells. Unlike other helper T cells exhibiting a humoral immune promoting effect by accelerating differentiation and activation of other leucocytes, Treg maintains immune tolerance by inhibiting immunity thereby enabling homeostasis. Treg can be divided into adaptive Treg, which includes Tr1 and Th3 cells produced during normal immune responses, and naturally-occurring Treg. The naturally-occurring Treg is generated in thymus, has positive to phenotypes for CD4, CD25 and Foxp3, and is distinguished from other T cells due to the presence of Foxp3, an intracellular molecule.

As used herein, the term "diseases related to abnormal suppression of Treg activity" refers to a disease that occurs when the activity of regulatory T cells, which performs the functions of inhibition of autoimmunity, immune tolerance, inhibition of tissue damage by inflammation, etc., becomes abnormally deteriorated, and it includes allergic diseases, autoimmune diseases and neurodegenerative diseases, but is not limited thereto.

The distinction between self and non-self antigens is the most important issue in the field of immunology, and due to the studies for the past few decades, various mechanisms involved in central tolerance and peripheral tolerance maintaining unresponsiveness to self antigens have been identified. In addition to the mechanisms of clonal deletion and anergy (functional inactivation), the suppression of the activity of self-reactive T cells has been also considered as an important mechanism in maintaining the tolerance for self-antigens.

Among them, $CD4^+CD25^+$ T cells, known as naturally-occurring Tregs, have been confirmed to be important for the tolerance and prevention of autoimmune diseases by the experimental result that they can induce various kinds of autoimmune diseases in mice where $CD25^+$ cell deficient T cells or $CD25^-$ T cells were introduced via adoptive transfer (S. Sakaguchi, Annu. Rev. Immunol., 2004, 22: 531-562), before the discovery that foxp3 is an essential regulator gene important for Treg cell induction.

It is known that foxp3 mutants can induce X-linked immunodeficiency syndrome (IPEX), which directly induces autoimmune diseases (type I diabetes, thyroiditis, etc.) from many organs in the endocrine system in humans (C. L. Bennett et al., Nat. Genet., 2001, 27: 20-21; R S. Wildin et al., Nat. Genet., 2001, 27: 18-20). This suggests the importance of CD4$^+$CD25$^+$Foxp3$^+$ regulatory T cells in tolerance and for the prevention of autoimmune diseases.

In addition to IPEX, the deficiency in Tregs or the loss of their suppressive function have been found to be associated with the pathogenic mechanism of autoimmune diseases such as type I diabetes, rheumatoid arthritis, multiple sclerosis, and psoriasis (M. Miyara et al., J. Immunol., 2005, 175: 8392-8400).

Attempts have been made to use self antigen-specific Tregs for the treatment of autoimmune diseases and prevention of graft rejection. These attempts are mostly in the form of a somatic cell therapy, wherein the amplification of self antigen-specific Tregs is induced in vivo as in the case of peptide therapeutic vaccination using altered peptide ligand (APL) or administered after in vitro amplification, and are methods that inhibit the functions of effector T cells, which are specific to self antigens that induce autoimmunity (Y. Belkaid and B. T. Rouse, Nat. Immunol., 2005, 6: 353-360).

Although pathogen-specific Tregs have a negative impact on the elimination of pathogens they serve an important role in the regulation of immunopathology by inhibiting tissue damage due to inflammation induced by pathogens, as in the prevention of autoimmune diseases (Y Belkaid and B. T. Rouse, Nat. Immunol., 2005, 6: 353-360).

For example, in an experiment using mice infected with HSV through foodpads, deficiency in CD4$^+$CD25$^+$ T cells improved virus elimination by increasing CD8 but it aggravated T cell-mediated lesions (S. Suvas et al., J. Exp. Med., 2003, 198: 889-901).

This has become an important issue to consider when conducting a therapeutic vaccination for the treatment of chronic virus infections including HIV and HCV by targeting Tregs such as removal of naturally-occurring T cells or blocking of effector molecules (Y Belkaid and B. T. Rouse, Nat. Immunol., 2005, 6: 353-360).

Figure 8A:
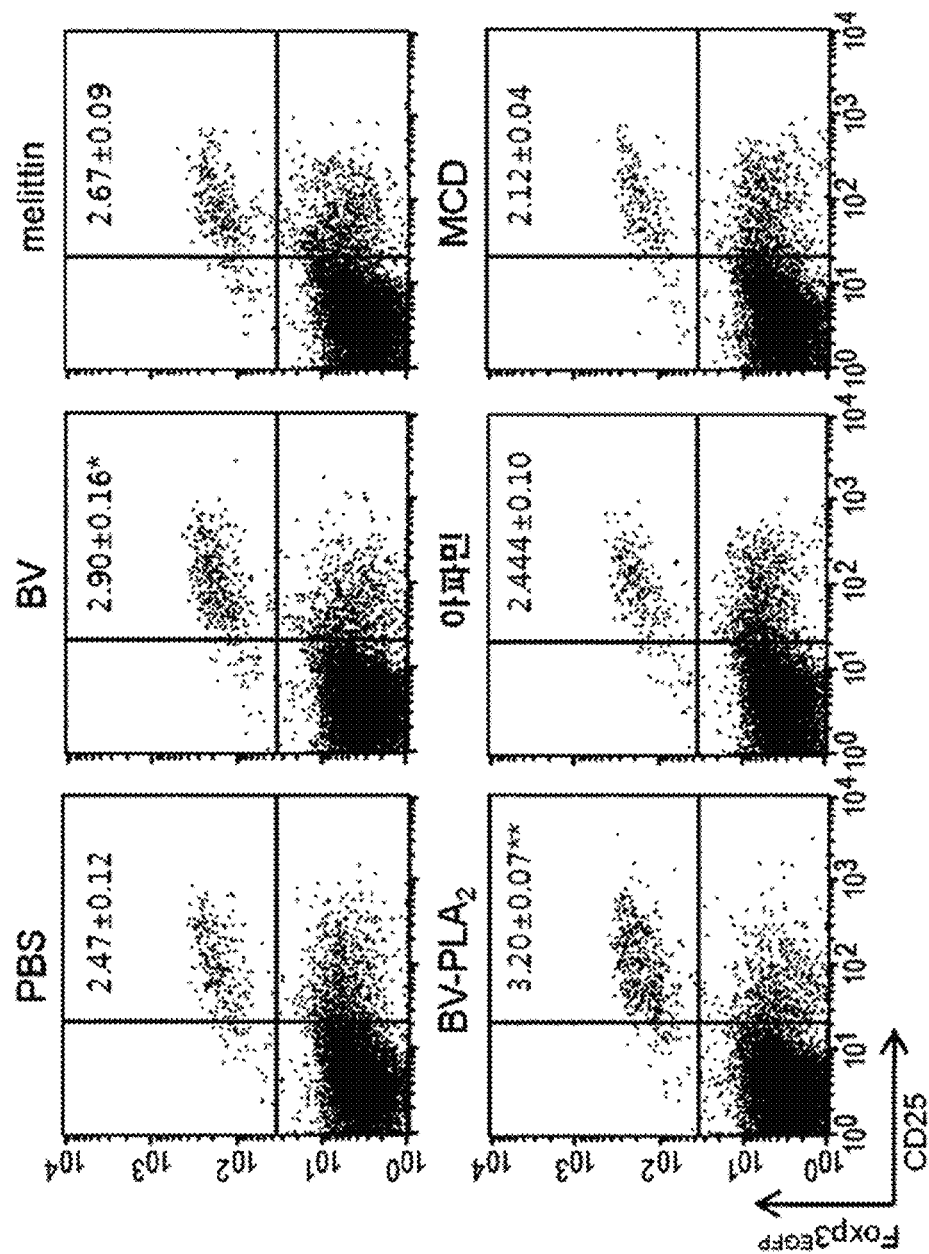
FIG. 8A-B shows the comparative results of various bee venom components on immune-regulation inducing effect. The splenocytes of the Foxp3$^{EGFP}$ C57BL/6 mice were treated with bee venom or its component(s) for 24 hours, stained with anti-CD4 and anti-CD25 antibodies, and then analyzed via flow cytometry (A). The CD4$^+$ T cells were gated, and CD25 and Foxp3 positive cells were analyzed. The numbers within the dot plots represent the percentage of cells belonging to the corresponding quadrant (B). The data is indicated via mean±SEM (*p<0.05, **p<0.01 vs. a PBS-treated group).
Figure 8B:
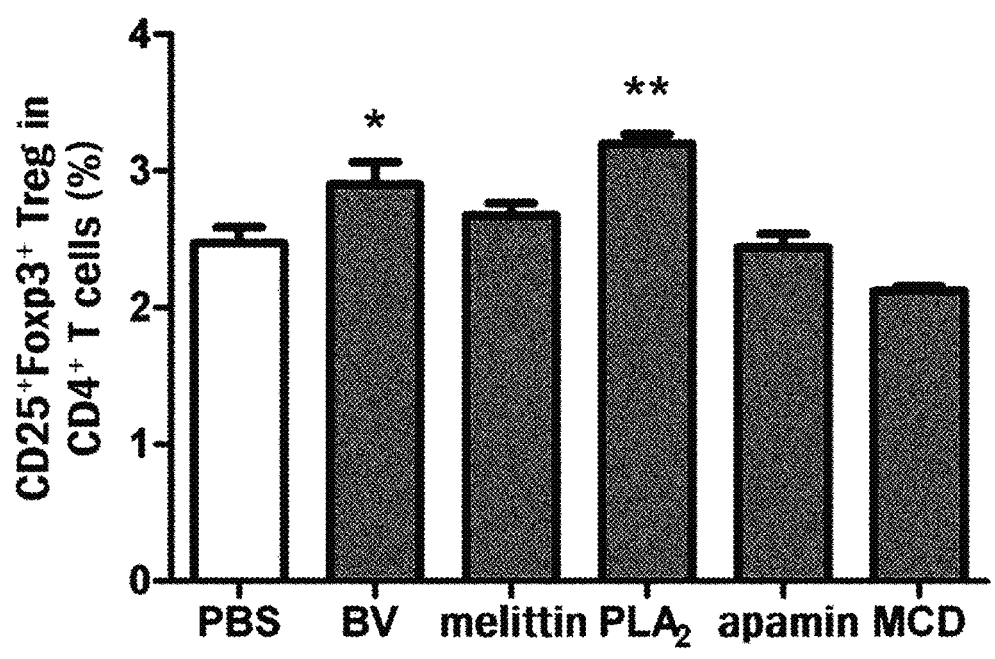
Figure 9A:
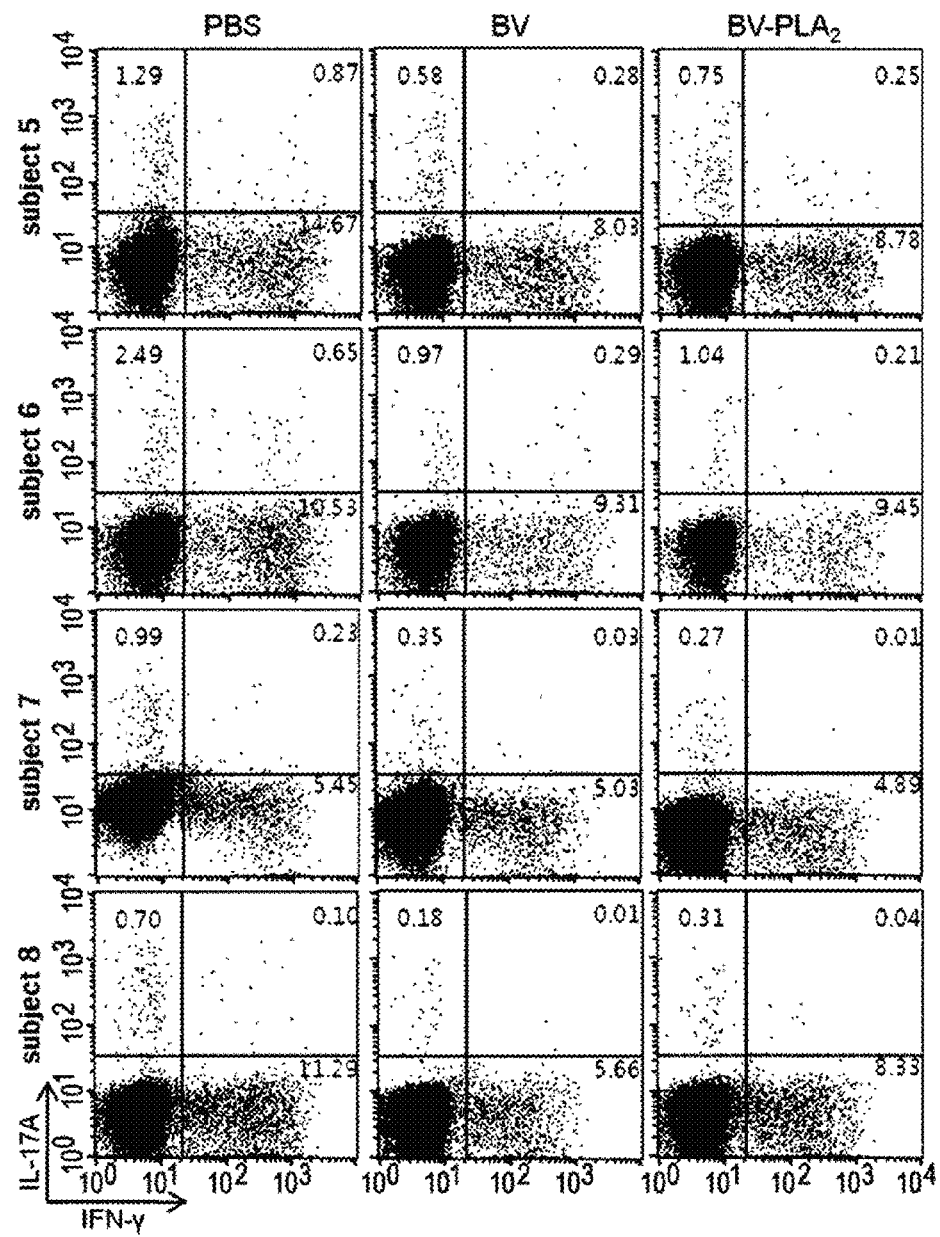
FIG. 9A-B shows the results of immune-regulation induced by human secretory BV-PLA2 (bee venom-phospholipase A2; secretory bee venom-PLA2). Human PBMC was re-stimulated with anti-CD3/28 antibodies and bee venom or BV-PLA2 for 24 hours. Then, the cells were re-stimulated with PMA (50 ng/ml) and ionomycin (1 µg/ml) for 5 hours in the presence of monensin. the CD4$^+$ T cells were gated, and Th1/Th17 was analyzed (A). The numbers within the to dot plots represent the percentage of cells belonging to the corresponding quadrant (B).
Figure 9B:
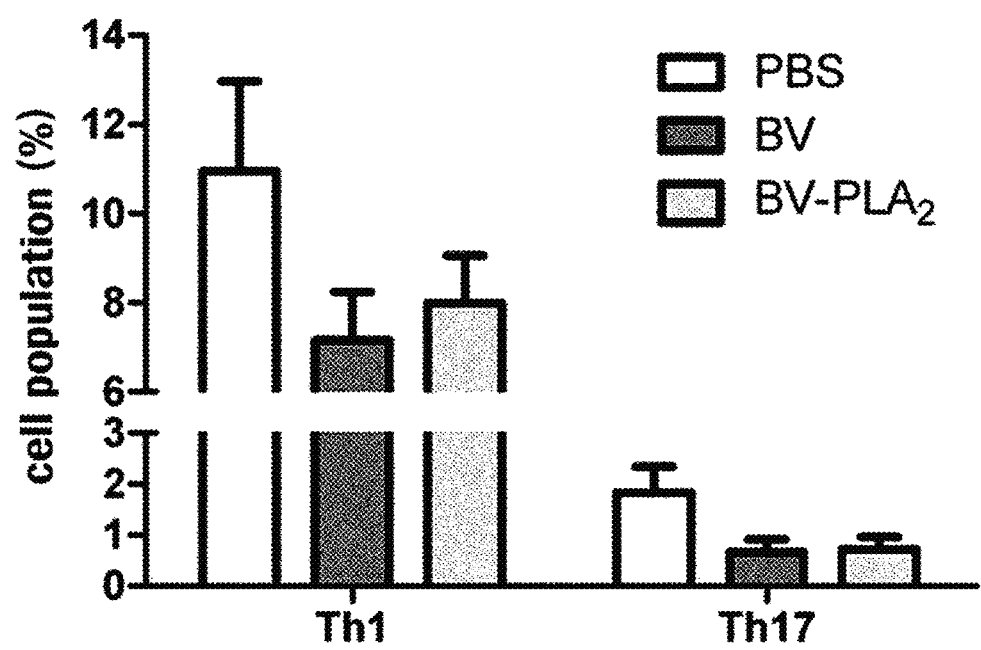

As used herein, the term "autoimmune diseases" may include diseases that destroy self materials by wrongly determining self materials as foreign materials due to the inability to distinguish self materials from materials introduced from outside, which is the most important step in immune responses in the course of a series of actions for protecting self by destroying or inactivating materials introduced from outside. For example, they made include rheumatoid arthritis, systemic sclerosis, insulin-dependent juvenile diabetes by pancreatic islet cell antibody, alopecia areata, psoriasis, pemphigus, asthma, aphthous stomatitis, chronic thyroiditis, partial acquired aplastic anemia, primary liver cirrhosis, ulcerative colitis, Behcet's disease, Crohn's disease, silicosis, asbestosis, IgA nephropathy, poststreptococcal glomerulonephritis, Sjogren syndrome, Guillian Barre syndrome, dermatomyositis, polymyositis, multiple sclerosis, autoimmune hemolytic anemia, autoimmune encephalomyelitis, myasthenia gravis, Graves disease, polyarteritis nodosa, ankylosing spondylitis, fibromyalgia, temporal arteritis, Wilson's disease, Fanconi syndrome, multiple myeloma, and systemic lupus erythematosus, but is not limited thereto. The above autoimmune disease may be multiple sclerosis or autoimmune encephalomyelitis In an exemplary embodiment of the present invention, it was observed that bee venom inhibited the differentiation of Th1/Th17 thereby alleviating experimental autoimmune encephalomyelitis (EAE) (FIG. 5) while increasing the expression of Foxp3 in CD4$^+$CD25$^+$Foxp3$^+$ Treg and CD4$^+$CD25$^+$ Treg, which are regulatory T cells (FIG. 2) involved in immunities. Additionally, it was confirmed that Treg-deficiency can block the EAE alleviating effect of bee venom (FIG. 6), and thus suggested that Treg acts as an important mediator of EAE alleviation by bee venom. Accordingly, the increase of CD4$^+$CD25$^+$Foxp3$^+$ Treg and decrease of Th1/Th17 by bee venom in human CD4$^+$ T cells were confirmed thereby verifying the immune regulation effect of bee venom in humans. Additionally, upon measurement of immune regulation inducing effects of various bee venom components, PLA2 (secretory type) was shown to have the highest immune regulation effect among the bee venom components (FIG. 8), and by its application in human cells, it was confirmed to enable induction of immune regulation in humans (FIG. 9).

As used herein, the term "allergic diseases" refers to diseases, wherein substances which are non-toxic to normal people cause various symptoms in particular people due to abnormalities in their systems. The substances causing the allergic diseases are called allergens or antigens, and pollens, antibiotics, drugs, dusts, foods, cold air or sunlight, etc., may induce allergies. Examples of the allergic diseases include hives, sneezing, rhinorrhea, coughs, hay fever, ocular hyperemia, eczema, rashes, etc. The symptoms of the allergic diseases are hives, sneezing, pruritus, rhinorrhea, coughs, hay fever, ocular hyperemia, eczema, rashes, etc. The allergic diseases may include asthma, atopic dermatitis, conjunctivitis, rhinitis, and ulcerative colitis, but is not limited thereto. Preferably, the allergic disease is asthma, which accompanies symptoms such as airway constriction, increase in the secretion of mucus liquid in the lungs, dyspnea, and coughs.

Figure 18:
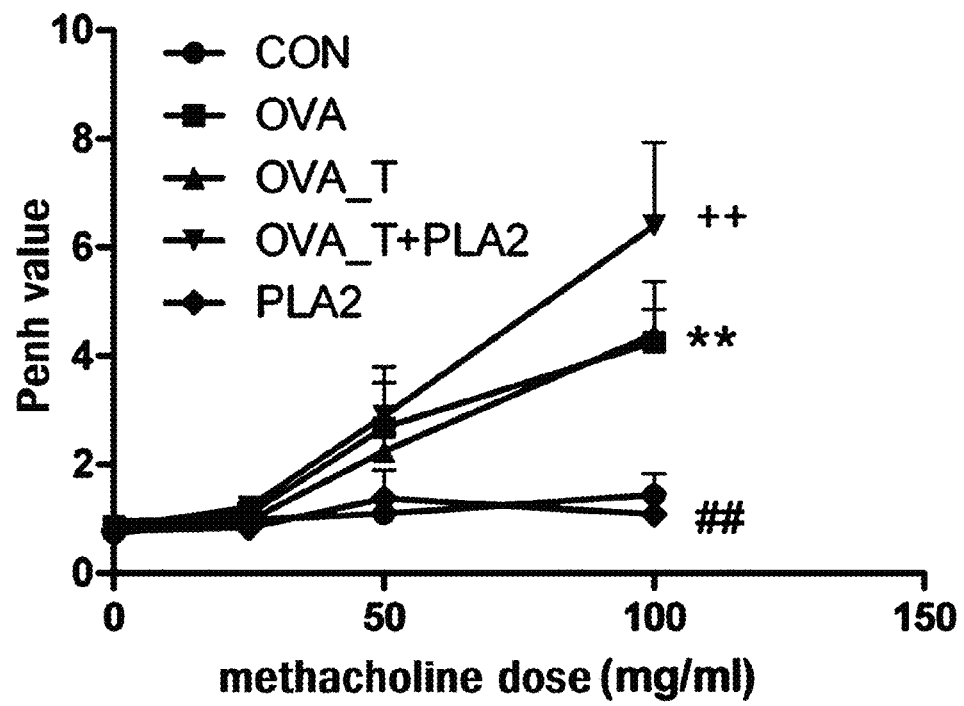
FIG. 18 shows a graph illustrating the effect of BV-PLA2 (secretory type) on the hyperresponsiveness in an OVA-induced asthmatic mouse model. The OVA-induced asthmatic mice had high $P_{enh}$ value at 50 and 100 mg/ml concentrations of methacholine ($*p<0.01$ vs. CON). The group (OVA+PLA2) show a significant decrease in the $P_{enh}$ value at 100 mg/ml concentration of methacholine used in the OVA-induced mice (regarding OVA, $**p<0.01$ vs. PLA2).

In an exemplary embodiment of the present invention, when an OVA-induced asthma mouse model, where the asthma was induced by sensitization with ovalbumin (OVA), was treated with BV-PLA2 there was a significant increase in CD4$^+$CD25$^+$Foxp3$^+$ Treg compared to the control group and other experimental groups (FIG. 12), thus confirming that BV-PLA2 has an excellent inhibitory effect against the introduction of inflammatory cells into lung tissues increased due to OVA sensitization (FIG. 16). Additionally, it also showed an effect of alleviating the airway hyperresponsiveness (AHR) (FIG. 18).

As used herein, the term "neurodegenerative diseases" refers to diseases associated with symptoms such as degeneration, loss of functions, and often apoptosis of neurons. Since these symptoms are mostly progressive they are often highly destructive and patients with neurodegenerative diseases may experience extreme deterioration in their cognitive or motor performance. The neurodegenerative diseases may include, although not particularly limited thereto, Parkinson's disease (PD), Alzheimer's disease (AD), amyotrophic lateral sclerosis (ALS), Huntington's disease (HD), fronto-temporal dementia, cortico basal degeneration, and progressive to supranuclear palsy (PSP).

In an exemplary embodiment of the present invention, it was confirmed that BV-PLA2 (secretory type) decreases dopaminergic (DA) neuronal death in substantia nigra (SN) of a 1-methyl-4-phenyl-1,2,3,6-tetrahydropyridine (MPTP)-addicted mouse, i.e., an animal model with Parkinson's disease (FIG. 19).

As used herein, the term "prevention" refers to all kinds of activities of inhibiting diseases related to abnormal suppression of regulatory T cell activity or delaying their occurrence by administering a pharmaceutical composition of the present invention, and the term "treatment" refers to all kinds of activities of improving or advantageously modifying the symptoms of the diseases related to abnormal suppression of regulatory T cell activity by administering the pharmaceutical composition of the present invention.

The pharmaceutical composition of the present invention may further include a pharmaceutically acceptable carrier. As used herein, the term "pharmaceutically acceptable" refers to a non-toxic property to cells or humans being exposed to the composition. The above carrier to be used may be any one known in the art such as a buffering agent, a preservative, a pain-relieving agent, a solubilizing agent, an isotonic agent, a stabilizing agent, a base, an excipient, a lubricant, etc., without any limitation. The carrier, excipient, and diluent that may be included in the pharmaceutical composition of the present invention are lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and base oil. For the preparation of formulations, the conventionally used filler, extender, binder, humectants, disintegrating agent, surfactant, diluent or excipient may be used. Examples of the usable typical surfactant that mediates the transmembrane transport are those derived from steroids, cationic lipids such as N-[1-(2,3-dioleoyl)propyl-N,N,N-trimethylammonium chloride] (DOTMA), or cholesterol hemisuccinate.

In another aspect of the present invention, there is provided a method for preventing or treating diseases related to abnormal suppression of regulatory T cell activity including administering the above pharmaceutical composition to a subject in need thereof.

As used herein, the term "subject" refers to all kinds of animals including humans in which diseases related to abnormal suppression of regulatory T cell activity have occurred or may occur, and the diseases related to abnormal suppression of regulatory T cell activity can be effectively prevented or treated by administering the pharmaceutical composition of the present invention to the subject. The pharmaceutical composition of the present invention may be administered in combination with a conventional therapeutic agent for the diseases related to abnormal suppression of regulatory T cell activity.

As used herein, the term "administration" refers to an introduction of a particular material to a subject by a suitable method, and the above composition may be administered via any conventional administration route as long as they can allow the composition to arrive at the target tissue. For example, intraperitoneal administration, intravenous administration, intramuscular administration, intradermal administration, oral administration, topical administration, intranasal administration, intranasal administration, intrapulmonary administration, and intrarectal administration, but is not limited thereto. Solid formulations for oral administration may include tablets, pills, powders, granules, capsules, etc., and these solid formulations are prepared by adding at least one excipient in addition to the composition, for example, starch, calcium carbonate, sucrose, or lactose, gelatin, etc. Additionally, a lubricant such as magnesium stearate, and talc may be used, in addition to a simple excipient. Examples of liquid formulations for oral administration may include suspensions, medicines for internal use, emulsifiers, syrups, etc., and in addition to the frequently used simple diluents such as water and liquid paraffin, various excipients, for example, humectants, sweeteners, fragrant, preservatives, etc., may be included. However, peptides can be easily digested if administered orally, and thus a composition for oral administration is preferred to be formulated in such a manner that the active drug component is coated or protected from decomposition in the stomach. Formulations for parenteral administration may include sterile aqueous solutions, nonaqueous solvents, suspensions, emulsifiers, lyophilized preparations, suppositories. Examples of the nonaqueous solvents and suspensions include propylene glycol, polyethylene glycol, a vegetable oil such as olive oil, an injectable ester such as ethyl oleate. Examples of a base for the suppositories include witepsol, macrogol, Tween 61, cacao butter, laurinum, glycerogelatin, etc. For the improvement of stability or absorptivity of peptides, carbohydrates such as glucose, sucrose, and dextran; antioxidants such as ascorbic acid and glutathione; chelating materials, low molecular weight proteins or other stabilizers may be used.

Additionally, the pharmaceutical composition of the present invention may be administered by any device which enables an active ingredient to move to a target cell. Preferable administration routes and formulations include those for intravenous injection, subcutaneous injection, intradermal injection, intramuscular injection, intravenous infusion, etc. Injections may be prepared using an aqueous solvent such as saline, ringer solution, etc.; a non-aqueous solvent such as a vegetable oil, high grade fatty acid eser (e.g., oleic acid ethyl, etc.), alcohols (e.g., ethanol, benzyl alcohol, propylene glycol, glycerin, etc.), etc., and may include a pharmaceutically acceptable carrier such as a stabilizer for preventing deterioration (e.g., ascorbic acid, sodium bisulfite, sodium pyrosulfite, BHA, tocopherol, EDTA, etc.), an emulsifier, a buffer for pH adjustment, a preservative for preventing microbial growth (e.g., phenylmercuric nitrate, thimerosal, benzalkonium chloride, phenol, cresol, benzyl alcohol, etc.).

Meanwhile, the pharmaceutical composition of the present invention is administered in a pharmaceutically effective amount. As used herein, the term "pharmaceutically effective amount" refers to an amount sufficient for the treatment of diseases at a reasonable benefit/risk ratio applicable to a medical treatment without causing any adverse effects, and the level of an effective dose may be easily determined by a skilled person in the art according to factors including sex, age, body weight, health status of a patient, type of disease(s), severity of illness, drug activities, drug sensitivity, route and duration of administration, release rate, treatment period, mixing of drugs or other drug(s) used in combination, and others well known in the medical field. In general, an active ingredient may be administered daily in the amount of about from 0.01 mg/kg/day to 1000 mg/kg/day. For oral administration, it may be appropriate to administer in the amount of from 50 to 500 mg/kg, and may be administered at least once daily.

MODE FOR INVENTION

Hereinafter, the present invention will be described in more detail with reference to the following examples. However, the following examples are provided for illustrative purposes only, and the scope of the present invention should not be limited thereto in any manner.

Example 1: Preparation of Experimental Animals

Seven to eight-week old female C57BL/6 mice with a body weight of from 18 g to 23 g were purchased from Charles River Korea (Sungnam, Korea). Foxp3$^{EGFP}$C57BL/6 (C. Cg-Foxp3tm2Tch/J) mice were purchased from Jackson Laboratory (Bar Harbor, Me., USA) and seven to eight week old male C57BL/6J mice with a body weight of from 21 g to 22 g were purchased from Charles River Breeding Laboratory (Yokohama, Japan). All mice were stored under aseptic conditions provided with air conditioning and 12 hour light/dark cycles. Additionally, all mice were given ad libitum access to food and water during the experiment. This study was approved by Animal Experimentation Ethics Committee of Kyung Hee University (Korea).

1.1. Experimental Autoimmune Encephalomyelitis (EAE)-Induced Experimental Animal Model Murine MOG$_{35-55}$ (M-E-V-G-W-Y-R-S-P-F-S-R-V-V-H-L-Y-R-N-G-K) (SEQ ID NO:24) peptides were purchased from Peptron Inc. (Daejeon, Korea). The peptides were purified via HPLC to ensure 95% or higher of purity. For EAE induction, 200 μg of MOG$_{35-55}$ peptides, which was dissolved in CFA (Sigma-Aldrich, St. Louis, Mo., USA) containing 100 μg of *Mycobacterium tuberculosis*, were administered to the hind flanks of mice via subcutaneous injection, and further administered with 400 ng of pertussis toxin (Sigma-Aldrich, St. Louis, Mo., USA) via intraperitoneal injection on day 0 and day 2. The mice were examined daily to check the presence of clinical signs of any disease(s), and the results were scaled in the range of from 0 to 5 at 0.5 intervals; wherein 0 denotes no clinical sign, 1 denotes relaxed tails, 2 denotes weakened hind legs or abnormal gait, 3 denotes complete paralysis of hind legs, 4 denotes complete paralysis of hind legs accompanying weakened front legs or paralysis of front legs, and 5 denotes being in a moribund state or death.

1.2. Allergic Asthma Experimental Animal Model

Six to eight-week old female Foxp3$^{+EGFP}$ Balb/c mice were prepared. The mice on day 0 were divided into a negative control group (PBS-treatment; CON) (n=4) and an OVA-induced asthma group. The OVA-induced asthma group was subdivided into four groups (OVA-test-infected mice with PBS treatment (OVA); OVA-test-infected mice with BV-PLA2 (0.2 mg/kg) treatment (OVA+PLA2); OVA and anti-CD25 antibody-test-infected mice with BV-PLA2 (0.2 mg/kg) treatment (OVA-T+PLA2); and OVA and anti-CD25 antibody-test-infected mice (OVA-T), n=4/group). Briefly, the mice were sensitized via intraperitoneal (ip) injection of 100 μg of ovalbumin (OVA; Sigma-Aldrich, St. Louis, Mo., USA), which was precipitated with 20 mg aluminum hydroxide in 100 μl of PBS on day 0 and day 14. The mice were test-infected by directly administering 1% OVA in 50 μl of PBS through their nostrils using a micropipette through a total of 6 administrations from day 20 to day 30. The mice in the negative control group were sensitized with PBS alone and test-infected.

Treg-deficient mice were intraperitoneally injected with 0.25 mg anti-CD25 antibodies via on days 1, 8 and 15. Anti-mouse CD25 rat IgG1 (anti-CD25; clone PC61) was internally manufactured from hybridomas obtained from American Type Culture Collection (Manassas, Va., USA). The efficacy of Treg-deficiency as confirmed via flow cytometry analysis using PE-anti-mouse CD25 and fluorescein isothiocyanate (FITC)-anti-mouse CD4. The mice in the PLA2-test infected group were intraperitoneally injected with PLA2 at a concentration of 0.2 mg/kg through a total of 6 injections from day 3 to day 17. On day 31, airway hyperresponsiveness (AHR) was analyzed via (non-invasive) lung function measurement (All Medicus, Seoul, Korea), and on day 32 mice were sacrificed and various tissues were collected therefrom for analyses (FIG. 1).

1.3. 1-methyl-4-phenyl-1,2,3,6-tetrahydropyridine (MPTP)-Addicted Parkinson's Disease Experimental Animal Model Seven to eight-week old male C57BL/6 mice with a body weight of from 21 g to 22 g (Charles River Breeding Laboratory, Yokohama, Japan) were prepared. For the construction of an MPTP-addicted model, the mice were intraperitoneally injected with an MPTP-HCl (a free base brine at 20 mg/kg; Sigma-Aldrich, St. Louis, Mo., USA) four times at two hour intervals. Twelve hours after the final MPTP injection, the MPTP-addicted mice were intraperitoneally injected with BV-PLA2 (0.5 mg/kg) once daily for six days. Some of the mice used as a control group were injected with BV-PLA2 alone or a vehicle. For Treg deficiency purpose, some of the mice were intraperitoneally injected with anti-CD25 antibodies (1 mg/kg) or normal rat IgG (1 mg/kg) once one day prior to the administration of MPTP Example 2: Separation of Human Peripheral Blood Mononuclear Cells (PBMC)

Human PBMC was separated from a healthy donor's blood collected using a BD VACUTAINER® CPT tube containing heparin sodium. Briefly, the blood was directly collected into the tube via venipuncture and centrifuged at 1600 g for 20 minutes. The cells located on the upper portion of the centrifuged gel were recovered using a pipette and washed twice with PBS. The present invention was approved by the Institutional Review Board (IRB) of Korean Medicine Center of Kyung Hee University (Korea).

Example 3: Separation of Murine T Cells

CD4$^+$, CD4$^+$CD25$^-$ T cells and CD4$^+$CD25+ Treg were separated from the splenocytes obtained from female Foxp3$^{EGFP}$C57BL/6 mice via magnetic bead separation (CD4$^+$ T cell separation kit and CD4$^+$CD25$^+$ regulatory T cell kit; Miltenyi Biotec, GmbH, Bergisch Gladbach, Germany) according to the manufacturer's instructions. The purities of all the populations were determined via flow cytometry analysis, and they conventionally reached 90% or higher.

Example 4: Reagents and Administration Routes

Bee venom (BV), melittin, secretory bee venom-derived phospholipase A2 (BV-PLA2), mast cell degranulating peptide (MCD) and apamin were prepared in PBS solutions for in vitro experiments. Each component was used according to the proportion of the venom, that is, 50% of melittin, 10% of BV-PLA2, 2% of apamin, and 1% of MCD. Bee venom and all components of bee venom were purchased from Sigma-Aldrich (St. Louis, Mo., USA). Bee venom stock solution was prepared by dissolving bee venom in 0.9% brine at a concentration of 1 mg/ml. The bee venom stock solution was used after dilution according to concentrations for dose-dependent in vivo experiments. Bee venom (0.01, 0.1, 1, and 10 mg/kg body weight) or an equal volume of brine was intraperitoneally injected into the mice daily.

Example 5: Growth Analysis

In an EAE-induced mouse model, the murine splenocytes immunized with $MOG_{35-55}$ peptides were separated when the symptoms of the disease reached its culminating point. Briefly, the splenocytes were cultured at a concentration of $2\times10^6$/ml in RPM 1640, which was added with 10% FBS, 50 IU/ml of penicillin, 50 μg/ml of streptomycin, 10 μg/ml of $MOG_{35-55}$ peptide and bee venom (0.01, 0.1, 1, and 10 μg/ml), for 72 hours. In order to determine the inhibitory effect of BV against antigen-specific growth, the number of splenocytes was counted using a hemocytometer. All the experiments were repeated three times.

Example 6: Flow Cytometry Analysis

All the cytometry analyses regarding the samples prepared according to the methods described below were performed using CellQuest Pro Software (BD Biosciences, San Jose, Calif., USA) after collecting data using FASC Calibur flow cytometer (BD Bioscience, San Jose, Calif., USA).

6.1. Cell Preparation for Cytometry Analysis in EAE-Induced Animal Model Experiments In order to define Treg, a suspension of separated single-cells obtained from $Foxp3^{EGFP}$C57BL/6 mice and splenocytes, and a healthy donor's PBMC were labeled with anti-CD4 and anti-CD25 or anti-Foxp3 monoclonal antibodies (eBioscience, San Diego, Calif., USA) according to the standard staining method. For the detection of intracellular cytokine expressions in mice and human cells, intracellular staining was performed using a cytofix/cytoperm kit (BD Biosciences, San Jose, Calif., USA) according to the manufacturer's instructions. Briefly, the cells were restimulated with 50 ng/ml of PMA and 1 μg/ml of ionomycin (both from Sigma-Aldrich, St. Louis, Mo., USA) for 5 hours in the presence of BD GOLGISTOP™ protein transport inhibitor. The cells were stained with BD mouse or human Th1/Th2/Th17 phenotyping cocktail according to the manufacturer's instructions. For the detection of cytokine production, the secreted cytokines were measured using cytometric bead array (CBA; BD Biosciences, San Jose, Calif., USA) according to the manufacturer's instructions. Twenty four days after immunization, sera were collected and stored at −20° C. before use for CBA analyses.

6.2. Cell Preparation for Cytometry Analysis in Allergic Asthma-Induced Animal Model Experiments After separating CD4$^+$ cells from the spleen of $Foxp3^{EGFP}$ Balb/c mice, they were seeded into a round bottom 96-well plate coated with anti-CD3e (2.5 μg/ml) for one day at a concentration of $4\times10^6$ cells/ml in the amount of 200 μl/well, costimulated with anti-CD28 (2 μg/ml), added with BV-PLA2 at a concentration of 0.1, 1 μg/ml, and cultured in an incubator (37° C., 5% $CO_2$) for three days. The resulting liquid culture was stored for cytokine measurement. Then, the resultant was added with CD4 and CD25 antibodies (anti-CD4-APC and anti-CD25-PE mAbs), which are cell surface markers, and placed at 4° C. for 30 minutes. The resultant was centrifuged at 300×g after suspending in 1 ml of Dulbecco's phosphate buffered saline (DPBS) (welGENE) and the supernatant was removed. The resultant was resuspended in 300 μl of DPBS, and the amount of expression of CD4$^+$CD25$^+$ Treg and Foxp3 were measured.

Additionally, for the analysis of cells in lung tissues, the lung was isolated and washed with PBS to remove blood. The lung tissues were cut into small pieces and lysed in a 1% RBC lysis buffer (BD Pharmingen). Upon lysis of RBC, the lung tissues were passed through a 25 μm cell strainer. The cells were washed three times and resuspended in FCM buffer solution (PBS containing 2% FBS and 0.1% $NaN_3$). The suspension of the single-cells obtained from $FOXP3^{EGFP}$ Balb/c mice and the lung cells were labeled with anti-CD4-APC and anti-CD25-PE monoclonal antibodies according to the standard staining method, and the percentage of the cells stained with a particular sample was analyzed via FACS Calibur using CellQuest Software (BD Biosciences).

Example 7: Measurement of Cytokines in the Supernatant of Liquid Culture

In an allergic asthma-induced model, splenocytes stimulated with anti-mouse CD3 antibodies and anti-mouse CD28 antibodies were treated with various concentrations of BV-PLA2 for three days. The supernatant of the liquid culture was recovered and centrifuged at 4° C. at a rate of 300 rcf for 10 minutes, and stored at −70° C. for future use. The level of measured cytokines was standardized relative to the cytokine level of the stimulated control group. Cytokines were measured via murine cytometric bead array (CBA, BD Biosciences, San Jose, Calif., USA). Briefly, 50 μl of a sample or standard sample at a concentration of a base (0-5000 pg/ml) was added into 50 μl of a mixture of a capture antibody bead solution and a detection antibody phycoeiythrin (PE) sample. Then, the resulting mixture was incubated at room temperature for two hours without sunlight, and washed to remove the unbound detection antibody PE sample. The data were collected using a flow cytometer (FACS Calibur, BD Biosciences Corp., San Jose, Calif., USA) and analyzed by a computer (CBA Software 1.1; BD Biosciences Corp.).

Example 8: Bronchoalveolar Lavage (BAL)

In an allergic asthma-induced model, BAL was collected by infusion and extraction of 1 ml of ice-cold PBS. The above procedure was repeated 3 times and the lavage was collected (average volume of 2.0 ml). The recovered BAL (70-80%) was centrifuged at 13000 rpm for 10 minutes. Cell precipitate was resuspended in 1 ml of PBS and attached to a glass slide via cytocnetrifugation. The total number of viable cells was measured using a hemocytometer according to trypan blue exclusion. The differential counts on eosinophils, neutrophils, lymphocytes, and macrophages were determined based on smear samples of bronchoalveolar lavage fluid (BALF) samples ($5\times10^5$ cells/200 μl) from an individual mouse stained with Diff-Quick (Life Technologies, Auckland, New Zealand) after counting 500 cells. Then, BALF was centrifuged and the supernatant to was stored at −70° C. The result was expressed as the total cell number$\times10^4$.

Example 9: Analysis of Th2 Cytokine in BALF Via Enzyme-Linked Immunosorbent Assay (ELISA)

In an allergic asthma-induced model, the concentrations of Th2 cytokine IL-4 and IL-13 were measured using a quantitative sandwich ELISA kit (BD, San Diego, USA for IL-4 and R&D, Minneapolis, USA for IL-13). A 96-well microplate was incubated at 4° C. overnight in a coating buffer solution along with anti-mouse IL-4 and IL-13 monoclonal antibodies, washed with PBS containing 0.05% Tween 20 (Sigma, MO, USA), and blocked respectively with PBS containing 5% FBS at 4° C. for one hour and with PBS containing 1% BSA for one hour. Then, 100 μl of BALF was added thereto and incubated at room temperature for two hours. Secondary peroxidase was labeled in an assay diluent with biotinylated anti-mouse IL-4 and IL-13 monoclonal antibodies for one hour. Finally, the plate was treated with TMB base solution (KPL, San Diego, USA) for 30 minutes, and then added with 50 nl of TMB stop solution to each well to stop the reaction. The absorbance at 450 nm was measured via a microplate reader (SOFT max PRO, version 3.1 Software, CA, USA). Here, the detection limit for IL-4 and IL-13 ELISA was 500 ng/ml and 100 ng/ml, respectively.

Example 10: Measurement of Serum IgE Titer Via ELISA

In an allergic asthma-induced model, the mice were anesthetized with ether 32 days after inducing the disease, and blood samples were collected from the retro-orbital plexus of the mice. Sera samples were obtained via centrifugation and stored at −20° C. until analysis. Regarding the sera, a 96-well immune microplate (Costar, NY, USA) was coated with anti-mouse IgE monoclonal antibodies. The sera were diluted with PBS (assay diluents) containing 5% FBS at 1:250 ratio. The IgE measurement (BD Pharmingen) was used for a standardized sandwich ELISA according to the manufacturer's protocol. The absorbance at 450 nm was measured via a microplate reader (SOFT max PRO, version 3.1 Software, CA, USA). Here, the detection limit for IgE ELISA was 100 ng/ml, respectively.

Example 11: Histological Examination

In an allergic asthma-induced model, trachea and lung tissues were removed from the mice. First, they were fixed with 4% paraformaldehyde, sunk into paraffin after dehydration, cut into 6 t m slices, and stained with Hematoxylin & Eosin (H&E) and Periodic Acid Schiff (PAS) reagents.

Example 12: Measurement of Airway Hyperresponsiveness (AHR) on Methacholine

In an allergic asthma-induced model, on the day immediately following the final test-infection by administration of 50 μl of PBS containing 1% OVA, the experimental animals were put into a barometric plethysmographic chamber (All Medicus, Seoul, Korea) and analyzed. The baseline reading was performed for 3 minutes. The enhanced pause ($P_{enh}$) was calculated according to the manufacturer's protocol [i.e., (expiratory time/relaxation time−1)χ(peak expiator)/flow/peak inspiratory flow)]. $P_{enh}$ is dimensionless parameter that represents a function of the proportion of maximal expiratory to maximal inspiratory box pressure signals and a function of the timing of expiration. The results were expressed in percentage increase of $P_{enh}$ according to the test-infection of methacholine (0, 50 and 100 mg/ml).

Example 13: Immunohistochemistry

In an MPTP-addicted Parkinson's disease animal model, a brine containing 0.5% sodium nitrate and heparin (10 U/ml) was transcardially perfused through the experimental and fixed with 4% paraformaldehyde dissolved in 0.1M phosphate buffer (PB). The brain was removed and fixed in buffered 4% paraformaldehyde overnight, and stored in 30% sucrose solution maintained at 4° C. until it became sunk. The brain was fractioned into coronal slices with a thickness of 30 using a sliding microtome and frozen. All the fractions in six separated series were collected and subjected to immunochemical staining. The primary antibodies include those responding to tyrosine hydroxylase; TH; 1:2000, Pelfreez, Brown Deer, Wis., USA). The stained cells were visualized and then analyzed under brightfield microscope (Nikon, Tokyo, Japan).

Example 14: Preparation of Recombinant BV-PLA2 and Analysis of its Activity

In order to prepare polypeptides including a BV-PLA2 amino acid sequence via recombinant expression, E. coli DH5α and E. coli BL21 (DE3) were respectively used as the strains for the expression of gene manipulation and protein expression.

14.1. Culturing Bacteria and Purification of Recombinant Proteins

For a large scale production of proteins, 5 ml of a fresh overnight liquid culture of a selected bacteria strain was diluted with 1 L of LB medium containing ampicillin as an antibiotic. The recombinant E. coli BL21 (DE3) cells containing an expression plasmid were cultured at 37° C. while stirring until the absorbance at 600 nm reached about 0.9. The expression of the recombinant PLA2 was induced in a logarithmic growth phase by adding 1 mM isopropyl-β-d-thiogalactoside (IPTG) to the liquid culture. The overnight culture was centrifuged at 4° C. at a rate of 3000 rpm for 20 minutes and recovered the cells. The cell pellet was suspended in a buffer solution A (50 mM sodium phosphate buffer, pH 8.0, and 0.1 mM PMSF and 5 mM β-mercaptoethanol). After pulverizing the cells using an ultrasonicator, they were centrifuged at 4° C. at a rate of 12000 rpm for 10 minutes, and washed with a buffer solution B (50 mM sodium phosphate buffer, pH 8.0, 2% Triton X-100, 20 mM EDTA, and 0.5 M NaCl) to prepare an insoluble pellet. Then, the resultant was modified in a buffer solution C (a buffer solution A containing 8 M urea) for at least 12 hours. The insoluble cell debris combined with the modified recombinant PLA2 was removed by centrifugation at 4° C. at a rate of 12000 rpm for 20 minutes. The histidine-labeled recombinant to PLA2 protein was purified via immobilized-metal affinity chromatography using His GraviTrap affinity column (GE Healthcare, Piscataway, N.J., USA). The histidine-labeled recombinant PLA2 protein was dialyzed twice at 4° C. using 3 L of 5 mM acetic acid for 12 hours and lyophilized.

14.2. Refolding of Proteins

The lyophilized protein was dissolved in 7 M guanidine-HCl, and then added with 0.3 M Na2SO3 (pH 8.3) and a ½₀ volume of Thannhauser reagent for the sulfonification of cysteine thiol. The resulting solution was dialyzed against 3 L of a mixed solution containing 2 M urea, 4 mM EDTA, 0.1 M NH4Cl, and 20 mM sodium boronate (pH 8.3) for four hours and then the dialyzed solution was replaced with a fresh solution. After an additional four hours of dialysis, 56 ml of an aqueous solution of 0.5 M cysteine, and 17.5 mL of 0.2 M of cystine solution dissolved in 1 M HCl solution were added to the dialyzed solution, and the pH was adjusted to 8.3 using 10 M NaOH. At the appropriate time point, the dialyzed solution was transferred into a beaker wrapped with aluminum foil. When the activity reached the maximum level (generally from 18 to 24 hours after addition of cysteine and cystin), the proteins solution was decanted from the agglutinated precipitate, and dialyzed at 4° C. with 3 L of SP buffer solution (50 mM Tris-HCl, pH 9.0) for 14 hours. The protein purity was confirmed via SDS-PAGE using 15% (w/v) polyacrylamide for stacking and separating gels.

14.3. Activity Analysis of Recombinant Proteins

Enzyme activities were determined by an ENZCHECK® phospholipase A2 analysis kit (Invitrogen) which uses DOPC as a substrate. According to the manufacturer's protocol, the enzyme activities of BV-PLA2 and recombinant PLA2 were analyzed using the ENZCHECK® phospholipase A2 analysis kit.

Example 15: Construction of Expression Plasmid and Site-Directed Mutagenesis

The nucleotide sequence of the BV-PLA2 gene used in the present invention was inserted in advance into a cloning site of SalI-EcoRI of pEcoli-Nterm 6×HN vector. The construction of the mutants of the BV-PLA2 gene was performed using primer pairs shown below: F-type BV-PLA2 (forward): 5'-AAT GTC GAC CAA GTC GTT CTC GGA T-3' (SEQ ID NO: 12); F-type BV-PLA2 (Reverse): 5'-AAG GAATTC TTATCAATA CTT GCG-3' (SEQ ID NO: 13); A-type BV-PLA2 (Forward): 5'-AAT GTC GAC ATAATATAT CCA GGA-3'(SEQ ID NO: 14); A-type BV-PLA2 (Reverse): 5'-AAG GAATTC TCA CAG TTT GTAACA CTT-3'(SEQ ID NO: 15); B-type BV-PLA2 (Forward): 5'-AAT GTC GAC CAA GTC GTT CTC GGA T-3'(SEQ ID NO: 16); B-type BV-PLA2 (Reverse): 5'-AAG GAATTC TCA CAG TTT GTAACA CTT-3'(SEQ ID NO: 17); C-type BV-PLA2 (Forward): 5'-AAT GTC GAC ATAATATAT CCA GGA-3'(SEQ ID NO: 18); C-type BV-PLA2 (Reverse): 5'-AAG GAA TTC TTA TCAATA CTT GCG-3'(SEQ ID NO: 19). A single mutation was introduced into a template, which is a genetic mutant of BV-PLA2 (H34Q), within the pEcoli-Nterm 6×HN vector using a QuickChange site-directed mutagenesis kit (Stratagene). The reaction was performed using the primer pairs shown below: PLA2-H34Q (Forward): 5'-GCATGC TGT CGAACC CAA GAC ATG TGC CCG GAC G-3'(SEQ ID NO: 20); PLA2-H34Q (Reverse): 5'-CGT CCG GGC ACA TGT CTTGGG TTC GAC AGC ATG C-3'(SEQ ID NO: 21). The substituted nucleotides were underlined. The validity of the nucleotide sequences of mutants were confirmed by DNA sequencing analysis.

Example 16: Measurement of CD4+CD25+Foxp3+ Regulatory T Cells (Tregs)

Flow cytometry analyses were performed for the samples prepared by the methods described below, and the proportional ratio of CD4+CD25+Foxp3+ regulatory T cell (Treg) for each cell was measured accordingly.

16.1. Measurement of CD4+CD25+Foxp3+ Regulatory T Cells (Tregs) from Murine Splenocytes Spleens were obtained from six to eight-week old female C57BL/6$^{Foxp3-EGFP}$ mice. The spleens were pulverized using a glass slide in the RPMI 1640 medium, and the cells were washed with RPMI 1640 medium, and then washed with red blood cell lysis buffer solution (Pharmingen). A 48-well plate with a flat bottom was coated at 4° C. with anti-mouse CD3 antibodies (2.5 mg/ml) overnight. The splenocytes were seeded into the 48-well plate at a cell density of 4×10$^6$ cells/ml, treated with anti-mouse CD28 antibodies (2 mg/ml), and then treated with PBS, PLA2 or recombinant PLA2 for three days and seven days. After the three day and seven day treatments with the recombinant PLA2, the single-cell suspension of the splenocytes were incubated with anti-CD4-APC and anti-CD25-PE monoclonal antibodies using the standard staining method, and the stained samples were analyzed via a flow cytometer (FAC-Scan Calibur, BD Biosciences). The collection and analysis of data were carried out using a Cell Quest 3.0f software.

16.2. Measurement of CD4+CD25+Foxp3+ Regulatory T Cells (Tregs) from Murine CD4+ T Cells Murine CD4+ Tcells were separated from spleens via MACS CD4 (L3T4) MicroBeads (Miltenyi Biotec Inc., Auburn, Calif., USA). The prepared single-cell suspension type cells were combined with the CD4 (L3T4) MicroBeads and incubated at 4° C. for 15 minutes.

After incubation, the cells were washed with MACS buffer and resuspended in a small volume. The cells were passed through an LS column mounted to VarioMACS magnetic separator. The resultant was washed three to four times and the recovered CD4+ cells were resuspended in a complete RPMI 1640 medium. The 48-well plate with a flat bottom was coated at 4° C. with anti-mouse CD3 antibodies (2.5 mg/ml) overnight. The CD4+ cells were seeded into the 48-well plate at a cell density of 1×10$^6$ cells/ml, treated in the same manner as in Example 16.1, and subjected to flow cytometry analysis.

Example 17: Analysis of Statistical Data

The statistical analysis of data was performed via Prism 5.01 Software (Graph Pad Software Inc., CA, USA). All the values were indicated via mean±S. E. M. (standard error of the mean). The differences between the control group and the groups treated with samples were determined one-way ANOVA or student t test. In all experiments, p<0.05 was considered to be of statistical significance.

Results of Experiments

Figure 2B:
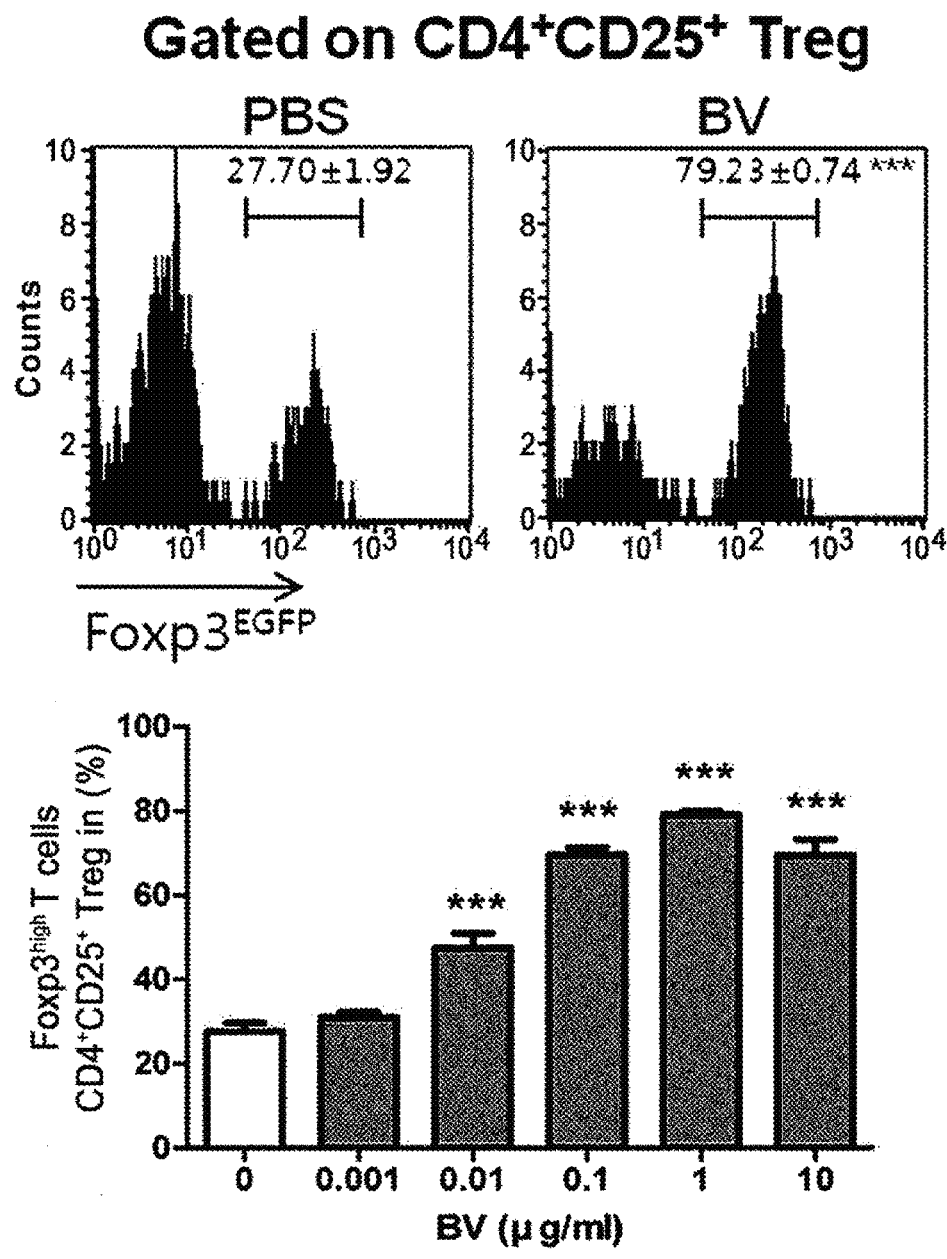
Figure 2C:
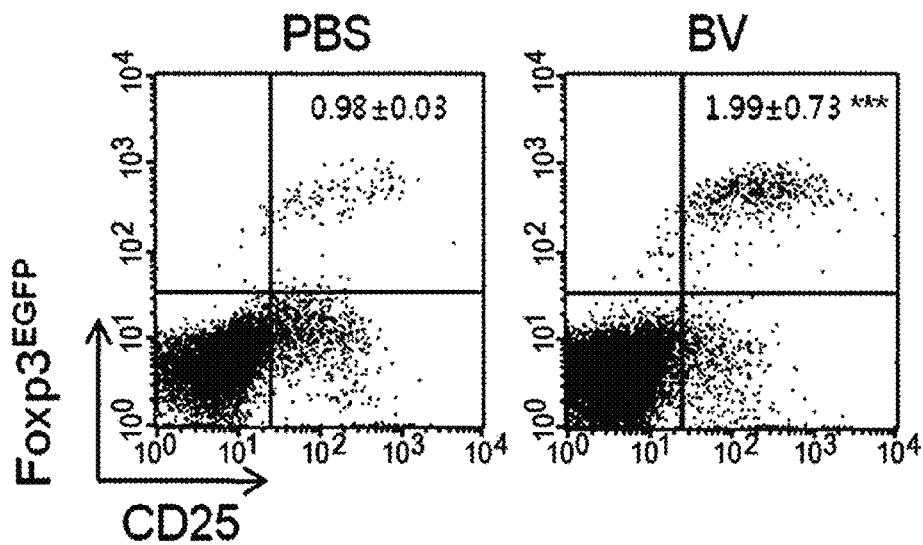
Figure 2D:
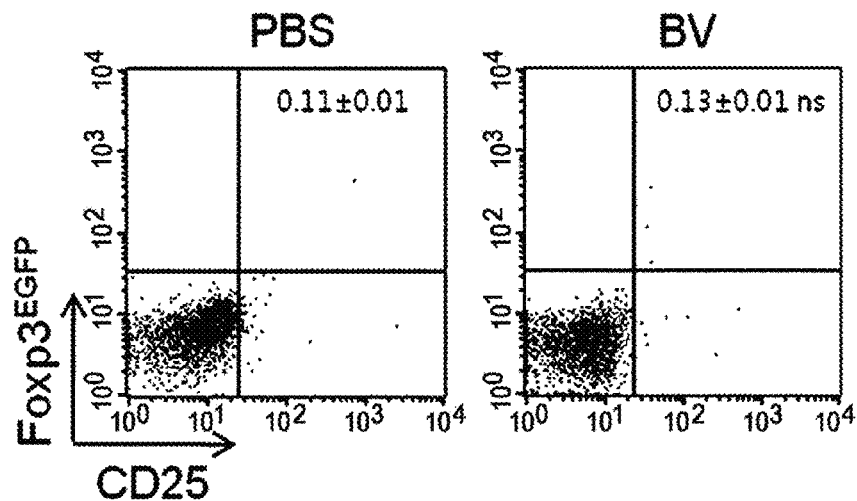
Figure 2E:
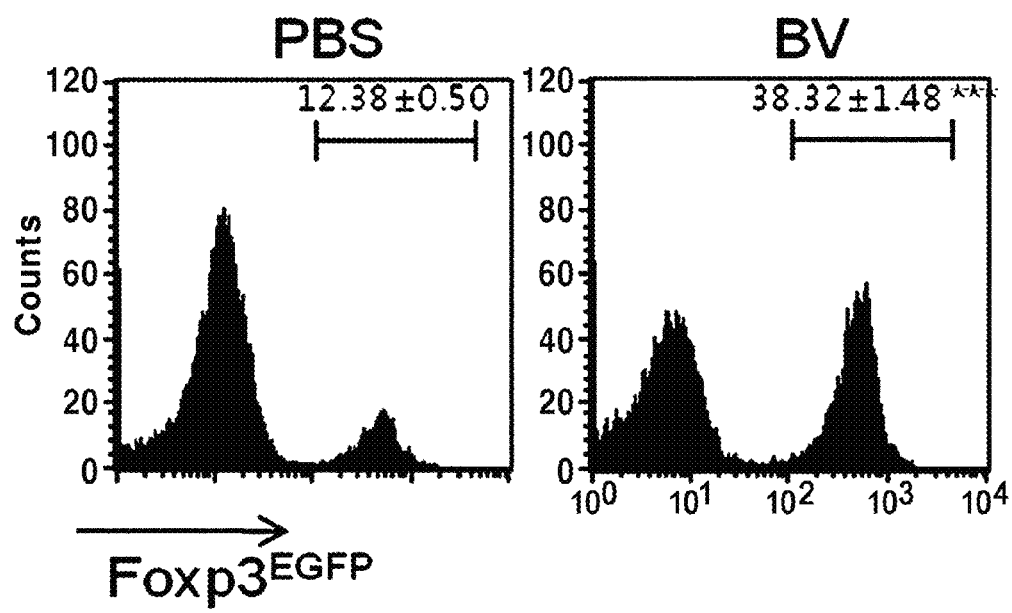

Experimental Example 1: In Vitro Direct Increase of CD4+CD25+Foxp3+ Treg by Bee Venom The CD4+CD25+Foxp3+ Treg population and the expression of Foxp3 in the CD4+CD25+ Treg in Example 6.1 were analyzed via in vitro immunofluorescence method. Splenocytes were treated in vitro with bee venom at various concentrations (0, 0.001, 0.01, 0.1, 1, and 10 μg/ml) and the effects according to the concentration were observed (FIGS. 2A and 2B). The bee venom (1 μg/ml) noticeably increased the CD4+CD25+Foxp3+ Treg (P<0.05) and also increased the expression of Foxp3 in CD4+CD25+ Treg (P<0.001). The bee venom added to the splenocytes can presumably affect the CD4+ T cells directly or through antigen presenting cells (APC). In order to determine whether bee venom directly acts on CD4+ T cells, the CD4+ T cells were separated and treated with bee venom (1 μg/ml) (FIG. 2C). When the CD4+ T cells were cultured without APC there was an increase in the CD4+CD25+Foxp3+ Treg (P<0.001). Subsequently, it was examined whether bee venom converts the CD4+CD25− T cells into the CD4+CD25+Foxp3+ Tregs. When the CD4+CD25− T cells were added with bee venom there was no increase in the Treg (FIG. 2D), whereas there was a noticeable increase in the expression of Foxp3 in the CD4+CD25+ Treg, which was cultured alone after bee venom treatment (FIG. 2E, P<0.001). The above results confirmed that bee venom increases the CD4+CD25+Foxp3+ Treg via direct influence on the CD4+CD25+ Treg instead of Treg induction from the CD4+CD25− T cells.

Figure 3A:
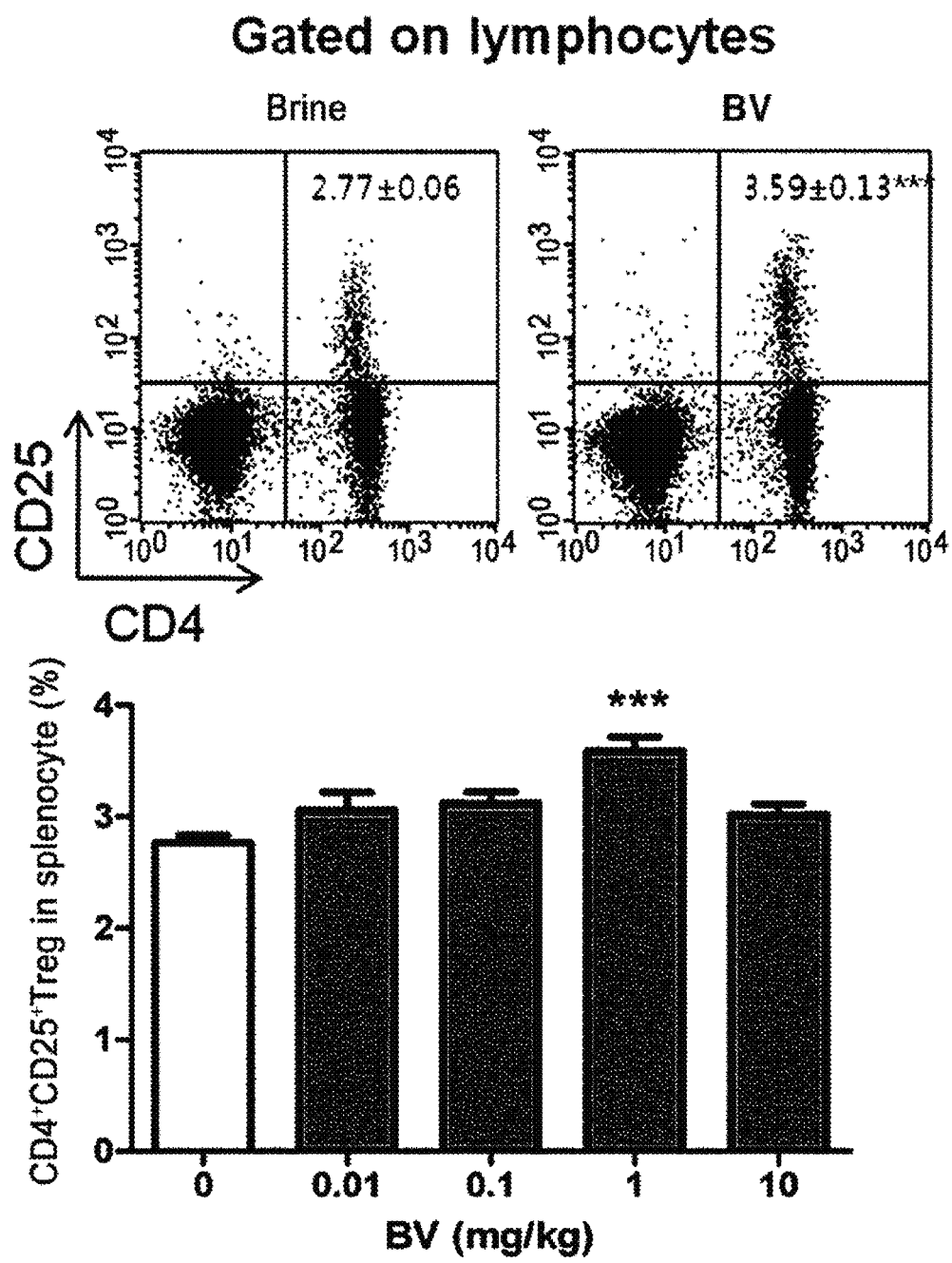
FIG. 3A-D shows graphs illustrating the effect of bee venom (BV) on the proportion of various in vivo cell populations. Foxp3$^{EGP}$ C57BL/6 mice or C57BL/6 mice were administered with bee venom (0.01, 0.1, 1, and 10 mg/kg body weight) or an equal volume of brine daily for 5 days via intraperitoneal injection. The single-cell suspension of splenocytes was stained with fluorescence-labeled CD4, CD8a, CD19 and CD25 antibodies. (A) shows graphs illustrating the percentages of CD4+CD25+ Treg measured in murine splenocytes. (B) shows graphs illustrating the expression rates of Foxp measured after gating on the CD4+CD25+ Treg. The percentage is a proportion of Foxp3$^{high}$ cells being gated on the CD4+CD25+ Treg. (C) shows the expression rates of CD25 and/or Foxp3 measured after gating on the CD4+ T cells. The numbers within the dot plots of (A) and (C) respectively represent the percentage of cells belonging to the corresponding quadrant. (D) represents the percentage of the CD4+CD25+Foxp3+ Treg in the CD4+ T cells, or the percentage of the CD4+ T cells in the splenocytes, CD8+ T cells, and B cells. The data is indicated via mean±SEM ((ns; not significant), *p<0.05, p<0.01, *p<0.001 vs. a brine-treated group).
Figure 3B:
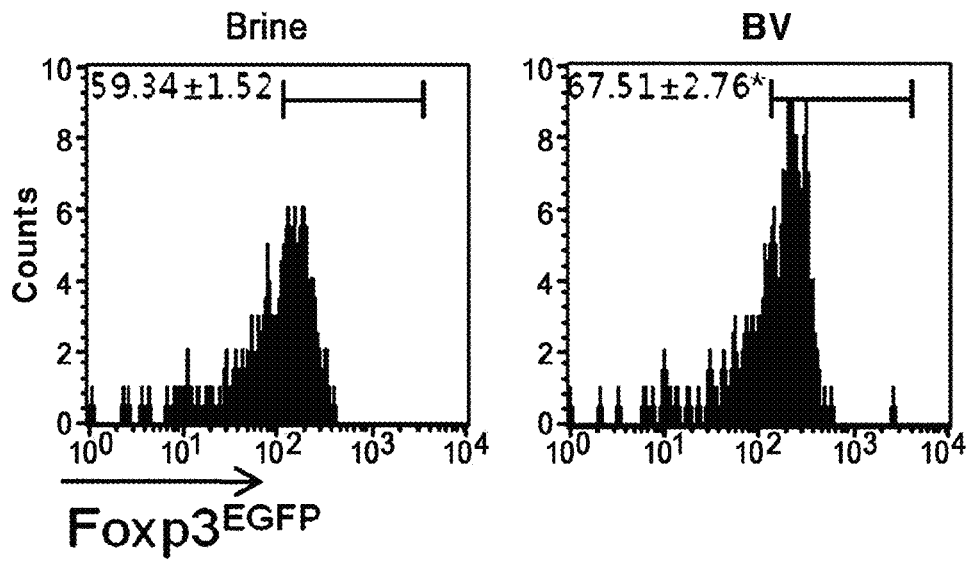
Figure 3C:
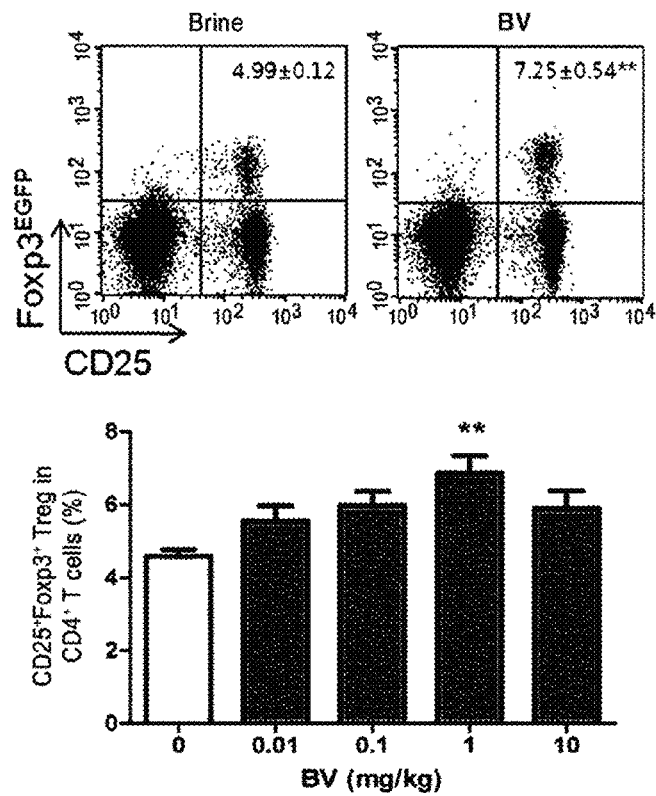
Figure 3D:
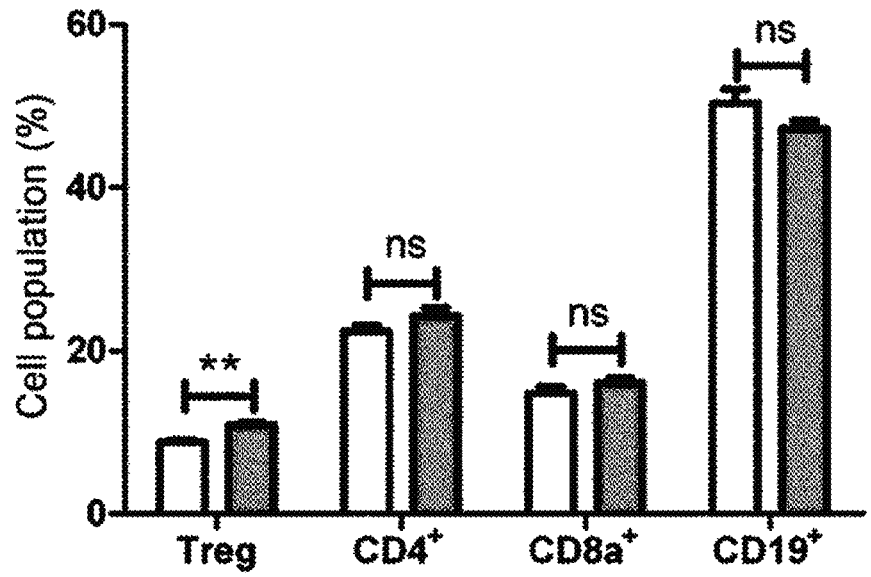

Effect of Treg-Specific Increase of Bee Venom and its In Vivo Efficacy According to its Dose In order to determine the optimum dose of bee venom for in vivo experiments, the experimental mice were treated daily with various amounts of bee venom (0, 0.01, 0.1, 1 and 10 mg/kg body weight) for five days. Notwithstanding with the various amounts of bee venom, only the mice treated with 1 mg/kg of bee venom showed a significant increase of the level of CD4+CD25+ Treg compared to that of the brine-treated control group (FIG. 3A, P<0.001). The Foxp3 expression in the CD4$^+$CD25$^+$ Treg showed a noticeable increase as is the case with in vitro experiment (FIG. 3B, P<0.05). Then, the effects of bee venom (1 mg/kg) on other immune cells containing CD4$^+$ T cells, CD8$^+$ T cells and B cells were analyzed. While there was no significant increase in the CD4$^+$ T cells, CD8$^+$ T cells and B cells as compared to the brine-treated control group, the CD4$^+$CD25$^+$Foxp3$^+$ Treg showed a significant increase (FIGS. 3C and 3D). The above results confirmed that the dose of bee venom is a crucial factor in its efficacy and that 1 mg/kg may be the optimum dose for immunological therapy.

Figure 4:
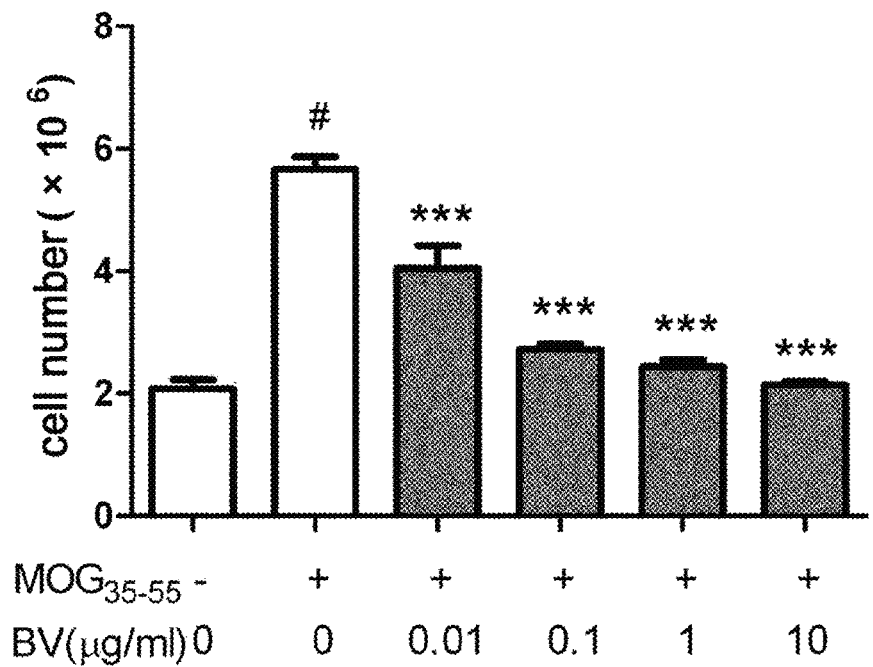
FIG. 4 shows a graph illustrating the in vitro inhibitory effect of bee venom against antigen-specific growth. The splenocytes of an experimental autoimmune encephalomyelitis (EAE)-induced C57BL/6 mice were stimulated with MOG$_{35-55}$ peptide and counted 72 hours thereafter. The data is indicated via mean±SEM ((ns; not significant), #p<0.001 vs. non-stimulated cells, ***p<0.001 vs. PBS-treated cells).

Experimental Example 3: In Vitro Myelin-Specific Growth Inhibitory Effect of Bee Venom The experiment results explained above indicate that bee venom has the potential therapeutic effect to be used for the treatment of autoimmune diseases. In order to confirm the assumption, firstly, antigen-specific growth analysis was performed (FIG. 4). The splenocytes of C57BL/6 mice immunized with MOG$_{35-55}$ were restimulated with MOG$_{35-55}$ peptide and counted the cell number 72 hours thereafter. As a result, it was confirmed that the myelin-specific growth of the splenocytes were inhibited by bee venom in a concentration-dependent manner (P<0.001).

Figure 5A:
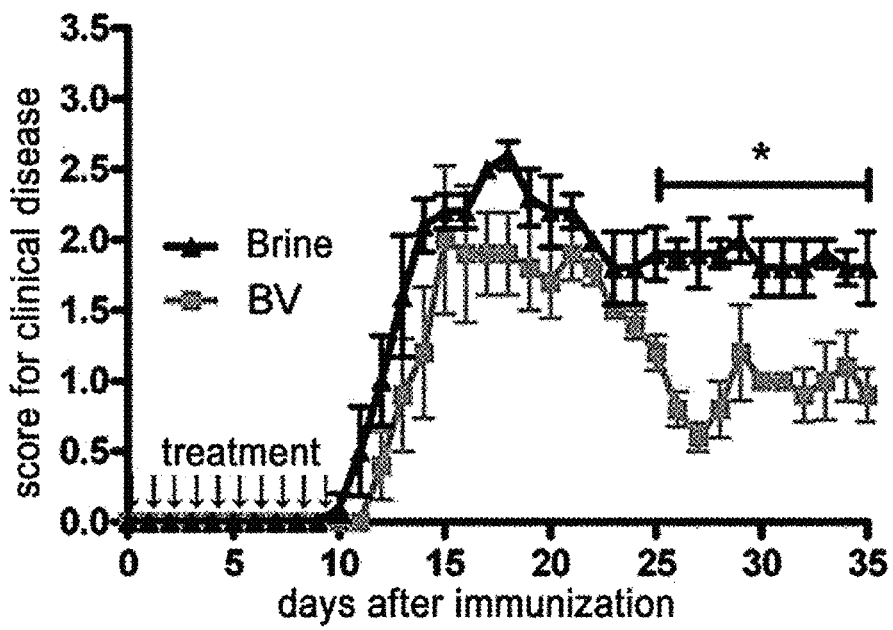
FIG. 5A-D shows graphs illustrating the effects of bee venom on alleviating EAE via inhibition of Th1/Th17 differentiation. The C57BL/6 mice were immunized with MOG$_{35-55}$ peptide. (A) shows a graph illustrating mean clinical disease scores measured by monitoring the mouse for 35 days after treating the mouse with bee venom (1 mg/kg body weight) from day 0 to 9th day after immunization (n=5/group). In (B) through (D), the mice were treated with bee venom (1 mg/kg body weight) from the 14th day to the 23$^{rd}$ day after immunization (n=12/group). (B) shows a graph illustrating mean clinical disease scores measured by monitoring the mouse for 35 days (n=12/group), (C) shows Th1/Th17 percentages measured after re-stimulating the splenocytes with PMA (50 ng/ml) and ionomycin (1 µg/ml) for 5 hours in the presence of monensin (n=11/group), and (D) shows cytokine concentration in the serum measured after collecting on the 24$^{th}$ day (n=8/group). shows Th1/Th17 percentages measured after re-stimulating the splenocytes with PMA (50 ng/ml) and ionomycin (1 µg/ml) for 5 hours in the presence of monensin (n=11/group), and (D) shows cytokine concentration in the serum measured after collecting on the 24$^{th}$ day (n=8/group). The data is indicated via mean±SEM (*p<0.05, **p<0.01 vs. brine-treated group).
Figure 5B:
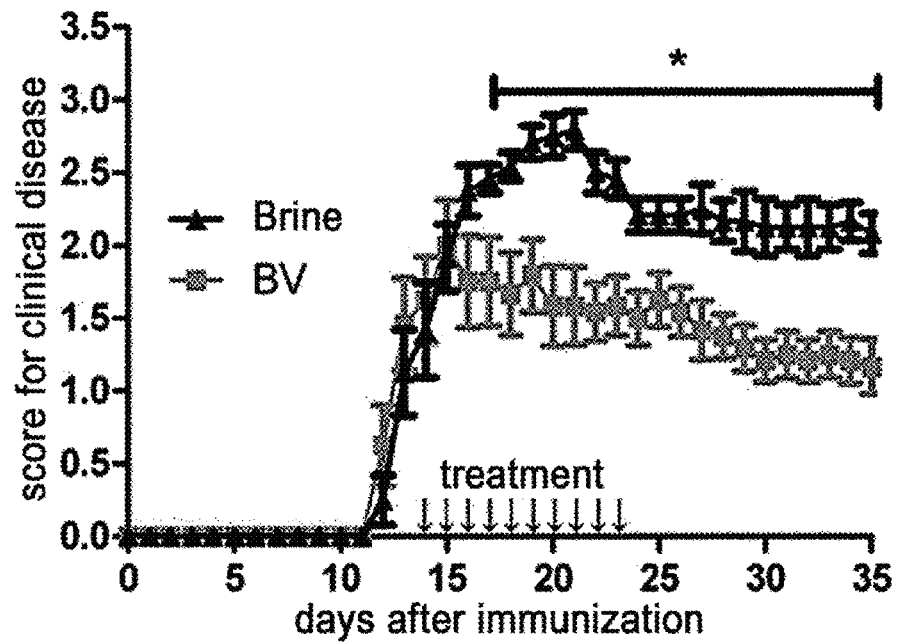
Figure 5C:
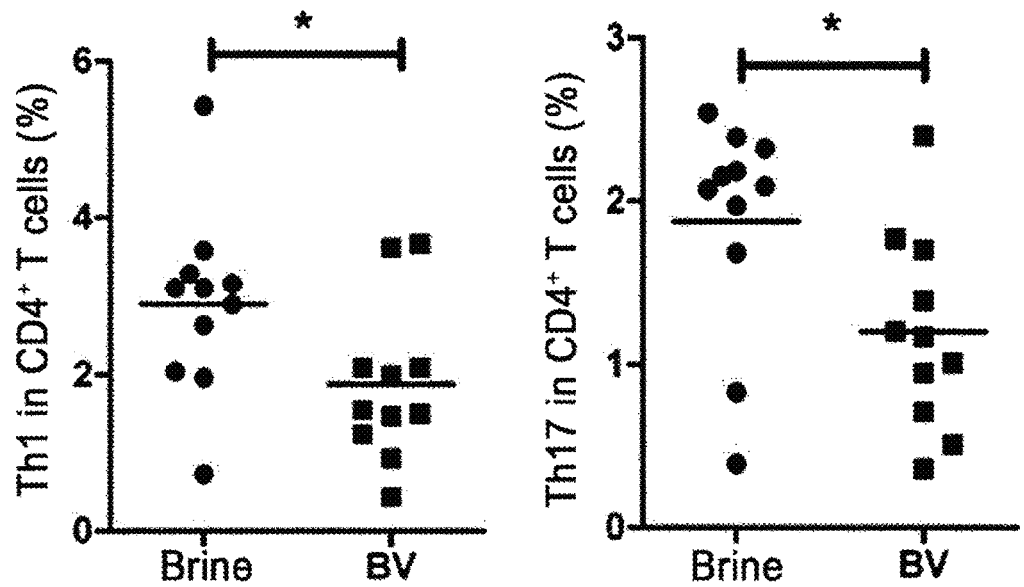

Experimental Example 4: Alleviation of EAE in C57BL/6 Mice by Bee Venom Via Inhibition of Th1/Th17 Differentiation The possibility of whether the effect of bee venom can be interpreted via in vivo to experiments was sequentially examined. As the first step, the C57BL/6 mice immunized with MOG$_{35-55}$ were treated daily with bee venom (1 mg/kg) from day 0 or day 14 for ten days (FIGS. 5A and 5B). The result showed that bee venom lowered severity of diseases as compared to that of brine-treated mice. This result shows that bee venom has the effects of prevention and treatment in EAE, which is an established animal model for multiple sclerosis (MS). MS and EAE have been already reported to be mediated by Th1/Th17 reactions. Accordingly, the present inventors studied the effect of bee venom whether it can inhibit Th1/Th17 differentiation. To this end, they conducted tests on the CD4$^+$ T cells of EAE-induced mice (FIG. 5C). Both Th1 (P<0.05) and Th17 (P<0.05) differentiations were significantly blocked by bee venom treatment.

Figure 5D:
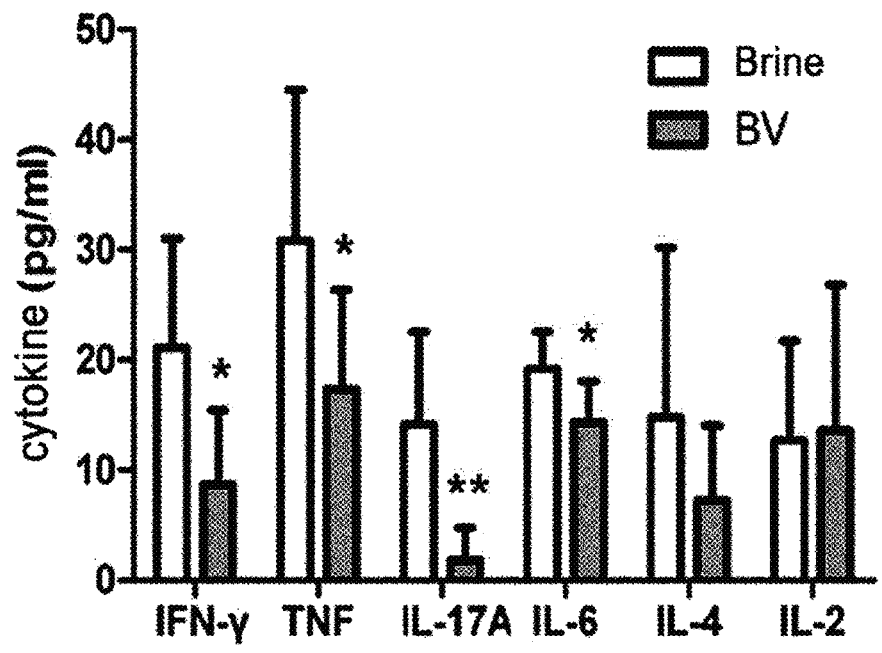

Additionally, in order to test whether the Th1/Th17 differentiation affects the cytokine production, the sera cytokines profiles of the bee venom-treated mice and the brine-treated mice were analyzed on day 24 (FIG. 5D). The result showed that the bee venom treatment significantly reduced the production of other inflammatory cytokines including IFN-γ (P<0.05), IL-17A (P<0.01), TNF (P<0.05) and IL-6 (P<0.05) in the sera. Interestingly, the level of IL-4, which is the main Th2 (IL-4 producing CD4$^+$ T cells) cytokine, was also reduced. The above results confirmed that bee venom has the inhibitory effect against the Th1/Th17 differentiation.

Figure 6A:
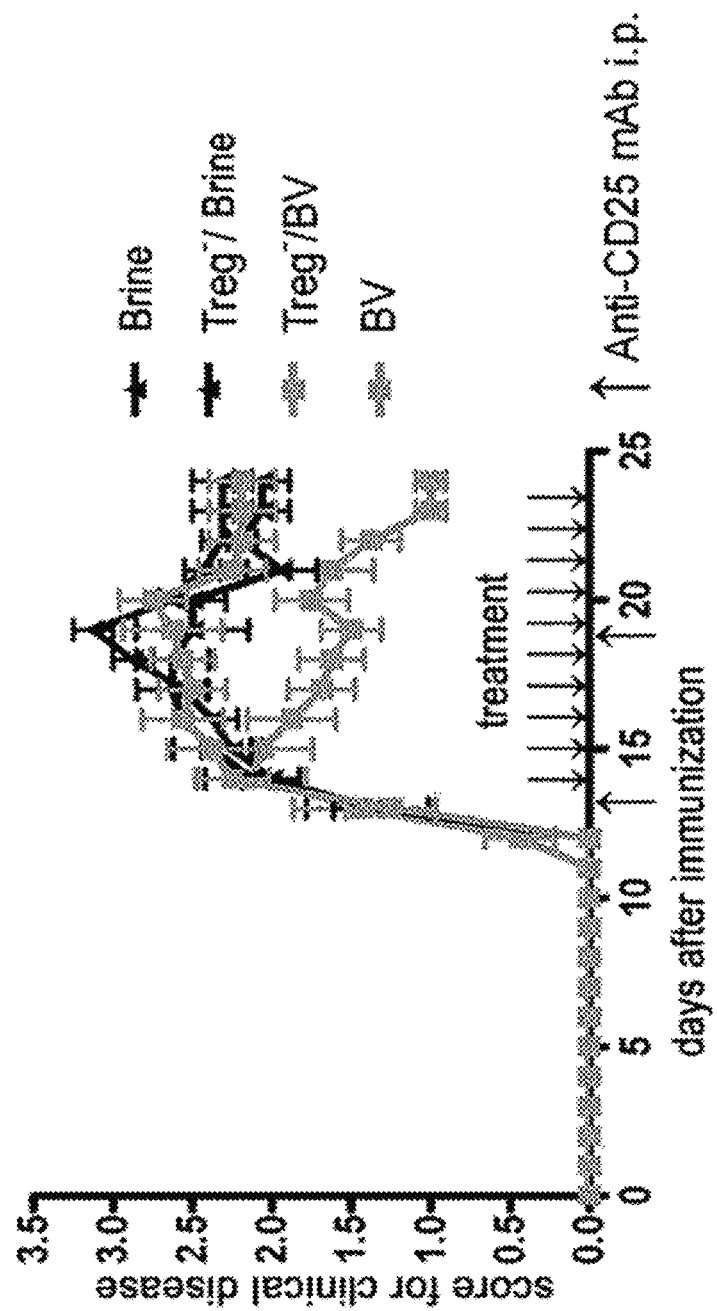
FIG. 6A-C shows the effect of bee venom on alleviating EAE blocked due to the CD4$^+$CD25$^+$ Treg cell depletion. C57BL/6 mice were immunized with MOG$_{35-55}$ peptide. Anti-CD25 antibodies were administered on the 13$^{th}$ day and the 19$^{th}$ day (respectively, the early stage treated with bee venom and an intermediate stage) of Treg depletion via intraperitoneal injection (A) shows a graph illustrating mean clinical disease scores measured by monitoring for 24 days. (B) and (C) show the results of analysis after sacrificing the mice on the 24$^{th}$ day after immunization (B) shows Th1/Th17 percentages measured after re-stimulating the splenocytes with PMA (50 ng/ml) and ionomycin (1 µg/ml) for 5 hours in the presence of monensin (n=8/group), and (C) shows cytokine concentration in the serum measured after collecting on the 24$^{th}$ day (n=5/group). The data is indicated via mean±SEM (ns; not significant).
Figure 6B:
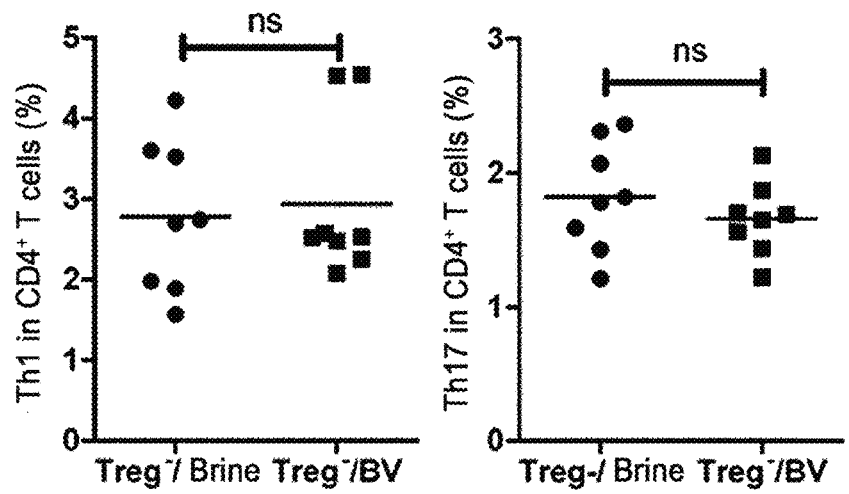
Figure 6C:
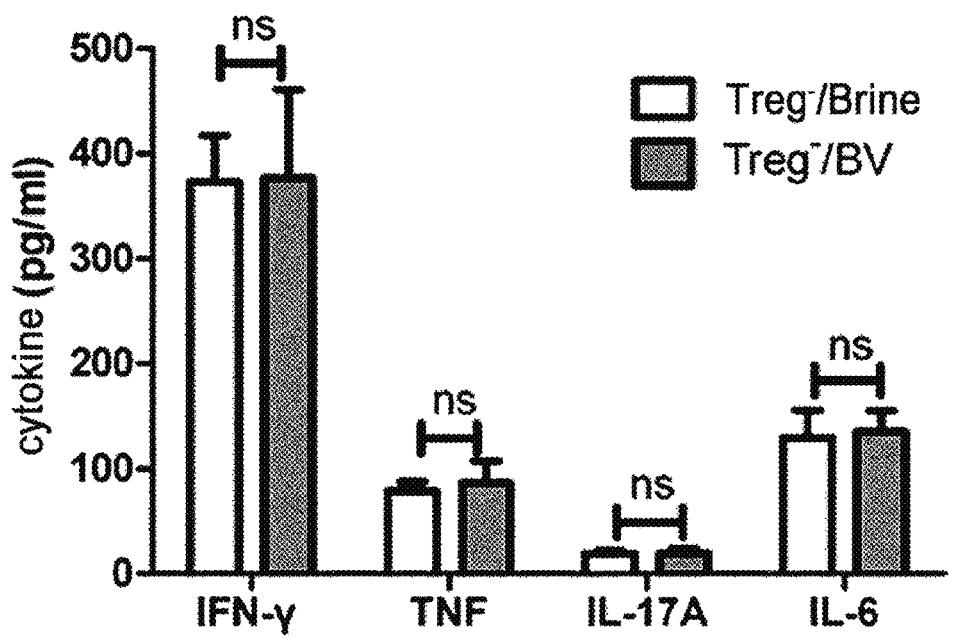

Experimental Example 5: Relationship Between the Effect of Bee Venom on EAE Alleviation and CD4$^+$CD25$^+$ Treg Experimental Example 1 showed that bee venom increased CD4$^+$CD25$^+$Foxp3$^+$ Treg. Additionally, Experimental Example 4 suggested that bee venom alleviates EAE by the inhibition of the Th1/Th17 differentiation. The above results imply that the increase in the CD4$^+$CD25$^+$Foxp3$^+$ Treg by bee venom may prevent the Th1/Th17 differentiation thereby improving EAE. To confirm the above hypothesis, Treg deficiency was applied with anti-CD25 to monoclonal antibodies concurrently with the bee venom treatment on EAE. The previous results showed that the anti-CD25 monoclonal antibody is suitable for the CD4$^+$CD25$^+$ Treg deficiency in mice, and since most CD4$^+$CD25$^+$ T cells in the present invention exhibit positive result on Foxp3 and thus can be determined by Treg. Additionally, the present inventors analyzed the progress of EAE and the Th1/Th17 differentiation including cytokine production (FIG. 6). The result revealed that there was no distinct difference in clinical scores, the Th1/Th17 differentiation or cytokine production. Conclusively, Treg deficiency blocks the effect of bee venom on EAE. According to an exemplary embodiment, the bee venom treatment in mice alleviated EAE via its direct effect on the CD4$^+$CD25$^+$ Treg.

Figure 7A:
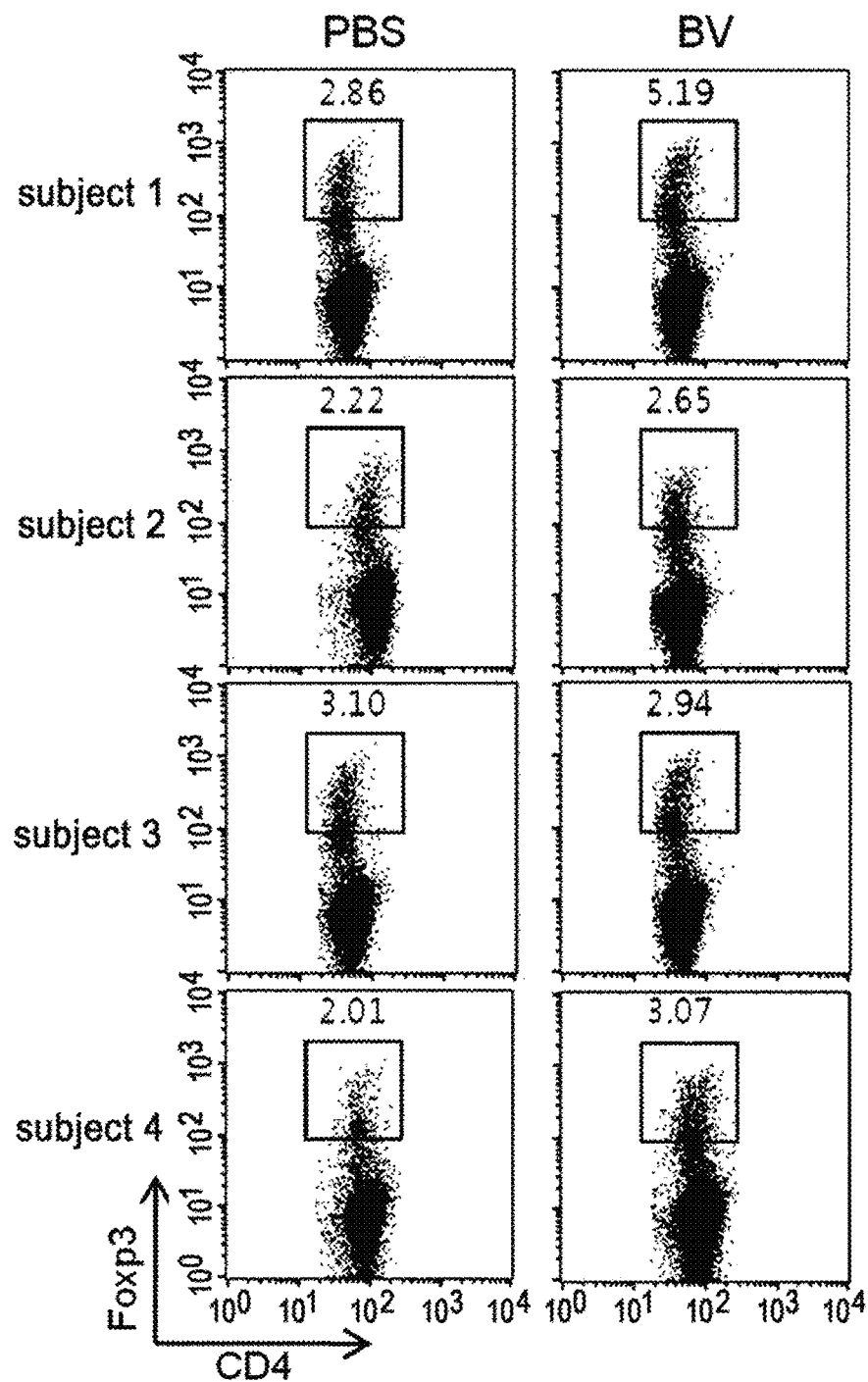
FIG. 7A-C shows the effect of bee venom on the increase of CD4$^+$Foxp3$^+$ Treg and the decrease of Th1/Th17. Foxp3$^+$ Treg or Th1/Th17 was analyzed by gating on human CD4$^+$ T cells. (A) shows the proportional ratio of CD4$^+$Foxp3$^+$ cells, which were treated with bee venom (1 µg/ml) for 24 hours after separating PBMC and gating, indicated in percentages. (B-C) was treated with bee venom (1 µg/ml) and anti-CD3/28 antibodies for 24 hours after separating PBMC. Then, the cells were re-stimulated with PMA (50 ng/ml) and ionomycin (1 µg/ml) for 5 hours in the presence of monensin, and the result is shown in terms of population distribution. The numbers within the dot plots represent the percentage of cells belonging to the corresponding quadrant.
Figure 7B:
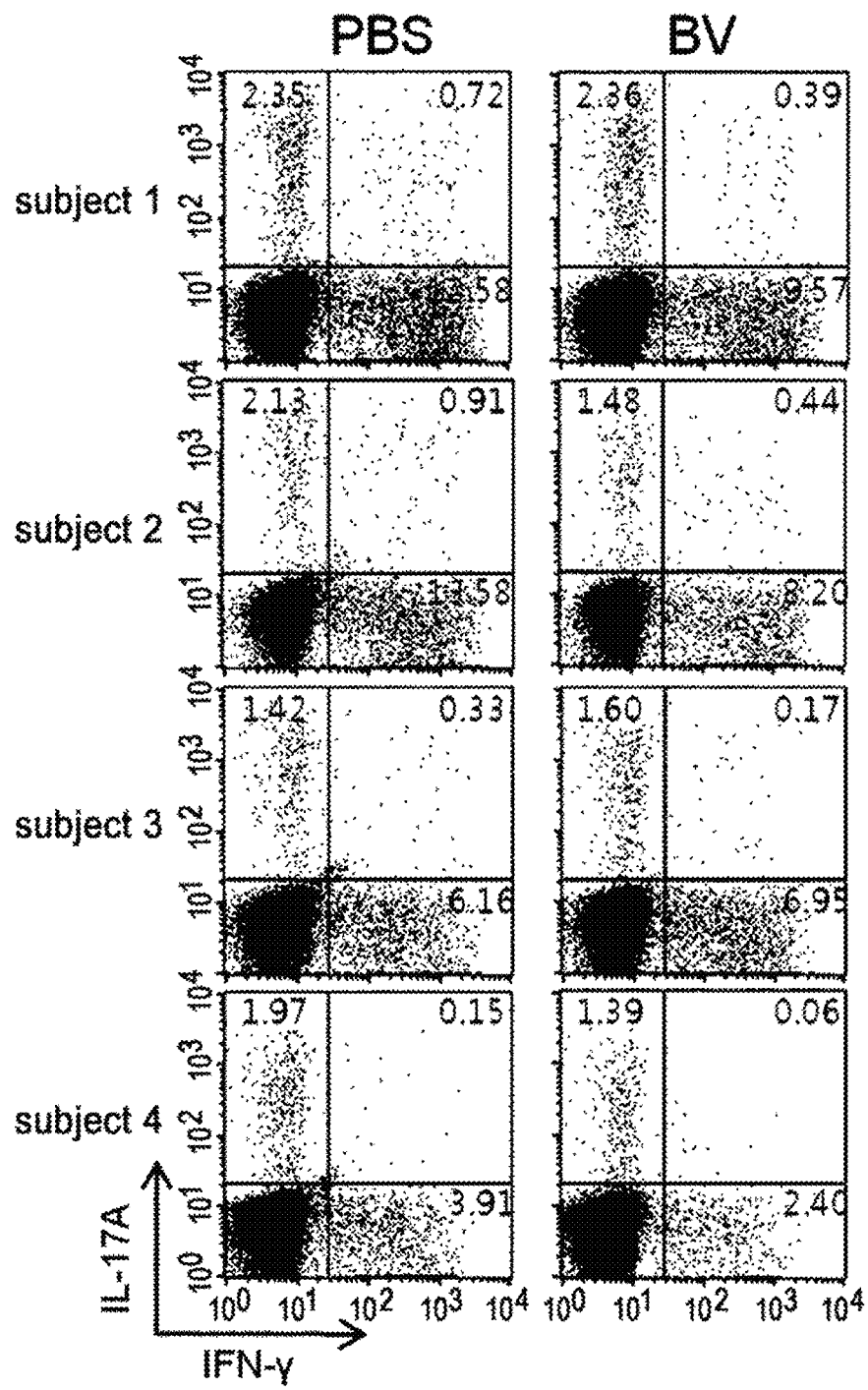
Figure 7C:
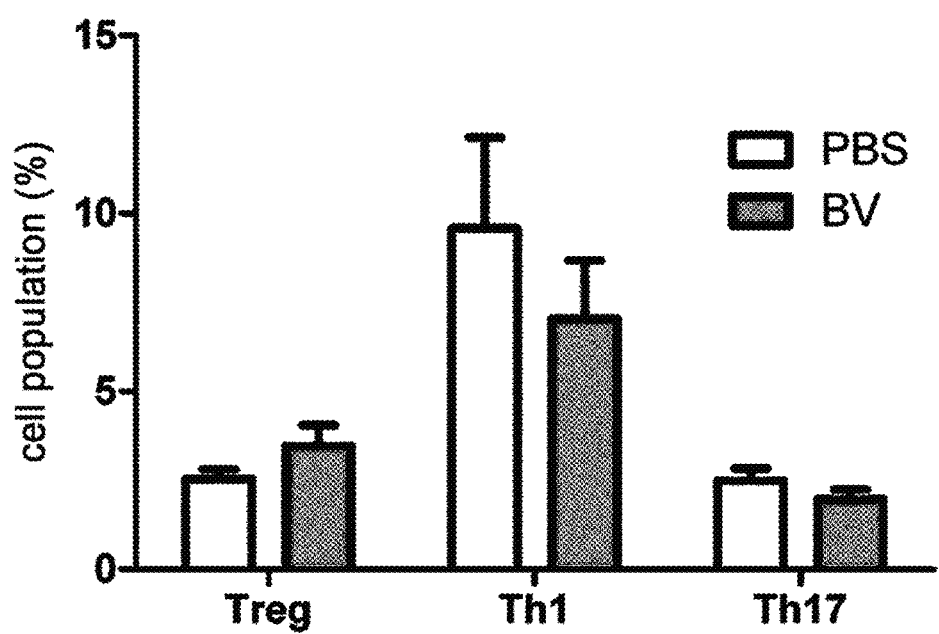

Experimental Example 6: Effect of Bee Venom on Human Treg and Th1/Th17 Differentiation Additionally, the effect of bee venom in humans was examined. In order to determine whether the level of Treg increases, a fresh PBMC separated from a healthy donor was incubated along with bee venom (1 µg/ml) or PBS for 24 hours (FIG. 7A). The result revealed that, while the level of CD4$^+$Foxp3$^+$ Treg was increased in three out of the four bee venom-treated subjects (51.19±17.94% increase vs. PBS), the bee venom treatment in the remaining one subject caused a slight decrease in the level of CD4$^+$Foxp3$^+$ Treg (5.16% decrease vs. PBS). Additionally, for the detection of the Th1/Th17 differentiation, the PBMC was treated with bee venom (1 µg/ml) and anti-CD3/28 antibodies (FIG. 7B). Interestingly, the above three subjects, which showed an increase in Treg, showed a decrease in Th1 (34.96±4.93% decrease vs. PBS) and Th17 (26.29±8.08% decrease vs. PBS) rates, but the subject, which showed a slight decrease in Treg, did not show a decrease in Th1 (9.71% increase vs. PBS) and Th17 (1.14% increase vs. PBS) rates. The above data confirmed that bee venom can strengthen the inhibitory effect of Treg in humans and also that the effect can be applied to each individual subject.

Experimental Example 7: BV-PLA2 as an Active Ingredient of Bee Venom on Immune-Regulation in Mice and Humans The bee venom of *Apis mellifera* contains various peptides and proteins including melittin, BV-PLA2, MCD, and apamin. Accordingly, the present inventors conducted an experiment to examine which component of the various bee venom components may exert an effect on Treg in mice. In particular, splenocytes, separated from the Foxp3$^{EGFP}$C57BL/6 mice, were treated with bee venom or each of the components including melittin, BV-PLA2, apamin and MCD (FIG. 8). According to the results, bee venom (P<0.05) and BV-PLA2 (P<0.01) induced a noticeable increase in the CD4$^+$CD25$^+$Foxp3$^+$ Treg, whereas other compounds failed to show the same. Accordingly, the present inventors confirmed that BV-PLA2 is an active ingredient of bee venom involved in immune-regulation. Additionally, they also examined the immune-inhibitory effect of BV-PLA2 in humans. To this end, freshly separated PBMC was treated with bee venom, BV-PLA2 or PBS and anti-CD3/28 antibodies (FIG. 9). Bee venom and BV-PLA2 showed similar results reducing the populations in Th1 (bee venom: 30.45±10.39%, BV-PLA2: 23.93±6.71% decrease vs. PBS) and Th17 (bee venom: 66.04±4.06%, BV-PLA2: 61.80±5.25% decrease vs. PBS). Conclusively, the above results confirmed that BV-PLA2 has an immune-regulation effect both in mice and humans.

Figure 10A:
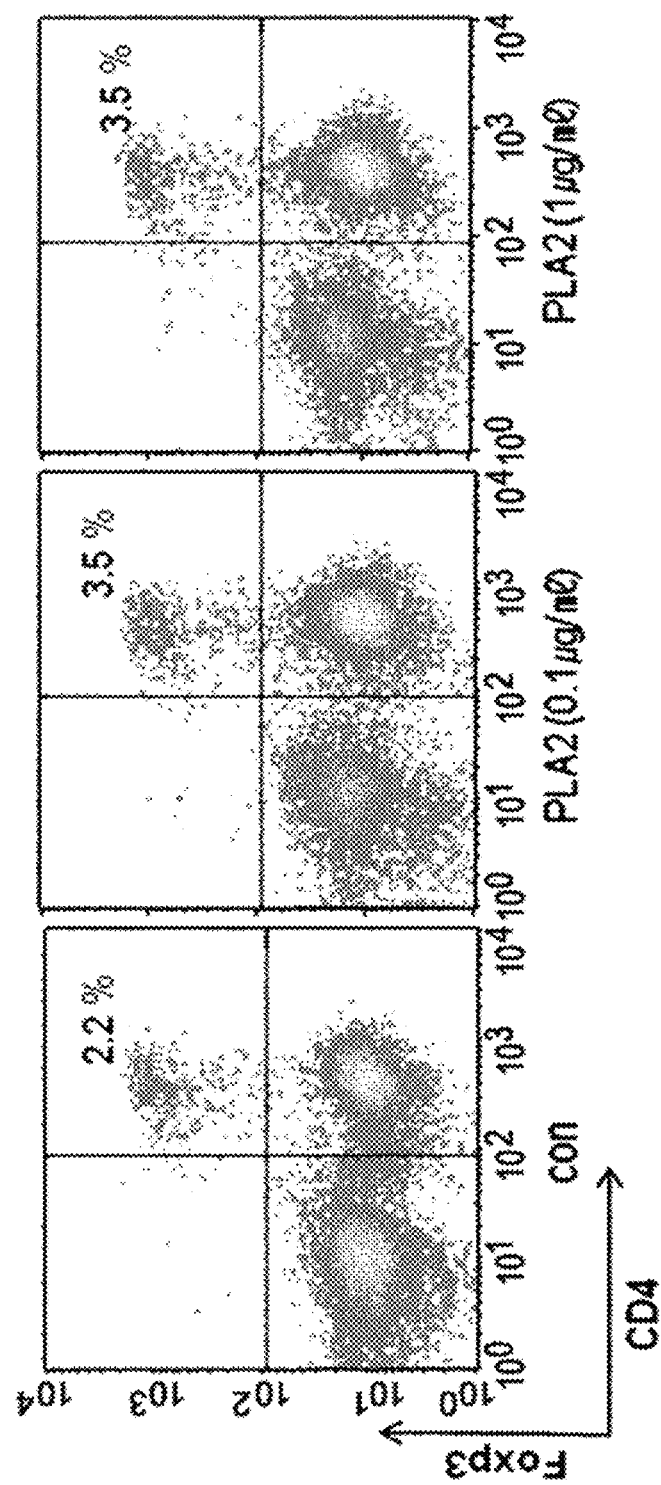
FIG. 10A-B shows in vitro CD4$^+$CD25$^+$Foxp3$^+$ Treg population of splenocytes. The splenocytes stimulated with anti-mouse CD3 antibodies and anti-mouse CD28 antibodies were treated with various concentrations of BV-PLA2 (secretory type) for 3 days. The measured values were standardized with regard to the values of the stimulated control group. (A) shows CD4$^+$CD25$^+$Foxp3$^+$ Treg from control group and that from the splenocytes treated with BV-PLA2 (0.1, 1 µg/ml). The numbers within the dot plots represent the percentage of cells belonging to the corresponding quadrant (B) shows the percentages of CD4$^+$CD25$^+$Foxp3$^+$ Treg, which was significantly increased in the CD4$^+$CD25$^+$Foxp3$^+$ Treg-treated group compared to the control group. The data is indicated via mean±SEM (standard error of the mean), and the analysis of the statistics was performed via Newman-Keuls multiple comparison test following the one-way ANOVA (*p<0.05, p<0.01, *p<0.001).
Figure 10B:
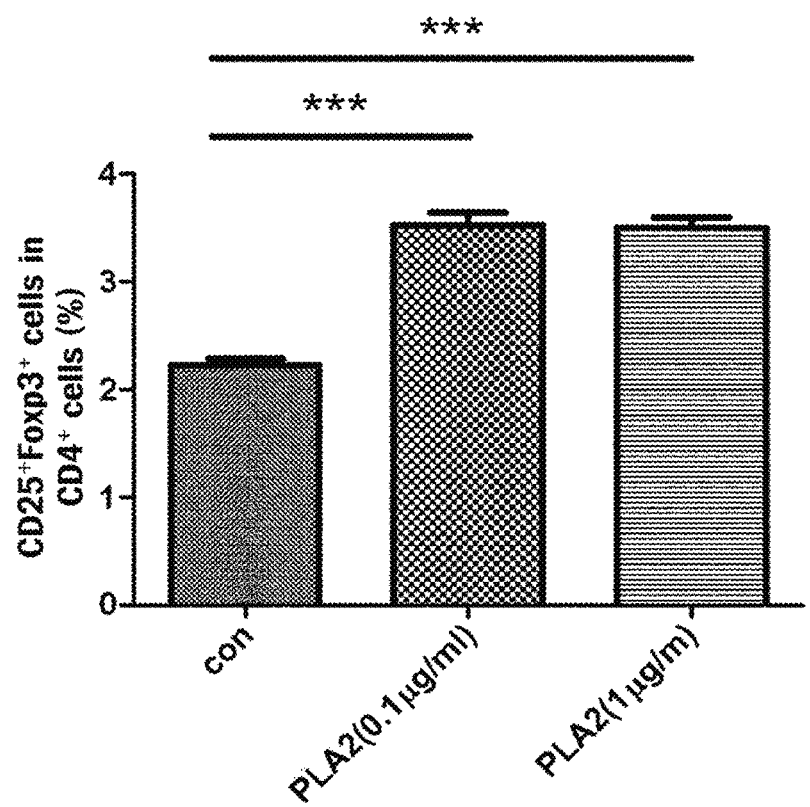
Figure 11:
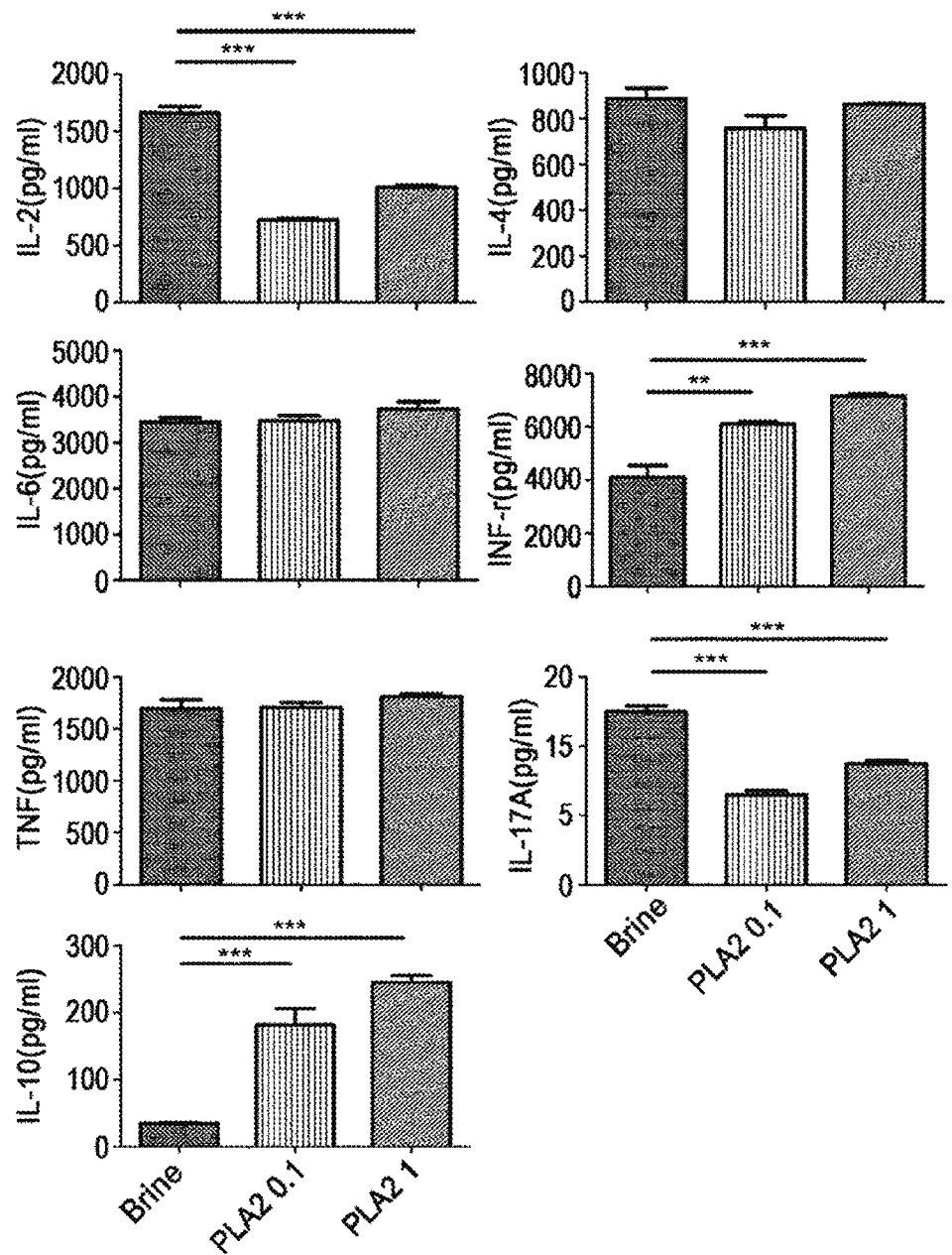
FIG. 11 shows graphs illustrating the effect of BV-PLA2 (secretory type) on cytokine production. The splenocytes stimulated with anti-mouse CD3 antibodies and anti-mouse CD28 antibodies were treated with various concentrations of BV-PLA2 for 3 days. The supernatant of the resulting culture was recovered, centrifuged at 4° C. at 300 rcf for 10 minutes, and the resultant was stored at −70° C. for future use. The measured values were standardized with regard to the values of the stimulated control group. Cytokines were measured via flow cytometry using cytometric bead array (CBA). The data is indicated via mean±SEM, and the analysis of the statistics was performed via Newman-Keuls multiple comparison test following the one-way ANOVA (*p<0.05, p<0.01, *p<0.001).

Experimental Example 8: In Vitro Effect of BV-PLA2 on Inflammatory Cytokines in CD4$^+$CD25$^+$ Foxp3$^+$ Treg and Splenocytes The group treated with BV-PLA2 showed a higher increase in CD4$^+$CD25$^+$Foxp3$^+$ Treg population than the brine-treated group. Additionally, the group treated with BV-PLA2 showed a noticeably higher increase in the percentage of CD4$^+$CD25$^+$Foxp3$^+$ Treg than the brine-treated group (FIG. 10). The levels of IL-2, the Th1 cytokine capable of activating B cell by Th2, were more significantly decreased in the culture supernatant of the group treated with BV-PLA2 than in the brine-treated group. The above decrease in IL-2 indicates that BV-PLA2 can inhibit the inflammation caused by B cell immune responses. The levels of IL-10, a kind of Treg cytokines, were substantially increased in the group treated with BV-PLA2 than in the brine-treated group. However, BV-PLA2 failed to show any effect of statistical significance (FIG. 11).

Figure 12:
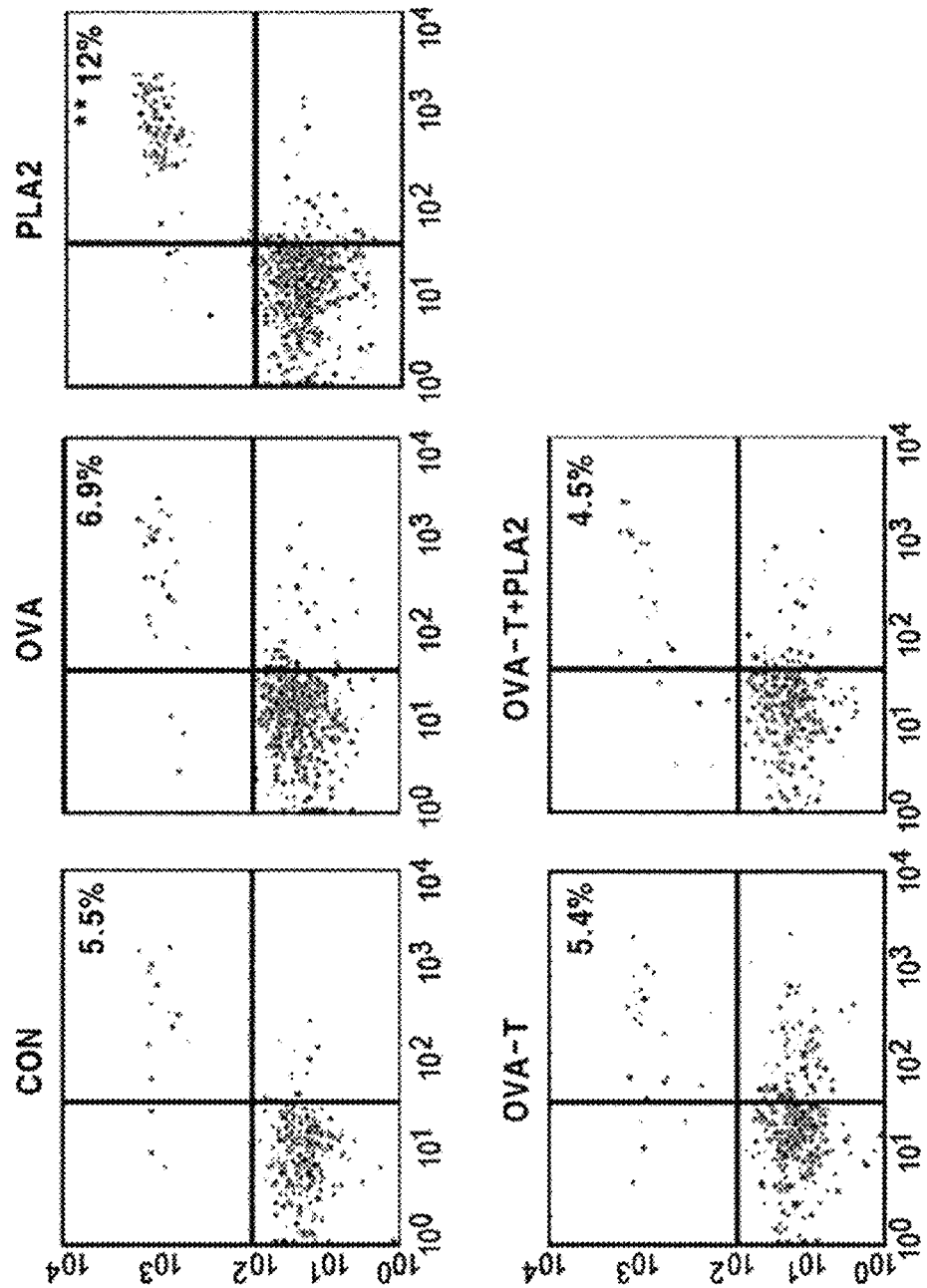
FIG. 12 shows CD4$^+$CD25$^+$Foxp3$^+$ Treg populations in an ovalbumin (OVA)-induced asthma group, which are the results in, in a clockwise direction from the left upper end, control group (CON); a group with no treatment after OVA induction (OVA); a group introduced to with BV-PLA2 after OVA induction (OVA+PLA2); a group introduced with BV-PLA2 (secretory type) after OVA induction and anti-CD25 antibodies injection (OVA-T+PLA2); and a group with OVA induction and introduction with anti-CD25 antibodies injection (OVA-T). Specifically, isolated alveolar cells were stained with anti-CD4 allophycocyanine and anti-CD25 phycoerythrin (PE), and analyzed via flow cytometry. The data is indicated via mean±SEM, and the analysis of the statistics was performed via Newman-Keuls multiple comparison test following the one-way ANOVA (n=4).

Experimental Example 9: Effect of BV-PLA2 on CD4+CD25+Foxp3+ Treg in OVA-Induced Asthma Group In alveolar cells separated from an OVA-induced asthma mouse model, the OVA group showed a higher decrease in the CD4$^+$CD25$^+$Foxp3$^+$ Treg population than the CON group. The (OVA+PLA2) group showed a higher increase in CD4$^+$CD25$^+$Foxp3$^+$ Treg population than the OVA group. The above results confirmed that BV-PLA2 can improve reduced Treg in allergic asthma (FIG. 12).

Figure 13:
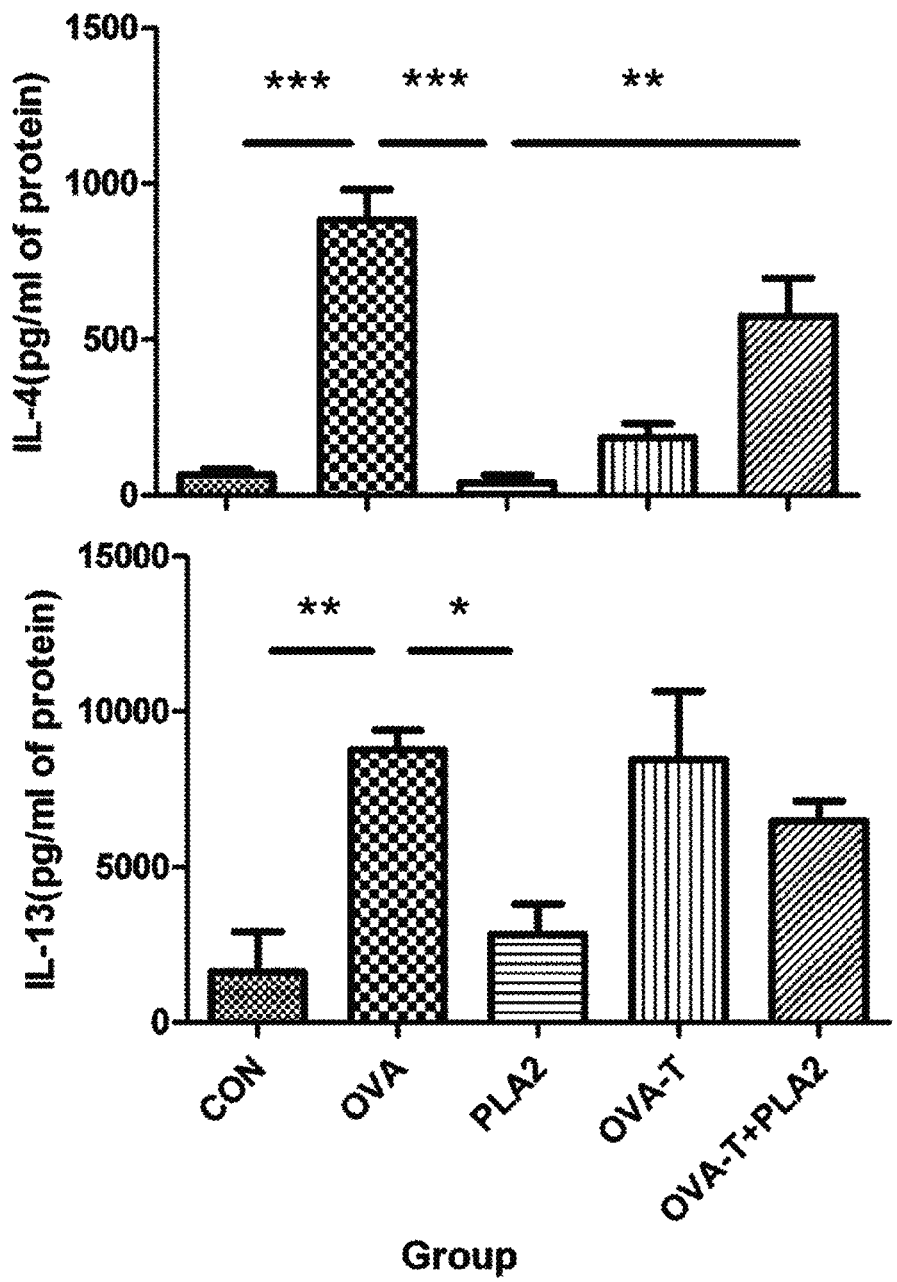
FIG. 13 shows graphs illustrating the effect of BV-PLA2 (secretory type) on the production of IL-4 and IL-13 cytokines in bronchoalveolar lavage fluid (BALF). The level of Th2 inflammatory cytokine was shown higher in groups of OVA, OVA-T and (OVA-T+PLA2) than in groups of (OVA+PLA2) and CON. The data is indicated via mean±SEM, and the analysis of the statistics was performed via Newman-Keuls multiple comparison test following the one-way ANOVA (*p<0.001, p<0.05 vs. CON, n=4).

Experimental Example 10: Effect of BV-PLA2 on Th2 Cytokines (IL-4 and IL-13) in BALF The cytokine levels in the BALF of the control group and each mouse model of the experimental groups were measured. According to the result, the OVA, OVA-T and (OVA-T+PLA2) groups showed a higher increase in the level of Th2 inflammatory cytokine than the (OVA+PLA2) group and the control group (FIG. 13). BV-PLA2 could reduce the production of the inflammatory cytokine increased due to OVA treatment, but in the Treg-deficient group, BV-PLA2 treatment failed to show the above inhibitory effect. Accordingly, it was confirmed that Treg is involved in the inhibition of inflammatory cytokine secretion by BV-PLA2.

Experimental Example 11: Effect of BV-PLA2 on IgE Titer in Sera

Figure 14:
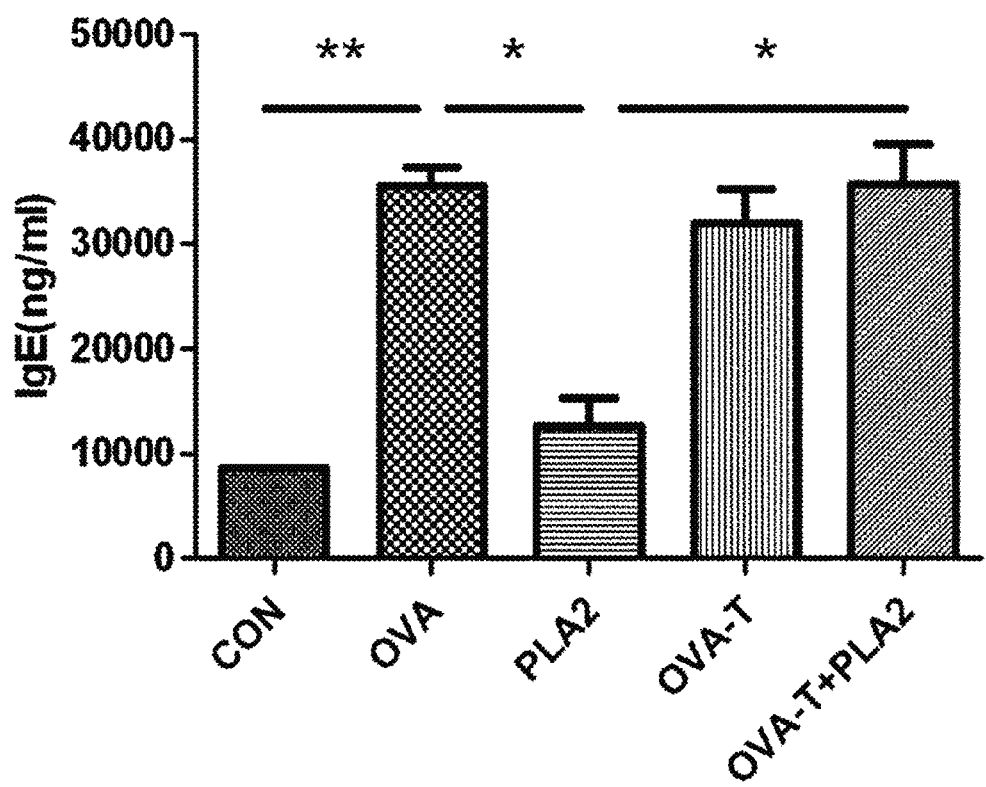
FIG. 14 shows a graph illustrating the IgE level in the blood sera of the control group and the experimental groups. Blood samples were collected via cardiac puncture and the level of IgE in the samples was analyzed via ELISA. The data is indicated via mean±SEM, and the analysis of the statistics was performed via Newman-Keuls multiple comparison test following the one-way ANOVA (*p<0.05, **p<0.01 vs. CON, n=4).

The OVA group showed a noticeably higher increase in IgE concentration in the serum than the CON group. This indicates that the asthma induction in an animal model of the present invention conducted in Example 1.2 was successfully performed. The (OVA-T+PLA2) group showed a significantly higher decrease in the serum IgE concentration than in the OVA, OVA-T and (OVA-T+PLA2) groups. BV-PLA2 could inhibit the increase in serum IgE concentration in OVA-induced allergic asthma mice, but the effect of BV-PLA2 failed to show in the Treg-deficient group (FIG. 14). This suggests that the inhibitory effect of BV-PLA2 against the increase of serum IgE concentration may occur via Treg activation.

Figure 15:
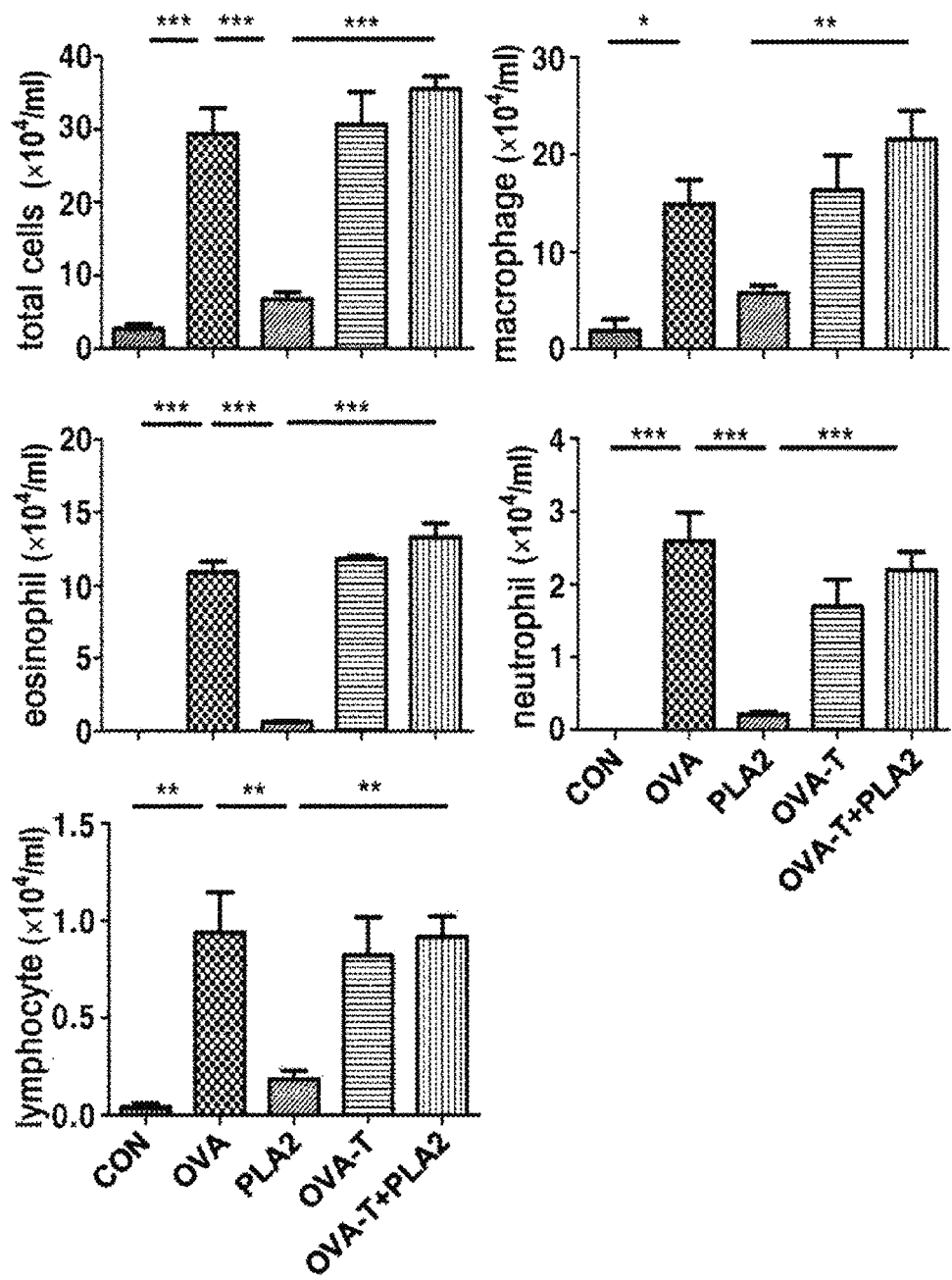
FIG. 15 shows graphs illustrating the effect of BV-PLA2 (secretory type) on the recruitment of leucocytes in the airway of OVA-induced asthma mice. After establishing the OVA-induced asthma mouse model, BLAF was collected from the lungs of the mice. The total cells, eosinophils, macrophages, neutrophils, and lymphocytes were counted from the BALF. The data is indicated via mean±SEM, and the analysis of the statistics was performed via Newman-Keuls multiple comparison test following the one-way ANOVA ($*p<0.05$, $p<0.01$, $*p<0.001$ vs. CON and OVA, n=4).
Figure 16A:
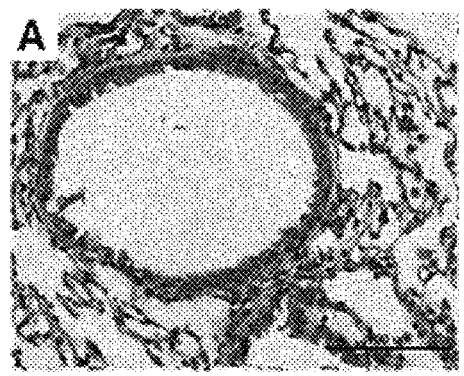
FIG. 16A-E shows pictures illustrating the effect of BV-PLA2 (secretory type) on the recruitment of inflammatory cells into the lung tissues of OVA-induced allergic asthma mice. Balb/c Foxp3$^{+EGFP}$ Balb/c mice were sensitized with OVA and test-infected. The lung tissues were stained with hematoxylin and eosin (H&E) (400× magnification). The results shown represent: (A) a group of PBS-test infected mice treated with PBS (CON); (B) a group of OVA-test infected mice treated with PBS (OVA); (C) OVA-test infected mice treated with BV-PLA2 (0.2 mg/kg) (OVA+PLA2); (D) a group of OVA and anti-CD25 antibodies-test infected mice treated with BV-PLA2 (0.2 mg/kg) (OVA-T+PLA2); and (E) a group of OVA and anti-CD25 antibodies-test infected mice (OVA-T).
Figure 16B:
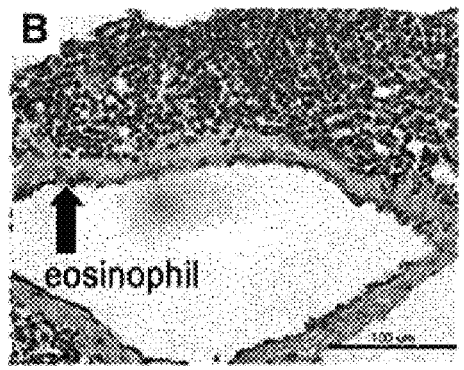
Figure 16C:
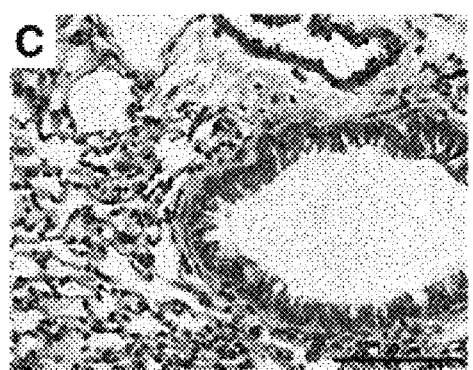
Figure 16D:
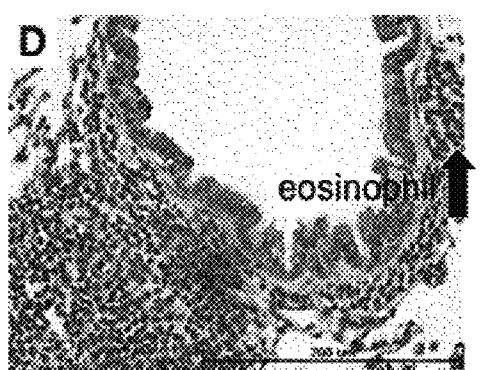
Figure 16E:
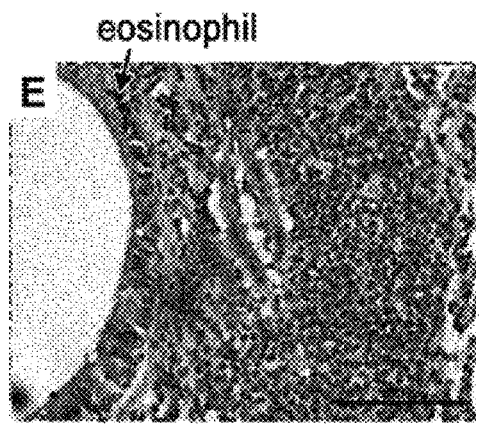

Experimental Example 12: Effect of BV-PLA2 on Total Cells and Inflammatory Cells in BAL The OVA group showed a significantly higher increase in the number of total cells, eosinophils, and lymphocytes than the CON group. This indicates that the asthma induction in an animal model of the present invention conducted in Example 1.2 was successfully performed. The (OVA+PLA2) group showed a significantly higher decrease in the number of total cells, eosinophils, and lymphocytes than in the OVA, OVA-T and (OVA-T+PLA2) groups. BV-PLA2 could inhibit the increase of inflammatory cells such as the total BAL cells, eosinophils, lymphocytes in OVA-induced allergic asthma mice, but the effect of BV-PLA2 failed to show in the Treg-deficient group (FIG. 15). This suggests that the inhibitory effect of BV-PLA2 against the increase of the total BAL cells, eosinophils, lymphocytes may occur via Treg activation.

Experimental Example 13: Effect of BV-PLA2 on the Change in Lung Shape in an OVA-Induced Asthma Model In order to analyze the effect of PLA2 on the histological characteristics of asthma, the lung tissues of OVA-induced allergic asthma mice were subjected to H&E and PAS staining. According to the result, the lung tissue slices obtained from the mice exposed to OVA showed an airway inflammation, and pulmonary infiltration with eosinophils around the bronchial was observed (FIG. 16). In contrast, the lung tissue slices obtained from the mice treated with BV-PLA2 showed a decrease in airway inflammation. The periodic Acid Schiff (PAS)-positive mucus-count goblet cells present around the bronchial airway were detected in the OVA, OVA-T and (OVA-T+PLA2) groups. Meanwhile, BV-PLA2 treatment significantly reduced PAS-positive goblet cells around the bronchial airway (FIG. 17). The discovery suggests that BV-PLA2 has the potential of reforming an effective airway.

Experimental Example 14: Effect of BV-PLA2 on Airway Hyperresponsiveness in an OVA-Induced Asthma Model In order to confirm the inhibitory effect of BV-PLA2 against airway hyperresponsiveness, $P_{enh}$ values were measured. At concentrations of 50 mg/ml and 100 mg/ml of methacholine, the OVA, OVA-T and (OVA-T+PLA2) groups showed a noticeably higher increase in $P_{enh}$ value than in the BV-PLA2 group. Meanwhile, the group treated with BV-PLA2 showed a decrease in the increased $P_{enh}$ value at 50 mg/ml and 100 mg/ml concentrations of methacholine relative to the CON group of the OVA-induced asthma mice (*P<0.05, **P<0.01; FIG. 18).

Experimental Example 15: Effect of BV-PLA2 on Protection of Dopaminergic (DA) Neurons in Substantia Nigra (SN) in a Parkinson's Disease Animal Model Seven days after MPTP-addiction, the brain slices of an MPTP-induced Parkinson's disease animal model prepared in Example 1.3 were acquired, and DA neurons were immunostained with anti-TH antibodies. The BV-PLA2 treatment noticeably increased the number of TH$^+$ neurons in SN to 32% compared to that of the mice in the MPTP-addicted control group (P<0.01; FIG. 1).

BV-PLA2 treatment induced the activation of microglia after the infiltration of CD4$^+$ T cells in SN. According to a recent report, CD4$^+$CD25$^+$ Treg mediates the protection of neurons by inhibiting microglia reaction in an MPTP-induced PD model. In order to confirm whether Treg is involved in the neuron protection by BV-PLA2, MPTP-addicted mice were intraperitoneally injected with anti-CD25 antibodies (1 mg/kg) one day prior to MPTP to administration, and thereby reduced the number of Treg cells. The BV-PLA2 treatment on the mice with a reduced number of Treg cells failed to reduce the DA neuronal death unlike the MPTP-addicted mice.

Experimental Example 16: Gene Synthesis and Construction

The BV-PLA2 used in the present invention accounts for about from 10% to 20% of bee venom components, and the recombinant BV-PLA2 was prepared by RNA extraction from the honey bee (*Apis mellifera*), followed by cDNA synthesis, and PCR amplification using BV-PLA2-specific primers. The amplified gene was replicated into SalI and EcoRI restriction sites in the pEcoli-Nterm 6×HN vector. The recombinant plasmid was transformed into *E. coli* strain DH5α and the recombinant plasmid DNA was extracted therefrom, and confirmed whether it was the correct recombinant BV-PLA2 via sequencing analysis of the recombinant plasmid DNA. For a large-scale production of the recombinant BV-PLA2, the recombinant plasmid were introduced into *E. coli* strain BL21 via transformation. The four types (F, A, B, and C) of BV-PLA2 used in the experiments were replicated into the pEcoli-Nterm 6×HN vector in the same manner as described above (FIG. 20).

Experimental Example 17: Purification of Recombinant BV-PLA2 and its Enzyme Activity The various types of the recombinant BV-PLA2 prepared in the present invention were extracted in the same manner as described above, and confirmed via SDS-PAGE using 15% (w/v) polyacrylamide. As a result, it was confirmed that native secretory type BV-PLA2 is a protein with a size of 134 AA, F-type recombinant BV-PLA2 with 201 AA, A-type recombinant BV-PLA2 with 133 AA, B-type recombinant BV-PLA2 with 166 AA, and C-type recombinant BV-PLA2 168 AA (FIG. 21A; A-type not shown).

Enzyme activities were analyzed for the above three types of recombinant BV-PLA2s and the native BV-PLA2 using an ENZCHECK® phospholipase A2 analysis kit (Invitrogen), which utilizes DOPC substrate, as described in Example 14.3. According to the measurement, the activity of the native BV-PLA2 was 8 U/MW, and that of the F-type recombinant BV-PLA2 was 2 U/MW, but the enzyme activity of the B-type recombinant BV-PLA2 was not measured. In contrast, the enzyme activity in the C-type recombinant BV-PLA2 measured was shown to be similar to that of the native BV-PLA2, which is a positive control group (FIG. 21B).

Experimental Example 18: Effect of Recombinant BV-PLA2 on CD4$^+$CD25$^+$Foxp3$^+$ Regulatory T Cell (Treg)

In order to examine whether the recombinant BV-PLA2 can control the CD4$^+$CD25$^+$Foxp3$^+$ regulatory T cells (Treg) in splenocytes, spleens were obtained from six to eight-week old C57BL/6$^{Foxp3\text{-}EGFP}$ mice. The splenocytes were stimulated with anti-mouse CD3 antibodies and anti-mouse CD28 antibodies, and treated with the native BV-PLA2 and the respective recombinant BV-PLA2 at a concentration of 1 mg/ml for three days, stained with anti-CD4-APC and anti-CD25-PE monoclonal antibodies, and were measured using a flow cytometer. The native BV-PLA2 showed a two-fold or higher of increase than that of the control group (1.66%), whereas F and B types showed no effect compared to that of the control group. In contrast, the C-type recombinant BV-PLA2 was shown to have 3.96% thus confirming that it is effective on the increase of CD4$^+$CD25$^+$Foxp3$^+$ regulatory Tcells in the splenocytes (FIGS. 22A through 22E).

Additionally, in order to examine whether the recombinant BV-PLA2 controls the CD4$^+$CD25$^+$Foxp3$^+$ regulatory T cells (Treg) in CD4$^+$ T cells, spleens were obtained from six to eight-week old C57BL/6$^{Foxp3\text{-}EGFP}$ mice. Only the CD4$^+$ T cells were separated from the splenocytes via MACS CD4 (L3T4) MicroBeads, stimulated with anti-mouse CD3 antibodies and anti-mouse CD28 antibodies, treated with the native BV-PLA2 and the respective recombinant BV-PLA2 at a concentration of 1 mg/ml for three days, stained with anti-CD4-APC and anti-CD25-PE monoclonal antibodies, and were measured using a flow cytometer. The native BV-PLA2 showed a two-fold or higher of increase than that of the control group (2%), whereas F and B types showed no effect compared to that of the control group. In contrast, the C-type recombinant BV-PLA2 was shown to have 4% thus confirming that it is effective on the increase of CD4$^+$CD25$^+$Foxp3$^+$ regulatory Tcells in the splenocytes (FIG. 23).

Figure 24A:
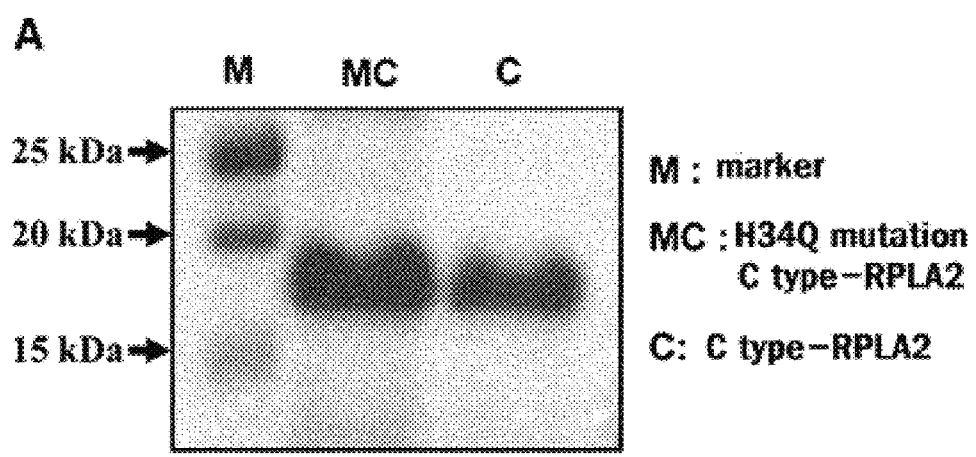
FIG. 24A-B: (A) shows a result of SDS-PAGE for confirmation of the C-type recombinant BV-PLA2 and C-type mutant (H34Q) recombinant BV-PLA2, and (B) shows a comparison result of the activities of a natural secretory BV-PLA2 and the above enzymes.

Experimental Example 19: Preparation of C-Type Mutant (H34Q) Recombinant BV-PLA2 and its Enzyme Activity The enzyme active site of the C-type mutant (H34Q) recombinant BV-PLA2 (SEQ ID NO: 11), prepared by the method described in Example 15 of the present invention, was modified from histidine to glutamine, and the C-type mutant (H34Q) recombinant BV-PLA2 was extracted in the same manner as described above, and confirmed via SDS-PAGE using 15% (w/v) polyacrylamide. The protein size of the C-type recombinant BV-PLA2 and the C-type mutant (H34Q) recombinant BV-PLA2, i.e., 171 AA, was confirmed via SDS-PAGE (FIG. 24A).

Figure 24B:
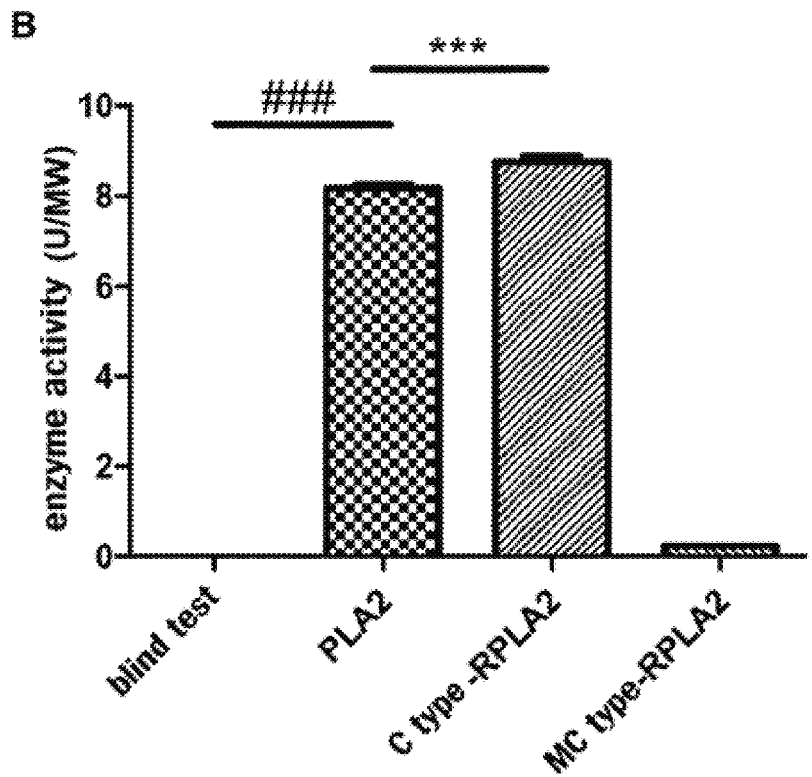

The enzyme activity of the C-type mutant (H34Q) recombinant BV-PLA2 prepared above was measured using ENZCHECK® phospholipase A2 analysis kit (Invitrogen), which utilizes DOPC as a substrate. According to the measurement, the activity of the native BV-PLA2 was 8 U/MW, and the activity of the C-type mutant (H34Q) recombinant BV-PLA2 was shown similar to that of the native BV-PLA2. However, the measured activity of the C-type mutant (H34Q) recombinant BV-PLA2 was low (FIG. 24B).

Experimental Example 20: Effect of C-Type Mutant (H34Q) Recombinant BV-PLA2 on CD4+CD25+Foxp3+ Regulatory T Cells (Treg)

Figure 25A:
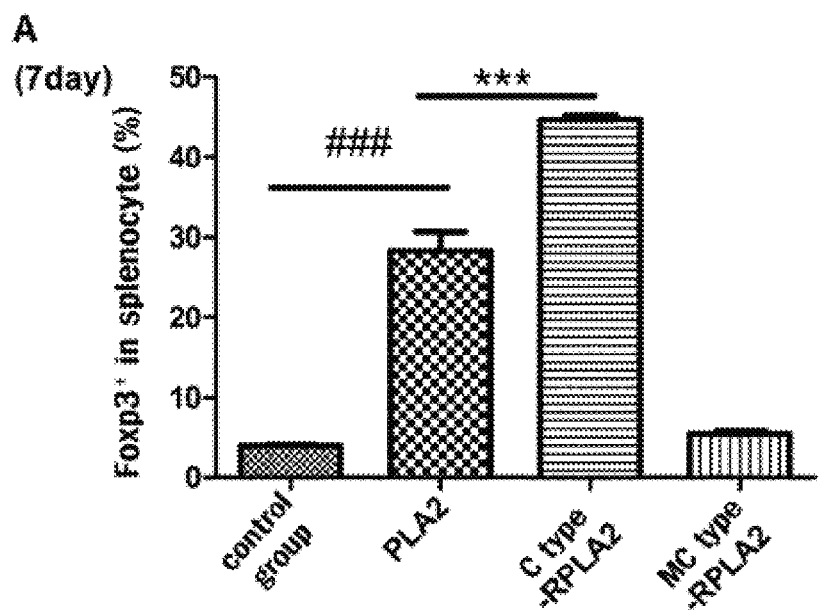
FIG. 25A-B shows (A) a graph showing the effects of the natural secretory BV-PLA2, C-type recombinant BV-PLA2, and C-type mutant (H34Q) recombinant BV-PLA2 on the Foxp3$^+$ population among splenocytes, and (B) a graph showing the effects of the natural secretory BV-PLA2, C-type recombinant BV-PLA2, and C-type mutant (H34Q) recombinant BV-PLA2 on the Foxp3$^+$ population among CD4$^+$ cells.
Figure 25B:
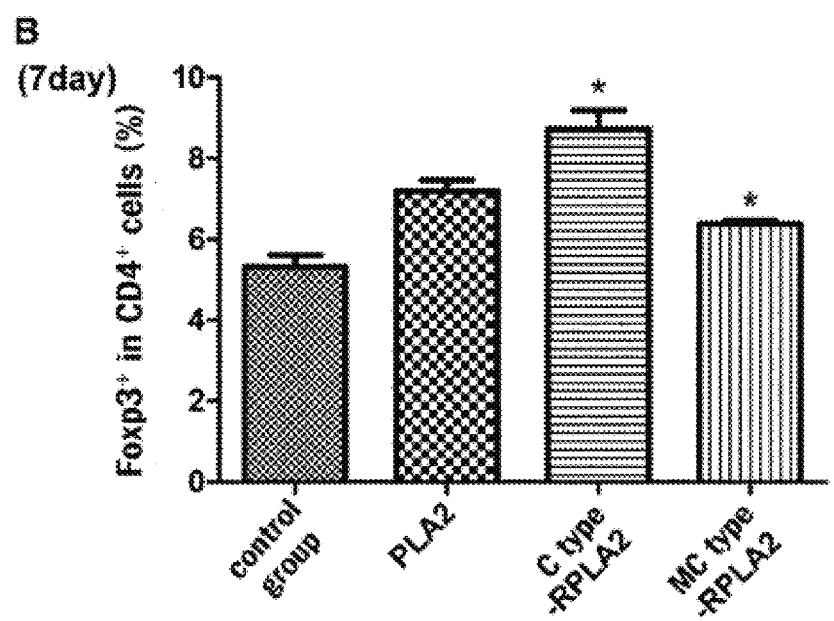

In order to examine whether the C-type mutant (H34Q) recombinant BV-PLA2 prepared above can control the CD4$^+$CD25$^+$Foxp3$^+$ regulatory T cells (Treg) in the splenocytes and the CD4$^+$ T cells, spleens were obtained from six to eight-week old C57BL/6$^{Foxp3\text{-}EGFP}$ mice. The sample of the splenocytes and the sample obtained by separating only CD4$^+$ T cells from the splenocytes via MACS CD4 (L3T4) MicroBeads, were respectively stimulated with anti-mouse CD3 antibodies and anti-mouse CD28 antibodies, treated with the native BV-PLA2 at a concentration of 1 mg/ml, and the C-type recombinant BV-PLA2 and the C-type mutant (H34Q) recombinant BV-PLA2 at a concentration of 2 mg/ml, respectively, for seven days, stained with anti-CD4-APC and anti-CD25-PE monoclonal antibodies, and were measured using a flow cytometer. In the splenocytes, the native BV-PLA2 showed an increase by 28%, and the C-type recombinant BV-PLA2 showed an increase by 45%, respectively, compared to that of the control group, whereas the C-type mutant (H34Q) recombinant BV-PLA2 showed no effect compared to that of the control group (FIG. 25A). Meanwhile, in the CD4$^+$ T cells, the native BV-PLA2 showed an increase by 7%, the C-type recombinant BV-PLA2 showed an increase by 9%, respectively, compared to that of the control group, whereas the C-type mutant (H34Q) recombinant BV-PLA2 showed no effect on the increase of CD4$^+$CD25$^+$Foxp3$^+$ regulatory T cells (Treg), compared to that of the control group (FIG. 25B).

The invention claimed is:

1. A method for treating rheumatoid arthritis, multiple sclerosis or psoriasis comprising:

administering an effective amount of a composition comprising an isolated polypeptide to a subject having rheumatoid arthritis, multiple sclerosis or psoriasis, wherein the polypeptide comprises the amino acid sequence of SEQ ID NO:6.

* * * * *